US010286077B2

(12) United States Patent
Shadiack et al.

(10) Patent No.: US 10,286,077 B2
(45) Date of Patent: May 14, 2019

(54) STEROID HORMONE COMPOSITIONS IN MEDIUM CHAIN OILS

(71) Applicant: TherapeuticsMD, Inc., Boca Raton, FL (US)

(72) Inventors: Annette Shadiack, Somerset, NJ (US); Peter H. R. Persicaner, Boca Raton, FL (US); Philip B. Inskeep, East Lyme, CT (US); Thorsteinn Thorsteinsson, Boynton Beach, FL (US); Frederick D. Sancilio, Palm Beach Gardens, FL (US); Jason D. Legassie, Stuart, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 0 days.

(21) Appl. No.: 15/473,742

(22) Filed: Mar. 30, 2017

(65) Prior Publication Data

US 2017/0281776 A1    Oct. 5, 2017

Related U.S. Application Data

(60) Provisional application No. 62/317,056, filed on Apr. 1, 2016.

(51) Int. Cl.
| | | |
|---|---|---|
| *A61K 47/26* | (2006.01) | |
| *A61K 47/14* | (2017.01) | |
| *A61K 31/57* | (2006.01) | |
| *A61K 9/00* | (2006.01) | |
| *A61K 9/14* | (2006.01) | |

(52) U.S. Cl.
CPC ............ *A61K 47/26* (2013.01); *A61K 9/0053* (2013.01); *A61K 9/145* (2013.01); *A61K 31/57* (2013.01); *A61K 47/14* (2013.01)

(58) Field of Classification Search
CPC ...... A61K 47/26; A61K 47/14; A61K 9/0053; A61K 31/57
USPC ........................................................ 514/177
See application file for complete search history.

(56) References Cited

U.S. PATENT DOCUMENTS

| | | |
|---|---|---|
| 1,967,351 A | 7/1934 | Doisy |
| 2,232,438 A | 2/1941 | Butenandt |
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Reinhardt et al. |
| 3,526,648 A | 9/1970 | Daniel et al. |
| 3,710,795 A | 1/1973 | Higuchi et al. |
| 3,729,560 A | 4/1973 | Hagerman |
| 3,729,566 A | 4/1973 | Youngdale et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 7/1976 | Zaffaroni |
| 3,977,404 A | 8/1976 | Theeuwes |
| 3,993,072 A | 11/1976 | Zaffaroni |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 4/1977 | Higuchi et al. |
| 4,071,623 A | 1/1978 | Van Der Vies |
| 4,093,709 A | 6/1978 | Choi et al. |
| 4,154,820 A | 5/1979 | Simoons |
| 4,155,991 A | 5/1979 | Hartmann et al. |
| 4,196,188 A | 4/1980 | Besins |
| 4,215,691 A | 8/1980 | Wong |
| 4,237,885 A | 12/1980 | Pharriss et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |
| 4,449,980 A | 5/1984 | Millar et al. |
| 4,572,915 A | 2/1986 | Crooks |
| 4,610,687 A | 9/1986 | Fogwell |
| 4,629,449 A | 12/1986 | Wong |
| 4,719,239 A | 1/1988 | Muller et al. |
| 4,727,109 A | 2/1988 | Schmidt et al. |

(Continued)

FOREIGN PATENT DOCUMENTS

| | | |
|---|---|---|
| BR | PI1001367 A2 | 7/2012 |
| CN | 102258455 A | 11/2011 |

(Continued)

OTHER PUBLICATIONS

US 6,214,374 B1, 04/2001, Schmirler et al. (withdrawn)
P. A. Reqidor, Geburtshilfe and Frauenheilkunde (2014), 74(11), p. 995-1002.*
Imwitor 988, Cream Care, Creamer Oleo GmbH & Co KG (2013).*
Rajeswara, Rao P., et al., "The Affect of Capmul, Labrafil and Transcutol on Progesterone 100 Mg Soft Capsules Bioavailability in Indian Healthy Adult Postmenopausal Female Subjects Under Fasting Conditions," *Bioequivalence & Bioavailability*: vol. 7(2): pp. 95-107 (2015).
Degenhardt, J., "Monoterpene and Sesquiterpene Synthases and the Origin of Terpene Skeletal Diversity in Plants," *Phytochemistry* 70(15-16):1621-1637, Elsevier, England (2009).

(Continued)

*Primary Examiner* — Yong L Chu
(74) *Attorney, Agent, or Firm* — Sterne, Kessler, Goldstein & Fox P.L.L.C.

(57) ABSTRACT

This disclosure provides a novel pharmaceutical composition capable of forming micelles upon exposure to the gastric environment. The pharmaceutical composition is suitable for delivering steroid hormones, and progesterone in particular, to a subject in need thereof.

15 Claims, 11 Drawing Sheets

(56) References Cited

U.S. PATENT DOCUMENTS

| | | |
|---|---|---|
| 4,732,763 A | 3/1988 | Beck et al. |
| 4,738,957 A | 4/1988 | Laurent et al. |
| 4,756,907 A | 7/1988 | Beck et al. |
| 4,762,717 A | 8/1988 | Crowley, Jr. |
| 4,788,062 A | 11/1988 | Gale et al. |
| 4,816,257 A | 3/1989 | Buster et al. |
| 4,822,616 A | 4/1989 | Zimmermann et al. |
| 4,865,848 A | 9/1989 | Cheng et al. |
| 4,900,734 A | 2/1990 | Maxson et al. |
| 4,906,475 A | 3/1990 | Kim |
| 4,942,158 A | 7/1990 | Sarpotdar et al. |
| 4,944,949 A | 7/1990 | Story et al. |
| 4,961,931 A | 10/1990 | Wong |
| 5,030,629 A | 7/1991 | Rajadhyaksha |
| 5,064,654 A | 11/1991 | Berner et al. |
| 5,071,643 A | 12/1991 | Yu et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,211,952 A | 5/1993 | Spicer et al. |
| 5,252,334 A | 10/1993 | Chiang et al. |
| 5,280,023 A | 1/1994 | Ehrlich et al. |
| 5,288,496 A | 2/1994 | Lewis |
| 5,340,584 A | 8/1994 | Spicer et al. |
| 5,340,585 A | 8/1994 | Pike et al. |
| 5,340,586 A | 8/1994 | Pike et al. |
| 5,362,497 A | 11/1994 | Yamada et al. |
| 5,364,632 A | 11/1994 | Benita et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmueller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Hoffmann et al. |
| 5,543,150 A | 8/1996 | Bologna et al. |
| 5,547,948 A | 8/1996 | Barcomb |
| 5,556,635 A | 9/1996 | Istin et al. |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Mikler et al. |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Teillaud et al. |
| 5,607,691 A | 3/1997 | Hale et al. |
| 5,607,693 A | 3/1997 | Bonte et al. |
| 5,609,617 A | 3/1997 | Shealy et al. |
| 5,620,705 A | 4/1997 | Dong et al. |
| 5,626,866 A | 5/1997 | Ebert et al. |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,645,856 A | 7/1997 | Lacy et al. |
| 5,653,983 A | 8/1997 | Meybeck et al. |
| 5,656,286 A | 8/1997 | Miranda et al. |
| 5,656,289 A | 8/1997 | Cho et al. |
| 5,660,839 A | 8/1997 | Allec et al. |
| 5,662,927 A | 9/1997 | Ehrlich et al. |
| 5,663,160 A | 9/1997 | Meybeck et al. |
| 5,676,968 A | 10/1997 | Lipp et al. |
| 5,677,292 A | 10/1997 | Li et al. |
| 5,686,097 A | 11/1997 | Taskovich et al. |
| 5,693,335 A | 12/1997 | Xia et al. |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Kanios et al. |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi et al. |
| 5,770,227 A | 6/1998 | Dong et al. |
| 5,776,495 A | 7/1998 | Duclos et al. |
| 5,780,044 A | 7/1998 | Yewey et al. |
| 5,780,050 A | 7/1998 | Jain et al. |
| 5,785,976 A | 7/1998 | Westesen et al. |
| 5,788,980 A | 8/1998 | Nabahi |
| 5,788,984 A | 8/1998 | Guenther et al. |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,820,878 A | 10/1998 | Hirano et al. |
| 5,827,200 A | 10/1998 | Caillouette |
| 5,840,327 A | 11/1998 | Gale et al. |
| 5,843,468 A | 12/1998 | Burkoth et al. |
| 5,843,979 A | 12/1998 | Wille et al. |
| 5,858,394 A | 1/1999 | Lipp et al. |
| 5,863,552 A | 1/1999 | Yue |
| 5,866,603 A | 2/1999 | Li et al. |
| 5,882,676 A | 3/1999 | Lee et al. |
| 5,885,612 A | 3/1999 | Meconi et al. |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen et al. |
| 5,904,931 A | 5/1999 | Lipp et al. |
| 5,906,830 A | 5/1999 | Farinas et al. |
| 5,912,010 A | 6/1999 | Wille et al. |
| 5,916,176 A | 6/1999 | Caillouette |
| RE36,247 E | 7/1999 | Plunkett et al. |
| 5,919,477 A | 7/1999 | Bevan et al. |
| 5,922,349 A | 7/1999 | Elliesen et al. |
| 5,928,666 A | 7/1999 | Farinas et al. |
| 5,942,243 A | 8/1999 | Shah |
| 5,952,000 A | 9/1999 | Venkateshwaran et al. |
| 5,958,446 A | 9/1999 | Miranda et al. |
| 5,962,445 A | 10/1999 | Stewart |
| 5,968,919 A | 10/1999 | Samour et al. |
| 5,972,372 A | 10/1999 | Saleh et al. |
| 5,980,945 A | 11/1999 | Ruiz |
| 5,985,311 A | 11/1999 | Cordes et al. |
| 5,985,850 A | 11/1999 | Falk et al. |
| 5,985,861 A | 11/1999 | Levine et al. |
| 5,989,568 A | 11/1999 | Breton et al. |
| 5,993,856 A | 11/1999 | Ragavan et al. |
| 6,001,846 A | 12/1999 | Edwards et al. |
| 6,007,835 A | 12/1999 | Bon-Lapillonne et al. |
| 6,010,715 A | 1/2000 | Wick et al. |
| 6,013,276 A | 1/2000 | Math et al. |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |
| 6,030,948 A | 2/2000 | Mann |
| 6,039,968 A | 3/2000 | Nabahi |
| 6,040,340 A | 3/2000 | Chwalisz et al. |
| 6,056,972 A | 5/2000 | Hermsmeyer |
| 6,060,077 A | 5/2000 | Meignant |
| 6,068,853 A | 5/2000 | Giannos et al. |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |
| 6,086,916 A | 7/2000 | Agnus et al. |
| 6,087,352 A | 7/2000 | Trout |
| 6,090,404 A | 7/2000 | Meconi et al. |
| 6,096,338 A | 8/2000 | Lacy et al. |
| 6,106,848 A | 8/2000 | Preuilh et al. |

(56) References Cited

U.S. PATENT DOCUMENTS

| | | | |
|---|---|---|---|
| 6,107,276 A | 8/2000 | Carli et al. | |
| 6,117,446 A | 9/2000 | Place | |
| 6,117,450 A | 9/2000 | Dittgen et al. | |
| 6,124,362 A | 9/2000 | Bradbury et al. | |
| 6,133,251 A | 10/2000 | Dittgen et al. | |
| 6,133,320 A | 10/2000 | Yallampalli et al. | |
| 6,139,868 A | 10/2000 | Hoffmann | |
| 6,139,873 A | 10/2000 | Hughes, Jr. et al. | |
| 6,149,935 A | 11/2000 | Chiang et al. | |
| 6,153,216 A | 11/2000 | Cordes et al. | |
| 6,165,491 A | 12/2000 | Grasset et al. | |
| 6,165,975 A | 12/2000 | Adams et al. | |
| 6,187,323 B1 | 2/2001 | Aiache et al. | |
| 6,187,339 B1 | 2/2001 | De et al. | |
| 6,190,331 B1 | 2/2001 | Caillouette | |
| 6,201,072 B1 | 3/2001 | Rathi et al. | |
| 6,217,886 B1 | 4/2001 | Önyüksel et al. | |
| 6,225,297 B1 | 5/2001 | Stockemann et al. | |
| 6,227,202 B1 | 5/2001 | Matapurkar | |
| 6,228,383 B1 | 5/2001 | Hansen et al. | |
| 6,228,852 B1 | 5/2001 | Shaak | |
| 6,242,509 B1 | 6/2001 | Berger et al. | |
| 6,245,811 B1 | 6/2001 | Horrobin et al. | |
| 6,248,363 B1 | 6/2001 | Patel et al. | |
| 6,262,115 B1 | 7/2001 | Guittard et al. | |
| 6,264,980 B1 | 7/2001 | Hille | |
| 6,267,984 B1 | 7/2001 | Beste et al. | |
| 6,267,985 B1 | 7/2001 | Chen et al. | |
| 6,274,165 B1 | 8/2001 | Meconi et al. | |
| 6,277,418 B1 | 8/2001 | Markaverich et al. | |
| 6,283,927 B1 | 9/2001 | Caillouette | |
| 6,287,588 B1 | 9/2001 | Shih et al. | |
| 6,287,693 B1 | 9/2001 | Savoir et al. | |
| 6,294,188 B1 | 9/2001 | Ragavan et al. | |
| 6,294,192 B1 * | 9/2001 | Patel | A61K 9/4808 424/450 |
| 6,294,550 B1 | 9/2001 | Place et al. | |
| 6,299,900 B1 | 10/2001 | Reed et al. | |
| 6,303,132 B1 | 10/2001 | Nelson | |
| 6,303,588 B1 | 10/2001 | Danielov | |
| 6,306,841 B1 | 10/2001 | Place et al. | |
| 6,306,914 B1 | 10/2001 | De et al. | |
| 6,309,663 B1 | 10/2001 | Patel et al. | |
| 6,309,669 B1 | 10/2001 | Setterstrom et al. | |
| 6,309,848 B1 | 10/2001 | Howett et al. | |
| 6,312,703 B1 | 11/2001 | Orthoefer | |
| 6,328,987 B1 | 12/2001 | Marini | |
| 6,342,491 B1 | 1/2002 | Dey et al. | |
| 6,344,211 B1 | 2/2002 | Hille | |
| 6,372,209 B1 | 4/2002 | Chrisope | |
| 6,372,245 B1 | 4/2002 | Bowman et al. | |
| 6,372,246 B1 | 4/2002 | Wei et al. | |
| 6,387,390 B1 | 5/2002 | Deaver et al. | |
| 6,402,705 B1 | 6/2002 | Caillouette | |
| 6,416,740 B1 | 7/2002 | Unger | |
| 6,416,778 B1 | 7/2002 | Ragavan et al. | |
| 6,420,352 B1 | 7/2002 | Knowles | |
| 6,423,039 B1 | 7/2002 | Rathbone et al. | |
| 6,423,683 B1 | 7/2002 | Heaton et al. | |
| 6,432,438 B1 | 8/2002 | Shukla | |
| 6,436,633 B1 | 8/2002 | Kreider et al. | |
| 6,440,454 B1 | 8/2002 | Santoro et al. | |
| 6,444,224 B1 | 9/2002 | Rathbone et al. | |
| 6,444,234 B1 | 9/2002 | Kirby et al. | |
| 6,451,300 B1 | 9/2002 | Dunlop et al. | |
| 6,451,339 B2 | 9/2002 | Patel et al. | |
| 6,451,779 B1 | 9/2002 | Hesch | |
| 6,455,246 B1 | 9/2002 | Howett et al. | |
| 6,455,517 B1 | 9/2002 | Tanabe et al. | |
| 6,465,004 B1 | 10/2002 | Rossi-Montero et al. | |
| 6,465,005 B1 | 10/2002 | Biali et al. | |
| 6,465,006 B1 | 10/2002 | Zhang et al. | |
| 6,468,526 B2 | 10/2002 | Chrisope | |
| 6,469,016 B1 | 10/2002 | Place et al. | |
| 6,472,434 B1 | 10/2002 | Place et al. | |
| 6,479,232 B1 | 11/2002 | Howett et al. | |
| 6,495,160 B2 | 12/2002 | Esposito et al. | |
| 6,500,814 B1 | 12/2002 | Hesch | |
| 6,503,896 B1 | 1/2003 | Tanabe et al. | |
| 6,511,969 B1 | 1/2003 | Hermsmeyer | |
| 6,521,250 B2 | 2/2003 | Meconi et al. | |
| 6,526,980 B1 | 3/2003 | Tracy et al. | |
| 6,528,094 B1 | 3/2003 | Savoir et al. | |
| 6,531,139 B1 | 3/2003 | Gao et al. | |
| 6,531,149 B1 | 3/2003 | Kirstgen et al. | |
| 6,537,580 B1 | 3/2003 | Savoir et al. | |
| 6,538,039 B2 | 3/2003 | Laurent | |
| 6,544,196 B2 | 4/2003 | Caillouette | |
| 6,544,553 B1 | 4/2003 | Hsia et al. | |
| 6,548,053 B1 | 4/2003 | Stewart et al. | |
| 6,548,491 B2 | 4/2003 | Tanabe et al. | |
| 6,551,611 B2 | 4/2003 | Elliesen et al. | |
| 6,555,131 B1 | 4/2003 | Wolff et al. | |
| 6,562,367 B1 | 5/2003 | Wolff et al. | |
| 6,562,370 B2 | 5/2003 | Luo et al. | |
| 6,562,790 B2 | 5/2003 | Chein et al. | |
| 6,569,463 B2 | 5/2003 | Patel et al. | |
| 6,583,129 B1 | 6/2003 | Mazer et al. | |
| 6,586,006 B2 | 7/2003 | Roser et al. | |
| 6,589,549 B2 | 7/2003 | Shih et al. | |
| 6,593,317 B1 | 7/2003 | De et al. | |
| 6,599,519 B1 | 7/2003 | Seo et al. | |
| 6,599,962 B2 | 7/2003 | McCleskey et al. | |
| 6,610,652 B2 | 8/2003 | Heaton et al. | |
| 6,610,670 B2 | 8/2003 | Backensfeld et al. | |
| 6,610,674 B1 | 8/2003 | Schreiber | |
| 6,623,761 B2 | 9/2003 | Hassan | |
| 6,635,274 B1 | 10/2003 | Masiz et al. | |
| 6,635,283 B2 | 10/2003 | Edwards et al. | |
| 6,638,528 B1 | 10/2003 | Kanios | |
| 6,638,536 B2 | 10/2003 | Savoir et al. | |
| 6,645,528 B1 | 11/2003 | Straub et al. | |
| 6,649,155 B1 | 11/2003 | Dunlop et al. | |
| 6,653,298 B2 | 11/2003 | Potter et al. | |
| 6,656,929 B1 | 12/2003 | Agnus et al. | |
| 6,660,726 B2 | 12/2003 | Hill et al. | |
| 6,663,608 B2 | 12/2003 | Rathbone et al. | |
| 6,663,895 B2 | 12/2003 | Savoir et al. | |
| 6,682,757 B1 | 1/2004 | Wright | |
| 6,692,763 B1 | 2/2004 | Cummings et al. | |
| 6,708,822 B1 | 3/2004 | Muni | |
| 6,720,001 B2 | 4/2004 | Chen et al. | |
| 6,737,081 B2 | 5/2004 | Savoir et al. | |
| 6,740,333 B2 | 5/2004 | Beckett et al. | |
| 6,743,448 B2 | 6/2004 | Kryger | |
| 6,743,815 B2 | 6/2004 | Huebner et al. | |
| 6,747,018 B2 | 6/2004 | Tanabe et al. | |
| 6,750,291 B2 | 6/2004 | Kim et al. | |
| 6,756,208 B2 | 6/2004 | Griffin et al. | |
| 6,776,164 B2 | 8/2004 | Bunt et al. | |
| 6,787,152 B2 | 9/2004 | Kirby et al. | |
| 6,805,877 B2 | 10/2004 | Massara et al. | |
| 6,809,085 B1 | 10/2004 | Elson et al. | |
| 6,818,226 B2 | 11/2004 | Reed et al. | |
| 6,821,524 B2 | 11/2004 | Marini | |
| 6,841,716 B1 | 1/2005 | Tsutsumi | |
| 6,844,334 B2 | 1/2005 | Hill et al. | |
| 6,855,703 B1 | 2/2005 | Hill et al. | |
| 6,860,859 B2 | 3/2005 | Mehrotra et al. | |
| 6,866,865 B2 | 3/2005 | Hsia et al. | |
| 6,869,969 B2 | 3/2005 | Huebner et al. | |
| 6,878,518 B2 | 4/2005 | Whitehead | |
| 6,901,278 B1 | 5/2005 | Notelovitz | |
| 6,905,705 B2 | 6/2005 | Palm et al. | |
| 6,911,211 B2 | 6/2005 | Eini et al. | |
| 6,911,438 B2 | 6/2005 | Wright | |
| 6,923,988 B2 | 8/2005 | Patel et al. | |
| 6,924,274 B2 | 8/2005 | Lardy et al. | |
| 6,932,983 B1 | 8/2005 | Straub et al. | |
| 6,939,558 B2 | 9/2005 | Massara et al. | |
| 6,943,021 B2 | 9/2005 | Klausner et al. | |
| 6,958,327 B1 | 10/2005 | Hillisch et al. | |
| 6,960,337 B2 | 11/2005 | Daniels et al. | |
| 6,962,691 B1 | 11/2005 | Lulla et al. | |

(56) References Cited

U.S. PATENT DOCUMENTS

| | | |
|---|---|---|
| 6,962,908 B2 | 11/2005 | Aloba et al. |
| 6,967,194 B1 | 11/2005 | Matsuo et al. |
| 6,974,569 B2 | 12/2005 | Dunlop et al. |
| 6,977,250 B2 | 12/2005 | Rodriguez |
| 6,978,945 B2 | 12/2005 | Wong et al. |
| 6,994,862 B2 | 2/2006 | Jeong et al. |
| 6,995,149 B1 | 2/2006 | Endrikat et al. |
| 7,004,321 B1 | 2/2006 | Palm et al. |
| 7,005,429 B2 | 2/2006 | Dey et al. |
| 7,011,846 B2 | 3/2006 | Shojaei et al. |
| 7,018,992 B2 | 3/2006 | Koch et al. |
| 7,030,104 B2 | 4/2006 | Gray et al. |
| 7,030,157 B2 | 4/2006 | Ke et al. |
| RE39,104 E | 5/2006 | Duclos et al. |
| 7,074,779 B2 | 7/2006 | Sui et al. |
| 7,083,590 B1 | 8/2006 | Bunt et al. |
| 7,091,213 B2 | 8/2006 | Metcalf et al. |
| 7,094,228 B2 | 8/2006 | Zhang et al. |
| 7,097,853 B1 | 8/2006 | Garbe et al. |
| 7,101,342 B1 | 9/2006 | Caillouette |
| 7,105,573 B2 | 9/2006 | Krajcik et al. |
| 7,135,190 B2 | 11/2006 | Piao et al. |
| 7,153,522 B1 | 12/2006 | Ikeura et al. |
| 7,163,681 B2 | 1/2007 | Giles-Komar et al. |
| 7,163,699 B2 | 1/2007 | Besse |
| 7,175,850 B2 | 2/2007 | Cevc |
| 7,179,799 B2 | 2/2007 | Hill et al. |
| 7,196,074 B2 | 3/2007 | Blye et al. |
| 7,198,800 B1 | 4/2007 | Ko |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters et al. |
| 7,381,427 B2 | 6/2008 | Ancira et al. |
| 7,387,789 B2 | 6/2008 | Klose et al. |
| 7,388,006 B2 | 6/2008 | Schmees et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B2 | 10/2008 | Besins et al. |
| 7,456,159 B2 | 11/2008 | Houze et al. |
| 7,459,445 B2 | 12/2008 | Hill et al. |
| 7,465,587 B2 | 12/2008 | Imrich et al. |
| 7,470,433 B2 | 12/2008 | Carrara et al. |
| 7,485,666 B2 | 2/2009 | Villanueva et al. |
| 7,497,855 B2 | 3/2009 | Ausiello et al. |
| 7,498,303 B2 | 3/2009 | Arnold et al. |
| 7,534,765 B2 | 5/2009 | Gregg et al. |
| 7,534,780 B2 | 5/2009 | Wyrwa et al. |
| 7,550,142 B2 | 6/2009 | Giles-Komar et al. |
| 7,563,565 B1 | 7/2009 | Matsuo et al. |
| 7,569,274 B2 | 8/2009 | Besse et al. |
| 7,572,779 B2 | 8/2009 | Aloba et al. |
| 7,572,780 B2 | 8/2009 | Hermsmeyer |
| 7,589,082 B2 | 9/2009 | Savoir et al. |
| 7,615,547 B2 | 11/2009 | Reiner |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,799,769 B2 | 9/2010 | White et al. |
| 7,815,936 B2 | 10/2010 | Hasenzahl et al. |
| 7,815,949 B2 | 10/2010 | Cohen |
| 7,829,115 B2 | 11/2010 | Besins et al. |
| 7,829,116 B2 | 11/2010 | Griswold et al. |
| RE42,012 E | 12/2010 | Deaver et al. |
| 7,850,992 B2 | 12/2010 | Kim et al. |
| 7,854,753 B2 | 12/2010 | Kraft et al. |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,871,643 B2 | 1/2011 | Lizio et al. |
| 7,879,830 B2 | 2/2011 | Wiley |
| 7,884,093 B2 | 2/2011 | Creasy et al. |
| 7,925,519 B2 | 4/2011 | Greene |
| 7,939,104 B2 | 5/2011 | Barbera et al. |
| 7,943,602 B2 | 5/2011 | Bunschoten et al. |
| 7,943,604 B2 | 5/2011 | Coelingh et al. |
| 7,945,459 B2 | 5/2011 | Grace et al. |
| 7,960,368 B2 | 6/2011 | Nickisch et al. |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,017 B2 | 11/2011 | Xu |
| 8,048,869 B2 | 11/2011 | Bunschoten et al. |
| 8,063,030 B2 | 11/2011 | Ellman |
| 8,071,576 B2 | 12/2011 | Coelingh et al. |
| 8,071,729 B2 | 12/2011 | Giles-Komar et al. |
| 8,075,916 B2 | 12/2011 | Song et al. |
| 8,075,917 B2 | 12/2011 | Chung et al. |
| 8,076,317 B2 | 12/2011 | Kulmann |
| 8,076,319 B2 | 12/2011 | Leonard |
| 8,080,553 B2 | 12/2011 | Keith et al. |
| 8,088,605 B2 | 1/2012 | Beaudet et al. |
| 8,096,940 B2 | 1/2012 | Josephson et al. |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker et al. |
| 8,119,741 B2 | 2/2012 | Pavlin |
| 8,121,886 B2 | 2/2012 | Azar |
| 8,124,118 B2 | 2/2012 | Lennernas et al. |
| 8,124,595 B2 | 2/2012 | Boissonneault |
| 8,147,561 B2 | 4/2012 | Binmoeller |
| 8,148,546 B2 | 4/2012 | Schuster et al. |
| 8,158,613 B2 | 4/2012 | Staniforth et al. |
| 8,158,614 B2 | 4/2012 | Lambert et al. |
| 8,163,722 B2 | 4/2012 | Savoir et al. |
| 8,177,449 B2 | 5/2012 | Bayly et al. |
| 8,182,833 B2 | 5/2012 | Hermsmeyer |
| 8,187,615 B2 | 5/2012 | Friedman |
| 8,195,403 B2 | 6/2012 | Ishikawa et al. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Theone et al. |
| 8,222,237 B2 | 7/2012 | Nickisch et al. |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack et al. |
| 8,257,725 B2 | 9/2012 | Cromack et al. |
| 8,268,352 B2 | 9/2012 | Vaya et al. |
| 8,268,806 B2 | 9/2012 | Labrie |
| 8,268,878 B2 | 9/2012 | Armer et al. |
| 8,273,730 B2 | 9/2012 | Fernandez et al. |
| 8,287,888 B2 | 10/2012 | Song et al. |
| 8,288,366 B2 | 10/2012 | Chochinov et al. |
| 8,318,898 B2 | 11/2012 | Fasel et al. |
| 8,324,193 B2 | 12/2012 | Lee-Sepsick et al. |
| 8,329,680 B2 | 12/2012 | Evans et al. |
| 8,337,814 B2 | 12/2012 | Osbakken et al. |
| 8,344,007 B2 | 1/2013 | Tang et al. |
| 8,349,820 B2 | 1/2013 | Zeun et al. |
| 8,353,863 B2 | 1/2013 | Imran |
| 8,357,723 B2 | 1/2013 | Satyam |

(56) References Cited

U.S. PATENT DOCUMENTS

| | | |
|---|---|---|
| 8,361,995 B2 | 1/2013 | Schramm |
| 8,362,091 B2 | 1/2013 | Tamarkin et al. |
| 8,372,424 B2 | 2/2013 | Berry et al. |
| 8,372,806 B2 | 2/2013 | Bohler et al. |
| 8,377,482 B2 | 2/2013 | Laurie et al. |
| 8,377,994 B2 | 2/2013 | Gray et al. |
| 8,394,759 B2 | 3/2013 | Barathur et al. |
| 8,415,332 B2 | 4/2013 | Diliberti et al. |
| 8,420,111 B2 | 4/2013 | Hermsmeyer |
| 8,435,561 B2 | 5/2013 | Besins et al. |
| 8,435,972 B2 | 5/2013 | Stein et al. |
| 8,449,879 B2 | 5/2013 | Laurent-Applegate et al. |
| 8,450,108 B2 | 5/2013 | Boyce |
| 8,454,945 B2 | 6/2013 | McCook et al. |
| 8,455,468 B2 | 6/2013 | Hoffman et al. |
| 8,461,138 B2 | 6/2013 | Boissonneault |
| 8,476,252 B2 | 7/2013 | Achleitner et al. |
| 8,481,488 B2 | 7/2013 | Carter |
| 8,486,374 B2 | 7/2013 | Tamarkin et al. |
| 8,486,442 B2 | 7/2013 | Matsushita et al. |
| 8,492,368 B2 | 7/2013 | Vanlandingham et al. |
| 8,507,467 B2 | 8/2013 | Matsui et al. |
| 8,512,693 B2 | 8/2013 | Capito et al. |
| 8,512,754 B2 | 8/2013 | Needham |
| 8,518,376 B2 | 8/2013 | Tamarkin et al. |
| 8,536,159 B2 | 9/2013 | Li et al. |
| 8,540,967 B2 | 9/2013 | Barrett et al. |
| 8,541,400 B2 | 9/2013 | Johnsson et al. |
| 8,551,462 B2 | 10/2013 | Goldstein et al. |
| 8,557,281 B2 | 10/2013 | Halliday et al. |
| 8,568,374 B2 | 10/2013 | De et al. |
| 8,591,951 B2 | 11/2013 | Kohn et al. |
| 8,592,490 B2 | 11/2013 | Legen et al. |
| 8,613,951 B2 | 12/2013 | Zale et al. |
| 8,633,178 B2 | 1/2014 | Bernick et al. |
| 8,633,180 B2 | 1/2014 | Li et al. |
| 8,636,787 B2 | 1/2014 | Sabaria |
| 8,636,982 B2 | 1/2014 | Tamarkin et al. |
| 8,653,129 B2 | 2/2014 | Fein et al. |
| 8,658,627 B2 | 2/2014 | Voskuhl |
| 8,658,628 B2 | 2/2014 | Baucom |
| 8,663,681 B2 | 3/2014 | Ahmed et al. |
| 8,663,692 B1 | 3/2014 | Mueller et al. |
| 8,663,703 B2 | 3/2014 | Lerner et al. |
| 8,664,207 B2 | 3/2014 | Li et al. |
| 8,669,293 B2 | 3/2014 | Levy et al. |
| 8,679,552 B2 | 3/2014 | Guthery |
| 8,694,358 B2 | 4/2014 | Tryfon |
| 8,697,127 B2 | 4/2014 | Sah |
| 8,697,710 B2 | 4/2014 | Li et al. |
| 8,703,105 B2 | 4/2014 | Tamarkin et al. |
| 8,703,179 B2 | 4/2014 | Boga et al. |
| 8,709,385 B2 | 4/2014 | Tamarkin et al. |
| 8,709,451 B2 | 4/2014 | Rapoport et al. |
| 8,715,735 B2 | 5/2014 | Funke et al. |
| 8,721,331 B2 | 5/2014 | Raghuprasad |
| 8,722,021 B2 | 5/2014 | Friedman et al. |
| 8,734,846 B2 | 5/2014 | Ali et al. |
| 8,735,381 B2 | 5/2014 | Podolski |
| 8,741,336 B2 | 6/2014 | Dipierro et al. |
| 8,741,373 B2 | 6/2014 | Bromley et al. |
| 8,753,661 B2 | 6/2014 | Steinmuller-Nethl et al. |
| 8,784,882 B2 | 7/2014 | Mattern |
| 8,815,261 B2 | 8/2014 | Hanma |
| 8,846,077 B2 | 9/2014 | Dewitt |
| 8,846,648 B2 | 9/2014 | Bernick et al. |
| 8,846,649 B2 | 9/2014 | Bernick et al. |
| 8,933,059 B2 | 1/2015 | Bernick et al. |
| 8,987,237 B2 | 3/2015 | Bernick et al. |
| 8,987,238 B2 | 3/2015 | Bernick et al. |
| 8,993,548 B2 | 3/2015 | Bernick et al. |
| 8,993,549 B2 | 3/2015 | Bernick et al. |
| 9,006,222 B2 | 4/2015 | Bernick et al. |
| 9,012,434 B2 | 4/2015 | Bernick et al. |
| 9,248,136 B2 | 2/2016 | Bernick et al. |
| 2001/0005728 A1 | 6/2001 | Guittard et al. |
| 2001/0009673 A1 | 7/2001 | Lipp et al. |
| 2001/0018072 A1 | 8/2001 | Unger |
| 2001/0021816 A1 | 9/2001 | Caillouette |
| 2001/0023261 A1 | 9/2001 | Ryoo et al. |
| 2001/0027189 A1 | 10/2001 | Bennink et al. |
| 2001/0029357 A1 | 10/2001 | Bunt et al. |
| 2001/0031747 A1 | 10/2001 | Deziegler et al. |
| 2001/0032125 A1 | 10/2001 | Bhan et al. |
| 2001/0034340 A1 | 10/2001 | Pickar |
| 2001/0053383 A1 | 12/2001 | Miranda et al. |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0035070 A1 | 3/2002 | Gardlik et al. |
| 2002/0039594 A1 | 4/2002 | Unger |
| 2002/0058648 A1 | 5/2002 | Hammerly |
| 2002/0058926 A1 | 5/2002 | Rathbone et al. |
| 2002/0064541 A1 | 5/2002 | Lapidot et al. |
| 2002/0076441 A1 | 6/2002 | Shih et al. |
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0119174 A1 | 8/2002 | Gardlik et al. |
| 2002/0119198 A1 | 8/2002 | Gao et al. |
| 2002/0132801 A1 | 9/2002 | Heil et al. |
| 2002/0137749 A1 | 9/2002 | Levinson et al. |
| 2002/0142017 A1 | 10/2002 | Simonnet |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0169205 A1 | 11/2002 | Chwalisz et al. |
| 2002/0173510 A1 | 11/2002 | Levinson et al. |
| 2002/0193356 A1 | 12/2002 | Van et al. |
| 2002/0193758 A1 | 12/2002 | Sandberg |
| 2002/0197286 A1 | 12/2002 | Brandman et al. |
| 2003/0003139 A1 | 1/2003 | Lipp et al. |
| 2003/0004145 A1 | 1/2003 | Leonard |
| 2003/0007994 A1 | 1/2003 | Bunt et al. |
| 2003/0027772 A1 | 2/2003 | Breton |
| 2003/0044434 A1 | 3/2003 | Gao et al. |
| 2003/0044453 A1 | 3/2003 | Dittgen et al. |
| 2003/0049307 A1 | 3/2003 | Gyurik |
| 2003/0064097 A1 | 4/2003 | Patel et al. |
| 2003/0064975 A1 | 4/2003 | Koch et al. |
| 2003/0072760 A1 | 4/2003 | Sirbasku |
| 2003/0073248 A1 | 4/2003 | Roth et al. |
| 2003/0073673 A1 | 4/2003 | Hesch |
| 2003/0077297 A1 | 4/2003 | Chen et al. |
| 2003/0078245 A1 | 4/2003 | Bennink et al. |
| 2003/0091620 A1 | 5/2003 | Fikstad et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0109507 A1 | 6/2003 | Franke et al. |
| 2003/0113268 A1 | 6/2003 | Buenafae et al. |
| 2003/0114420 A1 | 6/2003 | Salvati et al. |
| 2003/0114430 A1 | 6/2003 | Macleod et al. |
| 2003/0124182 A1 | 7/2003 | Shojaei et al. |
| 2003/0124191 A1 | 7/2003 | Besse et al. |
| 2003/0125283 A1 | 7/2003 | Gatenby |
| 2003/0130558 A1 | 7/2003 | Massara et al. |
| 2003/0144258 A1 | 7/2003 | Heil et al. |
| 2003/0157157 A1 | 8/2003 | Luo et al. |
| 2003/0166509 A1 | 9/2003 | Edwards et al. |
| 2003/0170295 A1 | 9/2003 | Kim et al. |
| 2003/0175329 A1 | 9/2003 | Azarnoff et al. |
| 2003/0175333 A1 | 9/2003 | Shefer et al. |
| 2003/0180352 A1 | 9/2003 | Patel et al. |
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Berstein et al. |
| 2003/0224057 A1 | 12/2003 | Martin-Letellier et al. |

(56) References Cited

U.S. PATENT DOCUMENTS

| | | |
|---|---|---|
| 2003/0224059 A1 | 12/2003 | Lerner et al. |
| 2003/0225047 A1 | 12/2003 | Caubel et al. |
| 2003/0225048 A1 | 12/2003 | Caubel et al. |
| 2003/0225050 A1 | 12/2003 | Grawe et al. |
| 2003/0228686 A1 | 12/2003 | Klausner et al. |
| 2003/0229057 A1 | 12/2003 | Caubel et al. |
| 2003/0235596 A1 | 12/2003 | Gao et al. |
| 2003/0236236 A1 | 12/2003 | Chen et al. |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |
| 2004/0039356 A1 | 2/2004 | Maki et al. |
| 2004/0043043 A1 | 3/2004 | Schlyter et al. |
| 2004/0043943 A1 | 3/2004 | Guittard et al. |
| 2004/0044080 A1 | 3/2004 | Place et al. |
| 2004/0048900 A1 | 3/2004 | Flood |
| 2004/0052824 A1 | 3/2004 | Abou et al. |
| 2004/0073024 A1 | 4/2004 | Metcalf et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright et al. |
| 2004/0089308 A1 | 5/2004 | Welch |
| 2004/0091541 A1 | 5/2004 | Unger |
| 2004/0092494 A9 | 5/2004 | Dudley |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini-Eteve et al. |
| 2004/0115226 A1 | 6/2004 | Li et al. |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari et al. |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Fernandez et al. |
| 2004/0234606 A1 | 11/2004 | Levine et al. |
| 2004/0241219 A1 | 12/2004 | Hille et al. |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Basu et al. |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Morris et al. |
| 2005/0020552 A1 | 1/2005 | Aschkenasy et al. |
| 2005/0021009 A1 | 1/2005 | Massara et al. |
| 2005/0025833 A1 | 2/2005 | Aschkenasy et al. |
| 2005/0031651 A1 | 2/2005 | Gervais et al. |
| 2005/0042173 A1 | 2/2005 | Besse et al. |
| 2005/0042268 A1 | 2/2005 | Aschkenasy et al. |
| 2005/0048116 A1 | 3/2005 | Straub et al. |
| 2005/0054991 A1 | 3/2005 | Tobyn et al. |
| 2005/0079138 A1 | 4/2005 | Chickering et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theobald et al. |
| 2005/0118272 A1 | 6/2005 | Besse et al. |
| 2005/0129756 A1 | 6/2005 | Podhaisky et al. |
| 2005/0147659 A1 | 7/2005 | Carli et al. |
| 2005/0152956 A1 | 7/2005 | Dudley |
| 2005/0153946 A1 | 7/2005 | Hirsh et al. |
| 2005/0164977 A1 | 7/2005 | Coelingh |
| 2005/0182105 A1 | 8/2005 | Nirschl et al. |
| 2005/0186141 A1 | 8/2005 | Gonda et al. |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0209209 A1 | 9/2005 | Koch et al. |
| 2005/0214384 A1 | 9/2005 | Juturu et al. |
| 2005/0220825 A1 | 10/2005 | Funke et al. |
| 2005/0220900 A1 | 10/2005 | Popp et al. |
| 2005/0222106 A1 | 10/2005 | Bracht |
| 2005/0228692 A1 | 10/2005 | Hodgdon |
| 2005/0228718 A1 | 10/2005 | Austin |
| 2005/0238675 A1 | 10/2005 | Li et al. |
| 2005/0239747 A1 | 10/2005 | Yang et al. |
| 2005/0239758 A1 | 10/2005 | Roby |
| 2005/0244360 A1 | 11/2005 | Billoni |
| 2005/0244522 A1 | 11/2005 | Carrara et al. |
| 2005/0245902 A1 | 11/2005 | Cornish et al. |
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 12/2005 | Jorda et al. |
| 2005/0266088 A1 | 12/2005 | Hinrichs et al. |
| 2005/0271597 A1 | 12/2005 | Keith |
| 2005/0271598 A1 | 12/2005 | Friedman et al. |
| 2005/0272685 A1 | 12/2005 | Hung |
| 2005/0272712 A1 | 12/2005 | Grubb et al. |
| 2006/0009428 A1 | 1/2006 | Grubb et al. |
| 2006/0013873 A1 | 1/2006 | Yang et al. |
| 2006/0014728 A1 | 1/2006 | Chwalisz et al. |
| 2006/0018937 A1 | 1/2006 | Friedman et al. |
| 2006/0019978 A1 | 1/2006 | Balog et al. |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0034904 A1 | 2/2006 | Weimann |
| 2006/0051391 A1 | 3/2006 | Dvoskin et al. |
| 2006/0052341 A1 | 3/2006 | Cornish et al. |
| 2006/0069031 A1 | 3/2006 | Loumaye |
| 2006/0073203 A1 | 4/2006 | Ljusberg-Wahren et al. |
| 2006/0078618 A1 | 4/2006 | Constantinides et al. |
| 2006/0083778 A1 | 4/2006 | Allison et al. |
| 2006/0084704 A1 | 4/2006 | Shih et al. |
| 2006/0088580 A1 | 4/2006 | Meconi et al. |
| 2006/0089337 A1 | 4/2006 | Casper et al. |
| 2006/0093557 A1 | 5/2006 | Dickinson et al. |
| 2006/0093678 A1 | 5/2006 | Chickering, III |
| 2006/0100180 A1 | 5/2006 | Nubbemeyer et al. |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121102 A1 | 6/2006 | Chiang |
| 2006/0121626 A1 | 6/2006 | Imrich et al. |
| 2006/0134188 A1 | 6/2006 | Podhaisky et al. |
| 2006/0135619 A1 | 6/2006 | Kick et al. |
| 2006/0165744 A1 | 7/2006 | Jamil et al. |
| 2006/0193789 A1 | 8/2006 | Tamarkin et al. |
| 2006/0194775 A1 | 8/2006 | Tofovic et al. |
| 2006/0204557 A1 | 9/2006 | Gupta et al. |
| 2006/0233743 A1 | 10/2006 | Kelly |
| 2006/0233841 A1 | 10/2006 | Brodbeck et al. |
| 2006/0235037 A1 | 10/2006 | Purandare et al. |
| 2006/0240111 A1 | 10/2006 | Fernandez et al. |
| 2006/0246122 A1 | 11/2006 | Langguth et al. |
| 2006/0247216 A1 | 11/2006 | Haj-Yehia |
| 2006/0247221 A1 | 11/2006 | Coelingh et al. |
| 2006/0251581 A1 | 11/2006 | McIntyre et al. |
| 2006/0252049 A1 | 11/2006 | Shuler et al. |
| 2006/0252738 A1 | 11/2006 | Avelino et al. |
| 2006/0257472 A1 | 11/2006 | Nielsen |
| 2006/0275218 A1 | 12/2006 | Tamarkin et al. |
| 2006/0275360 A1 | 12/2006 | Ahmed et al. |

(56) References Cited

U.S. PATENT DOCUMENTS

| | | |
|---|---|---|
| 2006/0276414 A1 | 12/2006 | Coelingh et al. |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2006/0287301 A1 | 12/2006 | McNair |
| 2006/0292223 A1 | 12/2006 | Woolfson et al. |
| 2007/0004693 A1 | 1/2007 | Woolfson et al. |
| 2007/0004694 A1 | 1/2007 | Woolfson et al. |
| 2007/0009559 A1 | 1/2007 | Li et al. |
| 2007/0009594 A1 | 1/2007 | Grubb et al. |
| 2007/0010550 A1 | 1/2007 | McKenzie |
| 2007/0014839 A1 | 1/2007 | Bracht |
| 2007/0015698 A1 | 1/2007 | Kleinman et al. |
| 2007/0021360 A1 | 1/2007 | Nyce et al. |
| 2007/0027201 A1 | 2/2007 | McComas et al. |
| 2007/0031491 A1 | 2/2007 | Levine et al. |
| 2007/0036831 A1 | 2/2007 | Baker |
| 2007/0037780 A1 | 2/2007 | Ebert et al. |
| 2007/0037782 A1 | 2/2007 | Hibino et al. |
| 2007/0042038 A1 | 2/2007 | Besse |
| 2007/0060589 A1 | 3/2007 | Purandare et al. |
| 2007/0066628 A1 | 3/2007 | Zhang et al. |
| 2007/0066637 A1 | 3/2007 | Zhang et al. |
| 2007/0066675 A1 | 3/2007 | Zhang et al. |
| 2007/0078091 A1 | 4/2007 | Hubler et al. |
| 2007/0088029 A1 | 4/2007 | Balog et al. |
| 2007/0093548 A1 | 4/2007 | Diffendal et al. |
| 2007/0116729 A1 | 5/2007 | Palepu |
| 2007/0116829 A1 | 5/2007 | Prakash et al. |
| 2007/0128263 A1 | 6/2007 | Gargiulo et al. |
| 2007/0148194 A1 | 6/2007 | Amiji et al. |
| 2007/0154533 A1 | 7/2007 | Dudley |
| 2007/0167418 A1 | 7/2007 | Ferguson |
| 2007/0178051 A1 | 8/2007 | Pruitt et al. |
| 2007/0178166 A1 | 8/2007 | Bernstein et al. |
| 2007/0184558 A1 | 8/2007 | Roth et al. |
| 2007/0185068 A1 | 8/2007 | Ferguson et al. |
| 2007/0190022 A1 | 8/2007 | Bacopoulos et al. |
| 2007/0191319 A1 | 8/2007 | Ke et al. |
| 2007/0191599 A1 | 8/2007 | Hill et al. |
| 2007/0196415 A1 | 8/2007 | Chen et al. |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0232574 A1 | 10/2007 | Galey et al. |
| 2007/0238713 A1 | 10/2007 | Gast et al. |
| 2007/0243229 A1 | 10/2007 | Smith et al. |
| 2007/0248658 A1 | 10/2007 | Zurdo et al. |
| 2007/0254858 A1 | 11/2007 | Cronk |
| 2007/0255197 A1 | 11/2007 | Humberstone et al. |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0286819 A1 | 12/2007 | Devries et al. |
| 2007/0287688 A1 | 12/2007 | Chan et al. |
| 2007/0287789 A1 | 12/2007 | Jones et al. |
| 2007/0292359 A1 | 12/2007 | Friedman et al. |
| 2007/0292387 A1 | 12/2007 | Jon et al. |
| 2007/0292461 A1 | 12/2007 | Tamarkin et al. |
| 2007/0292493 A1 | 12/2007 | Brierre |
| 2007/0298089 A1 | 12/2007 | Saeki et al. |
| 2008/0026035 A1 | 1/2008 | Chollet et al. |
| 2008/0026040 A1 | 1/2008 | Farr et al. |
| 2008/0026062 A1 | 1/2008 | Farr et al. |
| 2008/0038219 A1 | 2/2008 | Mosbaugh et al. |
| 2008/0038350 A1 | 2/2008 | Gerecke et al. |
| 2008/0039405 A1 | 2/2008 | Langley et al. |
| 2008/0050317 A1 | 2/2008 | Tamarkin et al. |
| 2008/0051351 A1 | 2/2008 | Ghisalberti |
| 2008/0063607 A1 | 3/2008 | Tamarkin et al. |
| 2008/0069779 A1 | 3/2008 | Tamarkin et al. |
| 2008/0069791 A1 | 3/2008 | Beissert |
| 2008/0085877 A1 | 4/2008 | Bortz |
| 2008/0095831 A1 | 4/2008 | Mc |
| 2008/0095838 A1 | 4/2008 | Abou |
| 2008/0102127 A1 | 5/2008 | Gao et al. |
| 2008/0113953 A1 | 5/2008 | De et al. |
| 2008/0114050 A1 | 5/2008 | Fensome et al. |
| 2008/0119537 A1 | 5/2008 | Zhang et al. |
| 2008/0125402 A1 | 5/2008 | Diliberti et al. |
| 2008/0138379 A1 | 6/2008 | Jennings-Spring |
| 2008/0138390 A1 | 6/2008 | Hsu et al. |
| 2008/0139392 A1 | 6/2008 | Acosta-Zara et al. |
| 2008/0145423 A1 | 6/2008 | Khan et al. |
| 2008/0153789 A1 | 6/2008 | Dmowski et al. |
| 2008/0175814 A1 | 7/2008 | Phiasivongsa et al. |
| 2008/0175905 A1 | 7/2008 | Liu et al. |
| 2008/0175908 A1 | 7/2008 | Liu et al. |
| 2008/0188829 A1 | 8/2008 | Creasy et al. |
| 2008/0206156 A1 | 8/2008 | Cronk |
| 2008/0206159 A1 | 8/2008 | Tamarkin et al. |
| 2008/0206161 A1 | 8/2008 | Tamarkin et al. |
| 2008/0214512 A1 | 9/2008 | Seitz et al. |
| 2008/0220069 A1 | 9/2008 | Allison |
| 2008/0226698 A1 | 9/2008 | Tang et al. |
| 2008/0227763 A1 | 9/2008 | Lanquetin et al. |
| 2008/0234199 A1 | 9/2008 | Katamreddy |
| 2008/0234240 A1 | 9/2008 | Duesterberg et al. |
| 2008/0255078 A1 | 10/2008 | Katamreddy |
| 2008/0255089 A1 | 10/2008 | Katamreddy |
| 2008/0261931 A1 | 10/2008 | Hedner et al. |
| 2008/0299220 A1 | 12/2008 | Tamarkin et al. |
| 2008/0306036 A1 | 12/2008 | Katamreddy |
| 2008/0312197 A1 | 12/2008 | Rodriguez |
| 2008/0312198 A1 | 12/2008 | Rodriguez |
| 2008/0319078 A1 | 12/2008 | Katamreddy |
| 2009/0004246 A1 | 1/2009 | Woolfson et al. |
| 2009/0010968 A1 | 1/2009 | Allart et al. |
| 2009/0011041 A1 | 1/2009 | Musaeva et al. |
| 2009/0017120 A1 | 1/2009 | Trimble et al. |
| 2009/0022683 A1 | 1/2009 | Song et al. |
| 2009/0047357 A1 | 2/2009 | Tomohira et al. |
| 2009/0053294 A1 | 2/2009 | Prendergast |
| 2009/0060982 A1 | 3/2009 | Ron et al. |
| 2009/0060997 A1 | 3/2009 | Seitz et al. |
| 2009/0068118 A1 | 3/2009 | Eini et al. |
| 2009/0074859 A1 | 3/2009 | Patel |
| 2009/0081206 A1 | 3/2009 | Leibovitz |
| 2009/0081278 A1 | 3/2009 | De et al. |
| 2009/0081303 A1 | 3/2009 | Savoir et al. |
| 2009/0088393 A1 | 4/2009 | Spilburg |
| 2009/0092656 A1 | 4/2009 | Klamerus et al. |
| 2009/0093440 A1 | 4/2009 | Murad |
| 2009/0098069 A1 | 4/2009 | Vacca |
| 2009/0099106 A1 | 4/2009 | Phiasivongsa et al. |
| 2009/0099149 A1 | 4/2009 | Liu et al. |
| 2009/0130029 A1 | 5/2009 | Tamarkin et al. |
| 2009/0131385 A1 | 5/2009 | Voskuhl |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0164341 A1 | 6/2009 | Sunvold et al. |
| 2009/0175799 A1 | 7/2009 | Tamarkin et al. |
| 2009/0181088 A1 | 7/2009 | Song et al. |
| 2009/0186081 A1 | 7/2009 | Holm et al. |
| 2009/0197843 A1 | 8/2009 | Notelovitz et al. |
| 2009/0203658 A1 | 8/2009 | Marx et al. |
| 2009/0214474 A1 | 8/2009 | Jennings |
| 2009/0227025 A1 | 9/2009 | Nichols et al. |
| 2009/0227550 A1 | 9/2009 | Mattern |
| 2009/0232897 A1 | 9/2009 | Sahoo et al. |
| 2009/0258096 A1 | 10/2009 | Cohen |
| 2009/0264395 A1 | 10/2009 | Creasy et al. |
| 2009/0269403 A1 | 10/2009 | Shaked et al. |
| 2009/0285772 A1 | 11/2009 | Phiasivongsa et al. |
| 2009/0285869 A1 | 11/2009 | Trimble |
| 2009/0318558 A1 | 12/2009 | Kim et al. |
| 2009/0324714 A1 | 12/2009 | Liu et al. |
| 2009/0325916 A1 | 12/2009 | Zhang et al. |
| 2010/0008985 A1 | 1/2010 | Pellikaan et al. |
| 2010/0028360 A1 | 2/2010 | Atwood |
| 2010/0034838 A1 | 2/2010 | Staniforth et al. |
| 2010/0034880 A1 | 2/2010 | Sintov et al. |
| 2010/0040671 A1 | 2/2010 | Ahmed et al. |

(56) References Cited

U.S. PATENT DOCUMENTS

| | | |
|---|---|---|
| 2010/0048523 A1 | 2/2010 | Bachman et al. |
| 2010/0055138 A1 | 3/2010 | Margulies et al. |
| 2010/0062067 A1 | 3/2010 | Tonge et al. |
| 2010/0074959 A1 | 3/2010 | Hansom et al. |
| 2010/0086501 A1 | 4/2010 | Chang et al. |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0119585 A1 | 5/2010 | Hille et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0143420 A1 | 6/2010 | Shenoy et al. |
| 2010/0143481 A1 | 6/2010 | Shenoy et al. |
| 2010/0150993 A1 | 6/2010 | Theobald et al. |
| 2010/0151010 A1 | 6/2010 | Petereit et al. |
| 2010/0152144 A1 | 6/2010 | Hermsmeyer |
| 2010/0168228 A1 | 7/2010 | Bose et al. |
| 2010/0183723 A1 | 7/2010 | Laurent-Applegate et al. |
| 2010/0184736 A1 | 7/2010 | Coelingh et al. |
| 2010/0190758 A1 | 7/2010 | Fauser et al. |
| 2010/0204326 A1 | 8/2010 | D'Souza |
| 2010/0210994 A1 | 8/2010 | Zarif |
| 2010/0221195 A1 | 9/2010 | Tamarkin et al. |
| 2010/0227797 A1 | 9/2010 | Axelson et al. |
| 2010/0240626 A1 | 9/2010 | Kulkarni et al. |
| 2010/0247482 A1 | 9/2010 | Cui et al. |
| 2010/0247632 A1 | 9/2010 | Dong et al. |
| 2010/0247635 A1 | 9/2010 | Rosenberg et al. |
| 2010/0255085 A1 | 10/2010 | Liu et al. |
| 2010/0272779 A1 | 10/2010 | Jackson |
| 2010/0273730 A1 | 10/2010 | Hsu et al. |
| 2010/0278759 A1 | 11/2010 | Murad |
| 2010/0279988 A1 | 11/2010 | Setiawan et al. |
| 2010/0291191 A1 | 11/2010 | Shoichet et al. |
| 2010/0292199 A1 | 11/2010 | Leverd et al. |
| 2010/0303825 A9 | 12/2010 | Sirbasku |
| 2010/0312137 A1 | 12/2010 | Gilmour et al. |
| 2010/0316724 A1 | 12/2010 | Whitfield et al. |
| 2010/0322884 A1 | 12/2010 | Dipietro et al. |
| 2010/0330168 A1 | 12/2010 | Gicquel et al. |
| 2011/0014296 A1 | 1/2011 | Chen et al. |
| 2011/0028439 A1 | 2/2011 | Witt-Enderby et al. |
| 2011/0039814 A1 | 2/2011 | Huatan et al. |
| 2011/0053845 A1 | 3/2011 | Levine et al. |
| 2011/0066473 A1 | 3/2011 | Bernick et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0087192 A1 | 4/2011 | Uhland et al. |
| 2011/0091555 A1 | 4/2011 | De et al. |
| 2011/0098258 A1 | 4/2011 | Masini-Eteve et al. |
| 2011/0098631 A1 | 4/2011 | McIntyre et al. |
| 2011/0104268 A1 | 5/2011 | Pachot et al. |
| 2011/0104289 A1 | 5/2011 | Savoir et al. |
| 2011/0130372 A1 | 6/2011 | Agostinacchio et al. |
| 2011/0135719 A1 | 6/2011 | Besins et al. |
| 2011/0137057 A1 | 6/2011 | Frincke |
| 2011/0142914 A1 | 6/2011 | Persaud et al. |
| 2011/0142945 A1 | 6/2011 | Chen et al. |
| 2011/0152840 A1 | 6/2011 | Lee et al. |
| 2011/0158920 A1 | 6/2011 | Morley et al. |
| 2011/0171140 A1 | 7/2011 | Illum et al. |
| 2011/0182997 A1 | 7/2011 | Lewis et al. |
| 2011/0190201 A1 | 8/2011 | Hyde et al. |
| 2011/0195031 A1 | 8/2011 | Du |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0238003 A1 | 9/2011 | Bruno-Raimondi et al. |
| 2011/0244043 A1 | 10/2011 | Xu et al. |
| 2011/0250256 A1 | 10/2011 | Hyun-Oh et al. |
| 2011/0250259 A1 | 10/2011 | Buckman |
| 2011/0250274 A1 | 10/2011 | Shaked et al. |
| 2011/0256092 A1 | 10/2011 | Phiasivongsa et al. |
| 2011/0262373 A1 | 10/2011 | Umbert |
| 2011/0262494 A1 | 10/2011 | Achleitner et al. |
| 2011/0268665 A1 | 11/2011 | Tamarkin et al. |
| 2011/0275584 A1 | 11/2011 | Wilckens et al. |
| 2011/0281832 A1 | 11/2011 | Li et al. |
| 2011/0287094 A1 | 11/2011 | Penhasi et al. |
| 2011/0293720 A1 | 12/2011 | General et al. |
| 2011/0294738 A1 | 12/2011 | Ren et al. |
| 2011/0300167 A1 | 12/2011 | McMurry et al. |
| 2011/0301087 A1 | 12/2011 | McBride et al. |
| 2011/0306579 A1 | 12/2011 | Stein |
| 2011/0311592 A1 | 12/2011 | Birbara |
| 2011/0312927 A1 | 12/2011 | Nachaegari et al. |
| 2011/0312928 A1 | 12/2011 | Nachaegari et al. |
| 2011/0318405 A1 | 12/2011 | Erwin |
| 2011/0318431 A1 | 12/2011 | Gulati |
| 2012/0009276 A1 | 1/2012 | De |
| 2012/0015350 A1 | 1/2012 | Nabatiyan et al. |
| 2012/0021041 A1 | 1/2012 | Rossi et al. |
| 2012/0028888 A1 | 2/2012 | Janz et al. |
| 2012/0028910 A1 | 2/2012 | Combal et al. |
| 2012/0028936 A1 | 2/2012 | Gloger et al. |
| 2012/0045532 A1 | 2/2012 | Cohen |
| 2012/0046264 A1 | 2/2012 | Simes et al. |
| 2012/0046518 A1 | 2/2012 | Yoakum et al. |
| 2012/0052077 A1 | 3/2012 | Truitt, III et al. |
| 2012/0058171 A1 | 3/2012 | De et al. |
| 2012/0058962 A1 | 3/2012 | Cumming et al. |
| 2012/0058979 A1 | 3/2012 | Keith et al. |
| 2012/0064135 A1 | 3/2012 | Levin et al. |
| 2012/0065179 A1 | 3/2012 | Andersson |
| 2012/0065221 A1 | 3/2012 | Babul |
| 2012/0087872 A1 | 4/2012 | Tamarkin et al. |
| 2012/0101073 A1 | 4/2012 | Mannion et al. |
| 2012/0121517 A1 | 5/2012 | Song et al. |
| 2012/0121692 A1 | 5/2012 | Xu et al. |
| 2012/0122829 A1 | 5/2012 | Taravella et al. |
| 2012/0128625 A1 | 5/2012 | Shalwitz et al. |
| 2012/0128654 A1 | 5/2012 | Terpstra et al. |
| 2012/0128683 A1 | 5/2012 | Shantha |
| 2012/0128733 A1 | 5/2012 | Perrin et al. |
| 2012/0128777 A1 | 5/2012 | Keck et al. |
| 2012/0129773 A1 | 5/2012 | Geier et al. |
| 2012/0129819 A1 | 5/2012 | Vancaillie et al. |
| 2012/0136013 A1 | 5/2012 | Li et al. |
| 2012/0142645 A1 | 6/2012 | Marx |
| 2012/0148670 A1 | 6/2012 | Kim et al. |
| 2012/0149748 A1 | 6/2012 | Shanler et al. |
| 2012/0172343 A1 | 7/2012 | Lindenthal et al. |
| 2012/0184515 A1 | 7/2012 | Klar et al. |
| 2012/0231052 A1 | 9/2012 | Sitruk-Ware et al. |
| 2012/0232011 A1 | 9/2012 | Kneissel et al. |
| 2012/0232042 A1 | 9/2012 | Klar et al. |
| 2012/0263679 A1 | 10/2012 | Marlow et al. |
| 2012/0269721 A1 | 10/2012 | Weng et al. |
| 2012/0269878 A2 | 10/2012 | Cantor et al. |
| 2012/0277249 A1 | 11/2012 | Andersson et al. |
| 2012/0277727 A1 | 11/2012 | Doshi et al. |
| 2012/0283671 A1 | 11/2012 | Shibata et al. |
| 2012/0295911 A1 | 11/2012 | Mannion et al. |
| 2012/0301517 A1 | 11/2012 | Zhang et al. |
| 2012/0301538 A1 | 11/2012 | Gordon-Beresford et al. |
| 2012/0302535 A1 | 11/2012 | Caufriez et al. |
| 2012/0316130 A1 | 12/2012 | Hendrix |
| 2012/0316496 A1 | 12/2012 | Hoffmann et al. |
| 2012/0321579 A1 | 12/2012 | Edelson et al. |
| 2012/0322779 A9 | 12/2012 | Voskuhl |
| 2012/0328549 A1 | 12/2012 | Edelson et al. |
| 2012/0328701 A1 | 12/2012 | Edelson et al. |
| 2012/0329738 A1 | 12/2012 | Liu |
| 2013/0004619 A1 | 1/2013 | Chow et al. |
| 2013/0011342 A1 | 1/2013 | Tamarkin et al. |
| 2013/0017239 A1 | 1/2013 | Viladot et al. |
| 2013/0022674 A1 | 1/2013 | Dudley et al. |
| 2013/0023505 A1 | 1/2013 | Garfield et al. |
| 2013/0023823 A1 | 1/2013 | Simpson et al. |
| 2013/0028850 A1 | 1/2013 | Tamarkin et al. |
| 2013/0029947 A1 | 1/2013 | Nachaegari et al. |

(56) References Cited

U.S. PATENT DOCUMENTS

| | | |
|---|---|---|
| 2013/0029957 A1 | 1/2013 | Giliyar et al. |
| 2013/0045266 A1 | 2/2013 | Choi et al. |
| 2013/0045953 A1 | 2/2013 | Sitruk-Ware et al. |
| 2013/0059795 A1 | 3/2013 | Lo et al. |
| 2013/0064897 A1 | 3/2013 | Binay |
| 2013/0072466 A1 | 3/2013 | Choi et al. |
| 2013/0084257 A1 | 4/2013 | Ishida et al. |
| 2013/0085123 A1 | 4/2013 | Li et al. |
| 2013/0089574 A1 | 4/2013 | Schmidt-Gollwitzer et al. |
| 2013/0090318 A1 | 4/2013 | Ulmann et al. |
| 2013/0102781 A1 | 4/2013 | Bevill et al. |
| 2013/0108551 A1 | 5/2013 | Langereis et al. |
| 2013/0116215 A1 | 5/2013 | Coma et al. |
| 2013/0116222 A1 | 5/2013 | Arnold et al. |
| 2013/0122051 A1 | 5/2013 | Abidi et al. |
| 2013/0123175 A1 | 5/2013 | Hill et al. |
| 2013/0123220 A1 | 5/2013 | Queiroz |
| 2013/0123351 A1 | 5/2013 | Dewitt |
| 2013/0129818 A1 | 5/2013 | Bernick et al. |
| 2013/0131027 A1 | 5/2013 | Pakkalin et al. |
| 2013/0131028 A1 | 5/2013 | Snyder et al. |
| 2013/0131029 A1 | 5/2013 | Bakker et al. |
| 2013/0149314 A1 | 6/2013 | Bullerdiek et al. |
| 2013/0164225 A1 | 6/2013 | Tamarkin et al. |
| 2013/0164346 A1 | 6/2013 | Lee et al. |
| 2013/0165744 A1 | 6/2013 | Carson et al. |
| 2013/0178452 A1 | 7/2013 | King |
| 2013/0183254 A1 | 7/2013 | Zhou et al. |
| 2013/0183325 A1 | 7/2013 | Bottoni et al. |
| 2013/0189193 A1 | 7/2013 | Tamarkin et al. |
| 2013/0189196 A1 | 7/2013 | Tamarkin et al. |
| 2013/0189230 A1 | 7/2013 | Shoichet et al. |
| 2013/0189368 A1 | 7/2013 | Mosqueira et al. |
| 2013/0209539 A1 | 8/2013 | Loxley et al. |
| 2013/0210709 A1 | 8/2013 | McMurry et al. |
| 2013/0216550 A1 | 8/2013 | Penninger et al. |
| 2013/0216596 A1 | 8/2013 | Viladot et al. |
| 2013/0224177 A1 | 8/2013 | Kim et al. |
| 2013/0224257 A1 | 8/2013 | Sah et al. |
| 2013/0224268 A1 | 8/2013 | Alam et al. |
| 2013/0224300 A1 | 8/2013 | Maggio |
| 2013/0225412 A1 | 8/2013 | Sardari et al. |
| 2013/0225542 A1 | 8/2013 | Poegh et al. |
| 2013/0226113 A1 | 8/2013 | Schumacher et al. |
| 2013/0243696 A1 | 9/2013 | Wang et al. |
| 2013/0245253 A1 | 9/2013 | Marx et al. |
| 2013/0245570 A1 | 9/2013 | Jackson |
| 2013/0261096 A1 | 10/2013 | Merian et al. |
| 2013/0266645 A1 | 10/2013 | Becker et al. |
| 2013/0267485 A1 | 10/2013 | Da |
| 2013/0273167 A1 | 10/2013 | Lee et al. |
| 2013/0274211 A1 | 10/2013 | Burman et al. |
| 2013/0280213 A1 | 10/2013 | Voskuhl |
| 2013/0316374 A1 | 11/2013 | Penninger et al. |
| 2013/0317065 A1 | 11/2013 | Tatani et al. |
| 2013/0317315 A1 | 11/2013 | Lu et al. |
| 2013/0324565 A1 | 12/2013 | Li et al. |
| 2013/0331363 A1 | 12/2013 | Li et al. |
| 2013/0338122 A1 | 12/2013 | Bernick et al. |
| 2013/0338123 A1 | 12/2013 | Bernick et al. |
| 2013/0338124 A1 | 12/2013 | Li et al. |
| 2013/0345187 A1 | 12/2013 | Rodriguez |
| 2014/0018335 A1 | 1/2014 | Tatani et al. |
| 2014/0024590 A1 | 1/2014 | Weidhaas et al. |
| 2014/0031289 A1 | 1/2014 | Song et al. |
| 2014/0031323 A1 | 1/2014 | Perez |
| 2014/0066416 A1 | 3/2014 | Leunis et al. |
| 2014/0072531 A1 | 3/2014 | Kim et al. |
| 2014/0079686 A1 | 3/2014 | Barman et al. |
| 2014/0088051 A1 | 3/2014 | Bernick et al. |
| 2014/0088058 A1 | 3/2014 | Maurizio |
| 2014/0088059 A1 | 3/2014 | Perumal et al. |
| 2014/0094426 A1 | 4/2014 | Drummond et al. |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100159 A1 | 4/2014 | Conrad |
| 2014/0100204 A1 | 4/2014 | Bernick et al. |
| 2014/0100205 A1 | 4/2014 | Bernick et al. |
| 2014/0100206 A1 | 4/2014 | Bernick et al. |
| 2014/0113889 A1 | 4/2014 | Connor et al. |
| 2014/0127185 A1 | 5/2014 | Stein et al. |
| 2014/0127280 A1 | 5/2014 | Duesterberg et al. |
| 2014/0127308 A1 | 5/2014 | Opara et al. |
| 2014/0128798 A1 | 5/2014 | Janson et al. |
| 2014/0148491 A1 | 5/2014 | Valia et al. |
| 2014/0186332 A1 | 7/2014 | Ezrin et al. |
| 2014/0187487 A1 | 7/2014 | Shoichet et al. |
| 2014/0193523 A1 | 7/2014 | Henry |
| 2014/0194396 A1 | 7/2014 | Li et al. |
| 2014/0206616 A1 | 7/2014 | Ko et al. |
| 2014/0213565 A1 | 7/2014 | Bernick et al. |
| 2014/0234428 A1 | 8/2014 | Barathur et al. |
| 2014/0271884 A1 | 9/2014 | Prud'Homme et al. |
| 2014/0287027 A1 | 9/2014 | Schiffelers et al. |
| 2014/0288035 A1 | 9/2014 | Hübner et al. |
| 2014/0329783 A1 | 11/2014 | Bernick et al. |
| 2014/0335193 A1 | 11/2014 | Rintoul et al. |
| 2014/0335194 A1 | 11/2014 | Lee et al. |
| 2014/0370084 A1 | 12/2014 | Bernick et al. |
| 2014/0370110 A1 | 12/2014 | Perumal et al. |
| 2014/0371182 A1 | 12/2014 | Bernick et al. |
| 2014/0371183 A1 | 12/2014 | Bernick et al. |
| 2014/0371184 A1 | 12/2014 | Bernick et al. |
| 2014/0371185 A1 | 12/2014 | Bernick et al. |
| 2015/0031654 A1 | 1/2015 | Amadio |
| 2015/0045335 A1 | 2/2015 | Bernick et al. |
| 2015/0118164 A1 | 4/2015 | Tamarkin et al. |
| 2015/0133421 A1 | 5/2015 | Bernick et al. |
| 2015/0148323 A1 | 5/2015 | Cacace et al. |
| 2015/0164812 A1 | 6/2015 | Holm et al. |
| 2015/0202211 A1 | 7/2015 | Amadio et al. |
| 2016/0030449 A1 | 2/2016 | Persicaner et al. |
| 2017/0056418 A1 | 3/2017 | Thorsteinsson et al. |
| 2017/0281645 A1 | 10/2017 | Shadiack et al. |
| 2017/0281646 A1 | 10/2017 | Inskeep et al. |
| 2017/0281647 A1 | 10/2017 | Shadiack et al. |

FOREIGN PATENT DOCUMENTS

| | | |
|---|---|---|
| EP | 0275716 A1 | 7/1988 |
| EP | 0622075 A1 | 11/1994 |
| EP | 0785211 A1 | 7/1997 |
| EP | 0785212 A1 | 7/1997 |
| EP | 0811381 A1 | 12/1997 |
| EP | 1043973 A1 | 10/2000 |
| EP | 0904064 B1 | 10/2001 |
| EP | 0750495 B1 | 12/2002 |
| EP | 1283674 A2 | 2/2003 |
| EP | 0811381 B1 | 5/2003 |
| EP | 0999826 B1 | 5/2004 |
| EP | 1094781 B1 | 7/2008 |
| EP | 2191833 A1 | 6/2010 |
| EP | 2101729 B1 | 3/2011 |
| EP | 1778187 B1 | 5/2012 |
| EP | 2191833 B1 | 2/2013 |
| EP | 2172497 B1 | 5/2013 |
| GB | 452238 A | 8/1936 |
| GB | 720561 A | 12/1954 |
| GB | 848881 A | 9/1960 |
| GB | 874368 A | 8/1961 |
| GB | 1589946 A | 5/1981 |
| GB | 2098865 B | 12/1985 |
| IN | 216026 | 3/2008 |
| IN | /53/KOL/2005 | 9/2009 |
| IN | 244217 | 11/2010 |
| WO | WO-9011064 A1 | 10/1990 |
| WO | WO-9317686 A1 | 9/1993 |
| WO | WO-9422426 A1 | 10/1994 |
| WO | WO-9524893 A1 | 9/1995 |
| WO | WO-9530409 A1 | 11/1995 |
| WO | WO-9609826 A2 | 4/1996 |
| WO | WO-9619975 A1 | 7/1996 |
| WO | WO-9630000 A1 | 10/1996 |

(56) References Cited

FOREIGN PATENT DOCUMENTS

| | | |
|---|---|---|
| WO | WO-9705491 A1 | 2/1997 |
| WO | WO-9740823 A1 | 11/1997 |
| WO | WO-9743989 A1 | 11/1997 |
| WO | WO-9810293 A1 | 3/1998 |
| WO | WO-9832465 A1 | 7/1998 |
| WO | WO-9851280 A1 | 11/1998 |
| WO | WO-9932072 A1 | 7/1999 |
| WO | WO-9932089 A1 | 7/1999 |
| WO | WO-9939700 A1 | 8/1999 |
| WO | WO-9942109 A1 | 8/1999 |
| WO | WO-9943304 A1 | 9/1999 |
| WO | WO-9948477 A1 | 9/1999 |
| WO | WO-9953910 A2 | 10/1999 |
| WO | WO-9963974 A2 | 12/1999 |
| WO | WO-0001351 A1 | 1/2000 |
| WO | WO-0006120 A1 | 2/2000 |
| WO | WO-0006175 A1 | 2/2000 |
| WO | WO-0038659 A1 | 7/2000 |
| WO | WO-0045795 A2 | 8/2000 |
| WO | WO-0050007 A1 | 8/2000 |
| WO | WO-0059577 A1 | 10/2000 |
| WO | WO-0076522 A1 | 12/2000 |
| WO | WO-0137808 A1 | 5/2001 |
| WO | WO-0154699 A1 | 8/2001 |
| WO | WO-0160325 A1 | 8/2001 |
| WO | WO-0207700 A2 | 1/2002 |
| WO | WO-0211768 A1 | 2/2002 |
| WO | WO-0222132 A2 | 3/2002 |
| WO | WO-0240008 A2 | 5/2002 |
| WO | WO-0241878 A2 | 5/2002 |
| WO | WO-02053131 A1 | 7/2002 |
| WO | WO-02078604 A2 | 10/2002 |
| WO | WO-02078602 A3 | 2/2003 |
| WO | WO-03028667 A2 | 4/2003 |
| WO | WO-03041718 A1 | 5/2003 |
| WO | WO-03041741 A1 | 5/2003 |
| WO | WO-03068186 A1 | 8/2003 |
| WO | WO-03077923 A1 | 9/2003 |
| WO | WO-03082254 A1 | 10/2003 |
| WO | WO-03092588 A2 | 11/2003 |
| WO | WO-2004014397 A1 | 2/2004 |
| WO | WO-2004014432 A1 | 2/2004 |
| WO | WO-2004017983 A1 | 3/2004 |
| WO | WO-2004032897 A2 | 4/2004 |
| WO | WO-2004052336 A2 | 6/2004 |
| WO | WO-2004054540 A2 | 7/2004 |
| WO | WO-2004080413 A2 | 9/2004 |
| WO | WO-2005004917 A2 | 1/2005 |
| WO | WO-2005027911 A1 | 3/2005 |
| WO | WO-2005030175 A1 | 4/2005 |
| WO | WO-2005081825 A2 | 9/2005 |
| WO | WO-2005087194 A1 | 9/2005 |
| WO | WO-2005087199 A2 | 9/2005 |
| WO | WO-2005105040 A2 | 11/2005 |
| WO | WO-2005105059 A1 | 11/2005 |
| WO | WO-2005115335 A1 | 12/2005 |
| WO | WO-2005120470 A1 | 12/2005 |
| WO | WO-2005120517 A1 | 12/2005 |
| WO | WO-2006013369 A2 | 2/2006 |
| WO | WO-2006034090 A1 | 3/2006 |
| WO | WO-2006036899 A2 | 4/2006 |
| WO | WO-2006053172 A2 | 5/2006 |
| WO | WO-2006105615 A1 | 10/2006 |
| WO | WO-2006113505 A2 | 10/2006 |
| WO | WO-2006138686 A1 | 12/2006 |
| WO | WO-2006138735 A2 | 12/2006 |
| WO | WO-2007045027 A1 | 4/2007 |
| WO | WO-2007103294 A2 | 9/2007 |
| WO | WO-2006138735 A3 | 10/2007 |
| WO | WO-2007120868 A2 | 10/2007 |
| WO | WO-2007123790 A1 | 11/2007 |
| WO | WO-2007124250 A2 | 11/2007 |
| WO | WO-2007124250 A3 | 12/2007 |
| WO | WO-2007144151 A1 | 12/2007 |
| WO | WO-2007103294 A3 | 4/2008 |
| WO | WO-2008049516 A3 | 6/2008 |
| WO | WO-2008077823 A1 | 7/2008 |
| WO | WO-2008152444 A2 | 12/2008 |
| WO | WO-2009002542 A1 | 12/2008 |
| WO | WO-2009036311 A1 | 3/2009 |
| WO | WO-2009040818 A1 | 4/2009 |
| WO | WO-2008152444 A3 | 6/2009 |
| WO | WO-2009069006 A2 | 6/2009 |
| WO | WO-2009098072 A2 | 8/2009 |
| WO | WO-2009098072 A3 | 10/2009 |
| WO | WO-2009069006 A3 | 11/2009 |
| WO | WO-2009133352 A2 | 11/2009 |
| WO | WO-2010033188 A2 | 3/2010 |
| WO | WO-2009133352 A3 | 10/2010 |
| WO | WO-2010146872 A1 | 12/2010 |
| WO | WO-2011000210 A1 | 1/2011 |
| WO | WO-2011073995 A2 | 6/2011 |
| WO | WO-2011073995 A3 | 8/2011 |
| WO | WO-2010033188 A3 | 9/2011 |
| WO | WO-2011120084 A1 | 10/2011 |
| WO | WO-2011128336 A1 | 10/2011 |
| WO | WO-2012009778 A2 | 1/2012 |
| WO | WO-2012024361 A1 | 2/2012 |
| WO | WO-2012055814 A1 | 5/2012 |
| WO | WO-2012055840 A1 | 5/2012 |
| WO | WO-2012065740 A1 | 5/2012 |
| WO | WO-2012098090 A1 | 7/2012 |
| WO | WO-2012116277 A1 | 8/2012 |
| WO | WO-2012118563 A2 | 9/2012 |
| WO | WO-2012120365 A1 | 9/2012 |
| WO | WO-2012127501 A2 | 9/2012 |
| WO | WO-2012156561 A1 | 11/2012 |
| WO | WO-2012156822 A1 | 11/2012 |
| WO | WO-2012158483 A2 | 11/2012 |
| WO | WO-2012166909 A1 | 12/2012 |
| WO | WO-2012170578 A1 | 12/2012 |
| WO | WO-2013011501 A1 | 1/2013 |
| WO | WO-2012009778 A3 | 2/2013 |
| WO | WO-2013025449 A2 | 2/2013 |
| WO | WO-2013028639 A1 | 2/2013 |
| WO | WO-2013035101 A1 | 3/2013 |
| WO | WO-2013044067 A1 | 3/2013 |
| WO | WO-2013045404 A2 | 4/2013 |
| WO | WO-2013059285 A1 | 4/2013 |
| WO | WO 2013/078422 A2 | 5/2013 |
| WO | WO-2013063279 A1 | 5/2013 |
| WO | WO-2013064620 A1 | 5/2013 |
| WO | WO-2013071281 A1 | 5/2013 |
| WO | WO-2013088254 A1 | 6/2013 |
| WO | WO-2013102665 A1 | 7/2013 |
| WO | WO-2013106437 A1 | 7/2013 |
| WO | WO-2013113690 A1 | 8/2013 |
| WO | WO-2013124415 A1 | 8/2013 |
| WO | WO-2013127727 A1 | 9/2013 |
| WO | WO-2013127728 A1 | 9/2013 |
| WO | WO-2013144356 A1 | 10/2013 |
| WO | WO-2013149258 A2 | 10/2013 |
| WO | WO-2013158454 A2 | 10/2013 |
| WO | WO-2013170052 A1 | 11/2013 |
| WO | WO-2013178587 A1 | 12/2013 |
| WO | WO-2013181449 A1 | 12/2013 |
| WO | WO-2013192248 A1 | 12/2013 |
| WO | WO-2013192249 A1 | 12/2013 |
| WO | WO-2013192250 A1 | 12/2013 |
| WO | WO-2013192251 A1 | 12/2013 |
| WO | WO-2014001904 A1 | 1/2014 |
| WO | WO-2014004424 A1 | 1/2014 |
| WO | WO-2014009434 A1 | 1/2014 |
| WO | WO-2014018569 A1 | 1/2014 |
| WO | WO-2014018570 A1 | 1/2014 |
| WO | WO-2014018571 A2 | 1/2014 |
| WO | WO-2014018856 A1 | 1/2014 |
| WO | WO-2014018932 A2 | 1/2014 |
| WO | WO-2014031958 A1 | 2/2014 |
| WO | WO-2014041120 A1 | 3/2014 |
| WO | WO-2014052792 A1 | 4/2014 |
| WO | WO-2014056897 A1 | 4/2014 |
| WO | WO-2014066442 A2 | 5/2014 |
| WO | WO-2014074846 A1 | 5/2014 |

(56) References Cited

FOREIGN PATENT DOCUMENTS

| WO | WO-2014076231 A1 | 5/2014 |
|---|---|---|
| WO | WO-2014076569 A2 | 5/2014 |
| WO | WO-2014081598 A1 | 5/2014 |
| WO | WO-2014086739 A1 | 6/2014 |
| WO | WO-2014093114 A1 | 6/2014 |
| WO | WO-2014104784 A1 | 7/2014 |
| WO | WO-2014197008 A1 | 12/2014 |

OTHER PUBLICATIONS

Hanson, J.R., "13. Terpenoids and Steroids," *Annual Reports Section B (Organic Chemistry)* 82:353-375, Royal Society of Chemistry, England (1985).

Lauer, A.C., et al., "Evaluation of the Hairless Rat as a Model for in Vivo Percutaneous Absorption," *Journal of Pharmaceutical Sciences* 86(1):13-18, American Chemical Society and American Pharmaceutical Association, United States (1997).

Palamakula, A., et al., "Preparation and In Vitro Characterization of Self-Nanoemulsified Drug Delivery Systems of Coenzyme Q10 Using Chiral Essential Oil Components," Pharmaceutical Technology pp. 74-88, accessed at http://images.alfresco.advanstar.com/alfresco_images/pharma/2014/08/22/97292023-0e75-4736-82d1-df2e08ffd626/article-128365.pdf, accessed on Apr. 25, 2017 (2004).

Tuleu, C., et al., "Comparative Bioavailability Study in Dogs of a Self-Emulsifying Formulation of Progesterone Presented in a Pellet and Liquid Form Compared with an Aqueous Suspension of Progesterone," *Journal of Pharmaceutical Sciences* 93(6):1495-1502, Wiley-Liss, Inc., United States (2004).

CREMER Oleo, "CREMER Care, IMWITOR® 988, INCI: Glyceryl Caprylate," accessed at http://s3.amazonaws.com/petercremerna/products/spec_sheets/448/773/262/original/TDSC_IMWITOR_988_e.pdf?1385268551, accessed on May 23, 2017, 4 pages.

Doren, M., et al., "Effects of Specific Post-menopausal Hormone Therapies on Bone Mineral Density in Post-Menopausal Women: A Meta-Analysis," *Human Reproduction* 18(8):1737-1746, European Society of Human Reproduction and Embryology, England (2003).

International Search Report and Written Opinion for International Application No. PCT/US17/24955, ISA/US, Alexandria, dated Jun. 12, 2017, 11 pages.

Williams, A.C. and Barry, B.W., "The Enhancement Index Concept Applied to Terpene Penetration Enhancers for Human Skin and Model Lipophilic (oestradiol) and Hydrophilic (5-fluorouracil) Drugs," *International Journal of Pharmaceutics* 74(2-3):157-168, Elsevier Science Publishers B.V., Netherlands (1991).

Abbas, M.A., et al., "Regression of Endometrial Implants Treated with Vitamin D3 in a Rat Model of Endometriosis," European Journal of Pharmacology 715(1-3):72-75, Elsevier Science, Netherlands (2013).

Abitec, CapmuiMCM, EP, Technical Data Sheet, version 10, 2014, Columbus, OH.

Abitec, CapmuiMCM, NF, Technical Data Sheet, version 6, 2014, Columbus, OH.

Abitec, CapmuiMCM, Safety Data Sheet, 2011, Janesville, WI.

Abitec, CapmuiMCM, Technical Data Sheet, version 17, 2014, Columbus, OH.

Abitec, CapmuiPG8, CAS No. 31565-12-5, version 11,2006, Columbus, OH.

Abitec Corporation Excipients for the Pharmaceutical Industry—Regulatory and Product Information, 2 pages (2013).

Acarturk, F., "Mucoadhesive Vaginal Drug Delivery Systems," Recent patents on drug delivery & formulation 3(3):193-205, Bentham Science Publishers, United Arab Emirates (2009).

Acog, Mckinlay, et al., "Practice Bulletin, Clinical Management Guidelines for Obstetrician-Gynecologists,", Obstetrics & Gynecology Agog, No. 141, vol. 123(1), 202-216, (2014).

Advisory Action dated Jan. 29, 2007 for U.S. Appl. No. 12/561,515, filed Sep. 17, 2009.

Alabi, K. A., et al., "Analysis of Fatty Acid Composition ofThevetia peruviana and Hura crepitans Seed oils using GC-FID," Fountain Journal of Natural and Applied Sciences 2(2):32-7, Osogbo (2013).

Alexander, KS, Corn Oil, CAS No. 8001-30-7, (2009).

Alvarez, P., et al., "Ectopic Uterine Tissue as a Chronic Pain Generator," Neuroscience 225:269-282, Elsevier Science, United States (2012).

Application Note JASCO CD Spectra of Pharmaceuticals Substances Steroids, 2 pages.

Araya-Sibaja, A.M., et al., "Morphology Study of Progesterone Polymorphs Prepared by Polymer-induced Heteronucleation (Pihn)," Scanning 35(4):213-221, John Wiley & Sons, United States (2013).

Araya-Sibaja, Andrea Manela, et al., "Chemical Properties of Progesterone Selected Refer," SciFinder, American Chemical Society & US National. Library. of Med, (2014).

Araya-Sibaja, Andrea Manela, et al., "Polymorphism in Progesterone," SciFinder, pp. 1-46, American Chemical Society & US National. Library. of Med, (2014).

Araya-Sibaja, Andrea Manela, et al., "Polymorphism in Progesterone Selected References," SciFinder, pp. 1-12, American Chemical Society & US National. Library. of Med, (2014).

Araya-Sibaja., et al., "Crystallization of progesterone polymorphs using polymer-induced heteronucleation (PIHn) method," Drug Development and Industrial Pharmacy, Early Online, pp. 1-8, Informa Healthcare (2014).

Archer, D.F., et al., "Effects of Ospemifene on the Female Reproductive and Urinary Tracts : Translation From Preclinical Models into Clinical Evidence," Menopause, Lippincott-Raven Publishers, United States (2014).

Archer, F., et al., Estrace® vs Premarin® for Treatment of Menopausal Symptoms: Dosage Comparison Study 9(1):21-31, (1992).

Ashburn, A.D., et al., "Cardiovascular , Hepatic and Renal Lesions in Mice Receiving Cortisone , Estrone and Progesterone," The Yale Journal of Biology and Medicine 35:329-340, Yale Journal of Biology and Medicine, United States (1963).

Azeem, A., et al., "Microemulsions as a Surrogate Carrier for Dermal Drug Delivery," Drug development and industrial pharmacy 35(5):525-547, Informa Healthcare, England (2009).

Azure Pharma, Inc., "ELESTRIN—estradiol gel" Drug Info, http://dailymed.nlm.nih.gov/dailymed/archives/ fdaDrugInfo.cfm?archiveid=11885, 26 pages, (2009).

Bakhmutova-Albert, Ekaterina, et al.,"Enhancing Aqueous Dissolution Rates of Progesterone via Cocrystallization," SSCI, Division of Aptuit, Poster No. R6247, West Lafayette.

Banerjee, S., et al., "On the Stability of Salivary Progesterone Under Various Conditions of Storage," Steroids 46(6):967-974, Elsevier, United States (1985).

Barnett. and Steven, M., "Pressure-tuning infared and solution Raman spectroscopic studies of 17B-estradiol and several A-ring," Vibrational Spectroscopy, vol. 8, pp. 263, (1995).

Bartosova, L. and Bajgar, J., "Transdermal Drug Delivery in Vitro Using Diffusion Cells," Current Medicinal Chemistry 19(27):4671-4677, Bentham Science Publishers, Netherlands (2012).

Benbow, A.L. and Waddell, B.J., "Distribution and Metabolism of Maternal Progesterone in the Uterus, Placenta, and Fetus During Rat Pregnancy," Biology Of Reproduction 52(6):1327-1333, Society for the Study of Reproduction, United States (1995).

Bernabei, M.T., et al., "[Release of Polymorphic forms of Progesterone From Dimethylpolysiloxane Matrices]," Bollettino chimico farmaceutico 122(1):20-26, Societa Editoriale Farmaceutica, Italy (1983).

Busetta, P.B., et al., "Structure Cristalline et Moleculaire du Complexe Oestradiol-Propanol," Acta Crystallographica B28:1349-1351 (1972).

Busetta, P.B. and Hospital, M., "Structure Cristalline et Moleculair de l'Oestradiol Hemihydrate," Acta Crystallographica B28:560-567, (1972).

Bhavnani, B.R. and Stanczyk, F.Z., "Misconception and Concerns About Bioidentical Hormones Used for Custom-Compounded Hormone Therapy," The Journal of clinical endocrinology and metabolism 97(3):756-759, Endocrine Society, United States (2012).

(56) References Cited

OTHER PUBLICATIONS

Bhavnani, B.R. and Stanczyk, F.Z., "Pharmacology of Conjugated Equine Estrogens: Efficacy, Safety and Mechanism of Action," The Journal of steroid biochemistry and molecular biology 142:16-29, Pergamon, England (2014).

Bhavnani, B.R., et al., "Structure Activity Relationships and Differential interactions and Functional Activity of Various Equine Estrogens Mediated Via Estrogen Receptors (Ers) Eralpha and Erbeta," Endocrinology 149(10):4857-4870, Endocrine Society, United States (2008).

BioMed Centrai,Solubility of Progesterone in Organic Solvents, Online PDF, http://www.biomedcentral.com/content/ supplementary/ 1475-2859-11-106-S2.pdf.

Blake, E.J., et al., "Single and Multidose Pharmacokinetic Study of a Vaginal Micronized Progesterone insert (Endometrin ) Compared with Vaginal Gel in Healthy Reproductive-Aged Female Subjects," Fertility and Sterility 94(4):1296-1301, Elsevier for the American Society for Reproductive Medicine, United States (2010).

Borka. and Laszlo., Crystal Polymorphism of Pharmaceuticals, Acta Pharmaceutica Jugoslavia 40:71-94, (1990).

Brandstatter-Kuhnert, M., Kofler A., "Zur mikroskopischen Identitatsprufung and zur Polymorphie der Sexualhormone," Microchimica Acta 6:847-853, Springer-Verlag, Germany (1959).

Christensson, J.B., et al., "Positive Patch Test Reactions to Oxidized Limonene: Exposure and Relevance," Contact Dermatitis 71(5):264-272, Wiley, England (2014).

Brinton, L.A. and Felix, A.S., "Menopausal Hormone Therapy and Risk of Endometrial Cancer," The Journal of steroid biochemistry and molecular biology 142:83-89, Pergamon, England (2014).

"British Pharmacopoeia 2014 Online, Refined Maize Oil, Ph. Eur. Monograph 1342, vol. I & II, Monographs: Medicinal and Pharmaceutical Substances, accessed at http:/www.pharmacopoeia.co. uklbp2014/ixbin/bp.egi?a=print&id=7400&tab=a-z%20index[Feb. 3, 2014 1:37:50 PM]".

Burry, K.A., et al., "Percutaneous Absorption of Progesterone in Postmenopausal Women Treated with Transdermal Estrogen," American journal of obstetrics and gynecology 180(6Pt1):1504-1511, Elsevier, United States (1999).

Campsteyn, H., et al., "Structure Cristalline et Molcculaire de la Progesterone C21H3002," Acta Crystallographica B28 :3032-3042, (1972).

Cendejas-Santana, G., et al., "Growth and characterization of progesterone crystallites," Revista Mexicana de Fisica 50 S(1) : 1-3, (2004).

ChemPro, Top-Notch Technology in Production of Oils and Fats, Chempro-Edible-Oii-Refining-ISO-TUV-Austria.

Christen, R.D., et al., "Phase I/Pharmacokinetic Study of High-Dose Progesterone and Doxorubicin," Journal of Clinical Oncology : Official Journal of the American Society of Clinical Oncology 11(12):2417-2426, American Society of Clinical Oncology, United States (1993).

Christensson, J.B., et al., "Limonene Hydroperoxide Analogues Differ in Allergenic Activity," Contact Dermatitis 59(6):344-352, Wiley, England (2008).

Christensson, J.B., et al., "Limonene Hydroperoxide Analogues Show Specific Patch Test Reactions," Contact Dermatitis 70(5):291-299, Wiley, England (2014).

Chun et al., "Transdermal Delivery of Estradiol and Norethindrone Acetate: Effect of Vehicles and Pressure Sensitive Adhesive Matrix," Journal of Korean Pharmaceutical Sciences 35(3):173-177, (2005).

Cicinelli, E., et al., "Direct Transport of Progesterone From Vagina to Uterus," Obstetrics and Gynecology 95(3):403-406, Lippincott Williams & Wilkins, United States (2000).

Committee of Obstetric Practice, Committee Opinion—No. 522, Obstetrics & Gynecology, 119(4):879-882, (2012).

Commodari, F., et al., "Comparison of 17Beta-Estradiol Structures From X-Ray Diffraction and Solution Nmr," Magnetic resonance in chemistry : MRC 43(6):444-450, Wiley Heyden, England (2005).

Cooper, A., et al., "Systemic Absorption of Progesterone From Progest Cream in Postmenopausal Women," Lancet 351(9111):1255-1256, Lancet Publishing Group, England (1998).

International Search Report and written opinion for International Application No. PCT/US13/46442, dated Nov. 1, 2013.

International Search Report and written opinion for International Application No. PCT/US13/46443, dated Oct. 31, 2013.

International Search Report and written opinion for International Application No. PCT/US13/46444, dated Oct. 31, 2013.

International Search Report and written opinion for International Application No. PCT/US13/46445, dated Nov. 1, 2013.

International Search Report and Written Opinion for related International Application No. PCT/US13/023309, dated Apr. 9, 2013.

International Search report for corresponding International Application No. PCT/US12/66406, dated Jan. 24, 2013.

Corbett, S.H., et al., "Trends in Pharmacy Compounding for Women'S Health in North Carolina : Focus on Vulvodynia," Southern Medical Journal 107(7):433-436, Southern Medical Association, United States (2014).

Corn Refiners Assoc. Com Oil, Edition 5, United States (2006).

Critchley, H.O., et al., "Estrogen Receptor Beta, but Not Estrogen Receptor Alpha, Is Present in the Vascular Endothelium of the Human and Nonhuman Primate Endometrium," The Journal of Clinical Endocrinology and Metabolism 86(3):1370-1378, Endocrine Society, United States (2001).

Dauqan, Eqbal M.A., et al., "Fatty Acids Composition of Four Different Vegetable Oils (Red Palm Olein, Palm Olein, Corn Oil," IPCBEE, 14, IACSIT Press, Singapore (2011).

Dideberg, O., et al., "Crystal data on progesterone (C21H3002), desoxycorticosterone (C21H3003), corticosterone (C21H3004) and aldosterone," Journal of Applied Crystallography 4:80, (1971).

Diramio, J.A., et al., "Poly(Ethylene Glycol) Methacrylate/ Dimethacrylate Hydrogels for Controlled Release of Hydrophobic Drugs," Masters of Science Thesis, University of Georgia, Athens, Georgia, 131 pages (2002).

Diramio. "Polyethylene Glycol Methacrylate/Dimetacrylate Hydrogels for Controlled Release of Hydrophobic Drugs," The University of Georgia-Masters of Science Thesis, http://athenaeum.libs.uga.edu/ bitstream/handle/10724/7820/diramio_jackie_a_200412_ms.pdf?sequence=1, 131 pages, (2004).

Drakulic, B.J., et al., "Role of Complexes formation Between Drugs and Penetration Enhancers in Transdermal Delivery," International journal of pharmaceutics 363(1-2):40-49, Elsevier/North-Holland Biomedical Press., Netherlands (2008).

Du, J.Y., et al., "Percutaneous Progesterone Delivery Via Cream or Gel Application in Postmenopausal Women : A Randomized Cross-Over Study of Progesterone Levels in Serum , Whole Blood , Saliva, and Capillary Blood," Menopause 20(11):1169-1175, Lippincott-Raven Publishers, United States (2013).

Duclos, R., et al., "Polymorphism of Progesterone: Influence of the carrier and of the solid dispersion manufacturing process. A calorimetric and radiocrystallographic study," Journal of Thermal Analysis 37:1869-1875, John Wiley & Sons, England (1991).

Ebian, A.R., "Ebian Article: Polymorphism and solvation of ethinyl estradiol," Pharmaceutica Acta Helvetiae 54(4):111-114, (1979).

Eisenberger, A. and Westhoff, C., "Hormone Replacement Therapy and Venous Thromboembolism," The Journal of steroid biochemistry and molecular biology 142:76-82, Pergamon, England (2014).

Engelhardt, H., et al., "Conceptus influences the Distribution of Uterine Leukocytes During Early Porcine Pregnancy," Biology of Reproduction 66(6):1875-1880, Society for the Study of Reproduction, United States (2002).

Ettinger, B., et al., "Comparison of Endometrial Growth Produced by Unopposed Conjugated Estrogens or by Micronized Estradiol in Postmenopausal Women," American Journal of Obstetrics and Gynecology 176(1 Pt1):112-117, Elsevier, United States (1997).

Excipients for Pharmaceuticals, Sasol Olefins & Surfactants GMBH, 28 pages (2010).

Faassen, F., et al., "Physicochemical Properties and Transport of Steroids Across Caco-2 Cells," Pharmaceutical research 20(2):177-186, Kluwer Academic/Plenum Publishers, United States (2003).

(56) References Cited

OTHER PUBLICATIONS

"FDA, Draft Guidance on Progesterone, accessed at http://www.fda.gov/downloads/Drugs/GuidanceComplianceRegulatoryInformation/Guidances/UCM209294.pdf, accessed on (Recommended) Apr. 2010,(Revised) Feb. 2011."
Ferrari, Roseli AP., et al., "Oxidative Stability of Biodiesel From Soybean Oil Fatty Acid Ethyl Esters," Scientia Agricola 62(3):291-95, Piracicaba, brazil (2005).
Filipsson,F., et al., "Concise International Chemical Assessment Document 5," Limonene, first draft, World Health Organization, Geneva, 36 pages (1998).
Final Office Action dated Jul. 16, 2013 for U.S. Appl. No. 13/684,002, filed Nov. 21, 2012.
Final Office Action dated Oct. 26, 2012for U.S. Appl. No. 12/561,515, filed Sep. 17, 2009.
Flyvholm, M.A. and Menne, T., "Sensitizing Risk of butylated Hydroxytoluene Based on Exposure and Effect Data," Contact Dermatitis 23(5):341-345, Wiley, England (1990).
Fotherby. K., "Bioavailability of Orally Administered Sex Steroids Used in Oral Contraception and Hormone Replacement Therapy," Contraception 54(2):59-69, Elsevier, United States (1996).
Franklin, R.D. and Kutteh, W.H., "Characterization of Immunoglobulins and Cytokines in Human Cervical Mucus : influence of Exogenous and Endogenous Hormones," Journal of Reproductive Immunology 42(2):93-106, Elsevier/North-Holland Biomedical Press, Ireland (1999).
Franz, T.J., et al., "Use of Excised Human Skin to Assess the Bioequivalence of Topical Products," Skin Pharmacology and Physiology 22(5):276-286, Karger, Switzerland (2009).
Freedman, R.R., "Menopausal Hot Flashes: Mechanisms, Endocrinology, Treatment," The Journal of steroid biochemistry and molecular biology 142:115-120, Pergamon, England (2014).
Fuchs, K.O., et al., "The Effects of an Estrogen and Glycolic Acid Cream on the Facial Skin of Postmenopausal Women: A Randomized Histologic Study," Aesthetic Dermatology 8(1):14-19, (2006).
Fuchs, K.O., et al., "The Effects of an Estrogen and Glycolic Acid Cream on the Facial Skin of Postmenopausal Women: A Randomized Histologic Study," Cutis 71(6):481-488, Frontline Medical Communications, United States (2003).
Fuchs, K.O., et al., "The Effects of an Estrogen and Glycolic Acid Cream on the Facial Skin of Postmenopausal Women: A Randomized Histologic Study," Pharmacology/Cosmetology 5(1), (2006).
Fugh-Berman, A. and Bythrow, J., "Bioidentical Hormones for Menopausal Hormone Therapy: Variation on a Theme," Journal of general internal medicine 22(7):1030-1034, Springer, United States (2007).
Furness, S., et al., "Hormone therapy in Postmenopausal Women and Risk of Endometrial Hyperplasia," The Cochrane Database Of Systematic Reviews 8:1-204, Wiley, England (2012).
Gafvert, E., et al., "Free Radicals in Antigen formation: Reduction of Contact Allergic Response to Hydroperoxides by Epidermal Treatment with Antioxidants," The British Journal of Dermatology 146(4):649-656, Blackwell Scientific Publications, England (2002).
Ganem-Quintanar., et al., "Evaluation of the transepidermal permeation of diethylene glycol monoethyl ether and skin water loss," International Journal of Pharmaceutics, 147(2):165-171, (1997) Abstract Only.
Gattefossé SAS, Regulatory Data Sheet, Gelot 64, 6 pages (2012).
Gattefossé SAS, Regulatory Data Sheet, Lauroglycol 90, 5 pages (2012).
Gattefosse, "Excipients for Safe and Effective Topical Delivery," http://drug-dev.com/Main/Back-Issues/Transdermal-Topical-Subcutaneous-NonInvasive-Deliv-5.aspx# (2012).
Gattefosse SAS, Material Safety Data Sheet, Gelot 64, 8 pages 2012.
Gillet, J.Y., et al., "induction of Amenorrhea During Hormone Replacement therapy : Optimal Micronized Progesterone Dose a Multicenter Study," Maturitas 19(2):103-115, Elsevier/North Holland Biomedical Press, Ireland (1994).
Giron, D., "Thermal analysis and calorimetric methods in the characterisation of polymorphs and solvates," Thermochimica Acta 248:1-59, Elsevier B.V., Netherlands (1995).
Giron-Forest, D., et al., "Thermal Analysis Methods for Pharmacopoeial Materials," Journal of pharmaceutical and biomedical analysis 7(12):1421-1433, Elsevier Science, England (1989).
Glaser, R.L., et al., "Pilot Study : Absorption and Efficacy of Multiple Hormones Delivered in a Single Cream Applied to the Mucous Membranes of the Labia and Vagina," Gynecologic and Obstetric Investigation 66(2):111-118,Basel, New York, Karger., Switzerland (2008).
Golatowski, C., et al., "Comparative Evaluation of Saliva Collection Methods for Proteome Analysis," International Journal of Clinical Chemistry 419:42-46,Elsevier., Netherlands (2013).
Graham, J.D. and Clarke, C.L., "Physiological Action of Progesterone in Target Tissues," Endocrine Reviews 18(4):502-519, Endocrine Society, United States (1997).
Groothuis, P.G., et al., "Estrogen and the Endometrium : Lessons Learned From Gene Expression Profiling in Rodents and Human," Human Reproduction Update 13(4):405-417, Published for the European Society of Human Reproduction and Embryology by Oxford University Press, England (2007).
Gunstone, Frank, D., et al., "Vegetable Oils in Food Technology: Composition, Properties and Uses," Blackwell Publishing, CRC Press, (2002).
Gurney, E.P., et al., "The Women"S Health initiative Trial and Related Studies: 10 Years Later: a Clinician"S View," The Journal of steroid biochemistry and molecular biology 142:42105, Pergamon, England (2014).
Hamid, K.A., et al., "The Effects of Common Solubilizing Agents on the intestinal Membrane Barrier Functions and Membrane Toxicity in Rats,"International Journal Of Pharmaceutics 379(1):100-108,Amsterdam, Elsevier/North-Holland Biomedical Press., Netherlands (2009).
Hapgood, J.P., et al., "Potency of Progestogens Used in Hormonal Therapy: Toward Understanding Differential Actions," The Journal of steroid biochemistry and molecular biology 142:39-47, Pergamon, England (2014).
Hargrove, J.T., et al., "Menopausal Hormone Replacement Therapy with Continuous Daily Oral Micronized Estradiol and Progesterone," Obstetrics and gynecology 73(4):606-612, Lippincott Williams & Wilkins, United States (1989).
Haner B.A., and Norton, D.A., "Crystal data (I) for some pregnenes and pregnadienes," Acta Crystallographica 17:1610, (1964).
Hatton, J., et al., "Safety and Efficacy of a Lipid Emulsion Containing Medium-Chain Triglycerides," Clinical Pharmacy 9(5):366-371, American Society of Hospital Pharmacists, United States (1990).
He, F., et al., "Apoptotic Signaling Pathways in Uteri of Rats with Endometrial Hyperplasia induced by Ovariectomy Combined with Estrogen," Gynecologic and Obstetric Investigation 76(1):51-56,Karger., Switzerland (2013).
Helbling, I.M., et al., "The Optimization of an intravaginal Ring Releasing Progesterone Using a Mathematical Model," Pharmaceutical research 31(3):795-808, Kluwer Academic/Plenum Publishers, United States (2014).
Helmy, A., et al., "Estrogenic Effect of Soy Phytoestrogens on the Uterus of Ovariectomized Female Rats, "Clinical Pharmacology & Biopharmaceutics, S2, 7 pages (2014).
Henderson, V.W., "AlzheimerS Disease: Review of Hormone Therapy Trials and Implications for Treatment and Prevention After Menopause," The Journal of steroid biochemistry and molecular biology 142:99-106, Pergamon, England (2014).
Henriksen. Thormod, et al., "An Endor Sturdy of Radiation-Induced Molecular Damage to Progesterone," Journal of Magnetic Resonance 63(2):333-342, Elsevier Inc., United States (1985).
Hodis, H.N. and Mack, W.J., "Hormone Replacement Therapy and the association with Coronary Heart Disease and Overall Mortality: Clinical Application of The Timing Hypothesis," The Journal of steroid biochemistry and molecular biology 142:68-75, Pergamon, England (2014).

(56) References Cited

OTHER PUBLICATIONS

Hospital, M., et al., "X-Ray Crystallography of Estrogens and Their Binding to Receptor Sites," Molecular pharmacology 8(4):438-445, American Society for Pharmacology and Experimental Therapeutics, United States (1972).
Hostynek, J., et al., "Predictinga bsorptiono f fragrancec hemicalst hrough human skin," Journal of the Society of Cosmetic Chemists 46:221-229, (1995).
Hulsmann, S., et al., "Stability of Extruded 17 Beta-Estradiol Solid Dispersions," Pharmaceutical Development and Technology 6(2):223-229, Informa Healthcare, England (2001).
Hurn, P.D. and Macrae, I.M., "Estrogen as a Neuroprotectant in Stroke," Journal of Cerebral Blood Flow and Metabolism : Official Journal of the International Society of Cerebral Blood Flow and Metabolism 20(4):631-652, Nature Publishing Group, United States (2000).
Hyder, S.M., et al., "Synthetic Estrogen 17Alpha-Ethinyl Estradiol induces Pattern of Uterine Gene Expression Similar to Endogenous Estrogen 17Beta-Estradiol," The Journal of Pharmacology and Experimental Therapeutics 290(2):740-747, American Society for Pharmacology and Experimental Therapeutics, United States (1999).
Johanson, G., "Toxicity Review of Ethylene Glycol Monomethyl Ether and its Acetate Ester," Critical reviews in toxicology 30(3):307-345, Informa Healthcare, England (2000).
Johnson, S., Williams, and John, F.W. Keana , "Racemic Progesterone," Tetrahedron Letters 4(4):193-196, Pergamon Press Ltd., United Kingdom (1963).
Joshi, S.G., et al., "Detection and Synthesis of a Progestagen-Dependent Protein in Human Endometrium," Journal of Reproduction and Fertility 59(2):273-285, Portland Press, England (1980).
Kanno J., et al., "The Oecd Program to Validate the Rat Uterotrophic Bioassay to Screen Compounds for in Vivo Estrogenic Responses : Phase 1," Environmental Health Perspectives 109(8):785-794,N. C. National Institute of Environmental Health Sciences., United States (2001).
Karlberg, A.T., et al., "Air Oxidation of D-Limonene (the Citrus Solvent) Creates Potent Allergens," Contact Dermatitis 26(5):332-340, Wiley, England (1992).
Karlberg, A.T., et al., "Influence of an Anti-Oxidant on the formation of Allergenic Compounds During Auto-Oxidation of D-Limonene," The Annals of Occupational Hygiene 38(2):199-207, Oxford University Press, England (1994).
Kaunitz, A.M. "Extended Duration Use of Menopausal Hormone therapy," Menopause 21(6):679-681, Lippincott-Raven Publishers, United States (2014).
Khalil, S.A.H., "Stability and Dissolution Rates of Corticosteroids in Polyethylene Glycol Solid Dispersions," Drug Development and Industrial Pharmacy 10(5):771-787, Marcel Dekker, New York (1984).
Kharode, Y., et al., "The Pairing of a Selective Estrogen Receptor Modulator, Bazedoxifene, with Conjugated Estrogens as a New Paradigm for the Treatment of Menopausal Symptoms and Osteoporosis Prevention," Endocrinology 149(12):6084-6091, Endocrine Society, United States (2008).
Kim, Y.W., et al., "Safety Evaluation and Risk Assessment of D-Limonene," Journal of Toxicology and Environmental Health. Part B, Critical Reviews 16(1):17-38, Informa Healthcare, England (2013).
Kincl, F.A., et al., "Increasing Oral Bioavailability of Progesterone by formulation," Journal of steroid biochemistry 9(1):83-84, Pergamon Press, England (1978).
Knuth., et al., "Hydrogel delivery systems for vaginal and oral applications: Formulation and biological considerations," Advanced Drug Delivery Reviews, 11(1-2):137-167, (1993) Abstract Only.
Koga, K., et al., "Enhancing Mechanism of Labrasol on intestinal Membrane Permeability of the Hydrophilic Drug Gentamicin Sulfate," European Journal of Pharmaceutics and Biopharmaceutics : Official Journal of Arbeitsgemeinschaft Fur Pharmazeutische Verfahrenstechnik E.V 64(1):82-91, Elsevier Science, Netherlands (2006).

Komm, B.S., et al., "Bazedoxifene Acetate : A Selective Estrogen Receptor Modulator with Improved Selectivity," Endocrinology 146(9):3999-4008, Endocrine Society, United States (2005).
Korkmaz, Filiz, "Biophysical Studies of Progesterone-Model Membrane Interactions," a Thesis Submitted to the Graduate School of Natural and Applied Sciences of the Middle East Technical University (2003).
Kotiyan, P.N. and Vavia, P.R., "Stability indicating Hptic Method for the Estimation of Estradiol," Journal of pharmaceutical and biomedical analysis 22(4):667-671, Elsevier Science, England (2000).
Krzyminiewski, R., et al., "EPR Study of the Stable Radical in a y-Irradialed Single Crystal of Progesterone," Journal of Magnetic Resonance 46:300-305, Acedemic Press, England (1982).
Kubli-Garfias, C., et al., "Ab initio calculations of the electronic structure of glucocorticoids," Journal of Molecular Structure, Theochem 454(2-3):267-275, Elsevier Science B.V., Netherlands (1998).
Kubli-Garfias, Carlos, "Ab initio study of the electronic structure of progesterone and related progestins," Journal of Molecular Structure, Theochem 425(1-2):171-179, Elsevier B.V., Netherlands (1998).
Kuhnert-Brandstaetier, M., Kofler, A., "Zur Unterscheidung von losungsmittelhaltigen pseudopolymorphen Kristallformen und polymorphen Modifikationen bei Steroidhormonen.II.," 1:127-139, Mikrochimica Acta (1968).
Kuhnert-Brandstaetier, M., Lnder, R., "Zur Hydratbildung bei Steroidhormonen," Sci. Pharm. 41(2):109-116, (1973).
Kuhnert-Brandstatier, M., "Thermo-microscopic and spectrophotometric: Determination of steroid hormones," Microchemical Journal 9:105-133, (1965).
Kumasaka, T., et al., "Effects of Various forms of Progestin on the Endometrium of the Estrogen-Primed , Ovariectomized Rat," Endocrine Journal 41(2):161-169, Japan Endocrine Society, Japan (1994).
Kuon, R.J. and Garfield, R.E., "Actions of Progestins for the inhibition of Cervical Ripening and Uterine Contractions to Prevent Preterm Birth," Facts, Views &Amp; Vision in Obgyn 4(2):110-119,Flemish Society of Obstetrics & Gynaecology, Belgium (2012).
Kuon, R.J., et al., "A Novel Optical Method to Assess Cervical Changes During Pregnancy and Use to Evaluate the Effects of Progestins on Term and Preterm Labor," American Journal of Obstetrics and Gynecology 205(1):82.e15-82.e20, Elsevier, United States (2011).
Kuon, R.J., et al., "Pharmacologic Actions of Progestins to inhibit Cervical Ripening and Prevent Delivery Depend on their Properties, the Route of Administration , and the Vehicle," American Journal of Obstetrics and Gynecology 202(5):455.e1-455.e9, Elsevier, United States (2010).
Labrie, et al., "Intravaginal prasterone (DHEA) provides local action without clinically significant changes in serum concentrations of estrogens or androgens," Journal of Steroid Biochemistry & Molecular Biology 138:359-367, Elsevier (2013).
Lacey, J.V. Jr., "The Whi Ten Year"S Later: an Epidemiologist"S View," The Journal of steroid biochemistry and molecular biology 142:12-15, Pergamon, England (2014).
Lahiani-Skiba, M., et al., "Solubility and Dissolution Rate of Progesterone-Cyclodextrin-Polymer Systems," Drug development and industrial pharmacy 32(9):1043-1058, Informa Healthcare, England (2006).
Lancaster, R.W., et al., "The Polymorphism of Progesterone: Stabilization of a "Disappearing" Polymorph by Co-Crystallization," Journal of pharmaceutical sciences 96(12):3419-3431, Wiley-Liss, United States (2007).
Land, Laura M., "The influence of water content of triglyceride oils on the solubility of steriods," Pharmaceutical Research 22(5):Springer Science+Business Media (2005).
Lanigan, R.S. and Yamarik, T.A., "Final Report on the Safety Assessment of Bht (1)," International Journal of Toxicology 21(2):19-94, Sage Publications, United States (2002).
Lapez-Belmonte, J., et al., "Comparative Uterine Effects on Ovariectomized Rats After Repeated Treatment with Different Vaginal Estrogen formulations," Maturitas 72(4):353-358, Elsevier/ North Holland Biomedical Press, Ireland (2012).
Idder, Salima, et al., "Physicochemical properties of Progesterone," 1-26, American Chemical Society & U.S. National Library of Medicine (2014).

(56) References Cited

OTHER PUBLICATIONS

Leonetti, H.B., et al., "Topical Progesterone Cream Has an Antiproliferative Effect on Estrogen-Stimulated Endometrium," Fertility and sterility 79(1):221-222, Elsevier for the American Society for Reproductive Medicine, United States (2003).
Leonetti, H.B., et al., "Transdermal Progesterone Cream as an Alternative Progestin in Hormone therapy," Alternative Therapies in Health and Medicine 11(6):36-38, InnoVision Communications, United States (2005).
Lewis, J.G., et al., "Caution on the Use of Saliva Measurements to Monitor Absorption of Progesterone From Transdermal Creams in Postmenopausal Women," Maturitas 41(1):1-6, Elsevier/North Holland Biomedical Press, Ireland (2002).
Li, G.C., et al., "Solid-State Nmr Analysis of Steroidal Conformation of 17Î±- and 17Î²-Estradiol in the Absence and Presence of Lipid Environment," Steroids 77(3):185-192, Elsevier, United States (2012).
Lobo, R.A., "foreword: Hormone Therapy Arms," The Journal of steroid biochemistry and molecular biology 142:3, Pergamon, England (2014).
Lucy., et al., "Gonadotropin-releasing hormone at estrus: luteinizing hormone, estradiol, and progesterone during the periestrual and postinsemination periods in dairy cattle," Bioi Reprod 35(2):300-11, (1986) Abstract Only.
Lvova, M.Sh., et al., "Thermal Analysis in the Quality Control and Standardization of Some Drugs," Journal of Thermal Analysis 40:405-411, Wiley (1993).
Madishetti, S.K., et al., "Development of Domperidone Bilayered Matrix Type Transdermal Patches : Physicochemical , in Vitro and Ex Vivo Characterization," Journal of Faculty of Pharmacy 18(3):221-229, BioMed Central, England (2010).
Magness, R.R. and Ford, S.P., "Estrone, Estradiol-17 Beta and Progesterone Concentrations in Uterine Lymph and Systemic Blood Throughout the Porcine Estrous Cycle," Journal of animal science 57(2):449-455, American Society of Animal Science, United States (1983).
"Management of Symptomatic Vulvovaginal Atrophy: 2013 Position Statement of the North American Menopause Society," Menopause 20(9):888-902, Lippincott-Raven Publishers, United States (2013).
Mcguffy, Irena, "Softgel Technology as a Lipid-Based Delivery Tool for Bioavailability Enhancement," Catalent Pharma Solutions Somerset, NJ (2011).
"Merck Index, Estradiol, The Merck Index Online, Royal Society of Chemistry 2014," https://www.rsc.org/Merck-Index/monograph/mono1500003758/estradiol?q=unauthorize.
"Merck Index Online, Progesterone, Royal Society of Chemistry, accessed at https:l/www.rsc.org/Merck-IndeXImonograph/print/mono1500007889/progesterone?q=authorize, accessed on 2013 search Feb. 17, 2014."
"Merck Index Online, Progesterone, Royal Society of Chemistry, accessed at https://www.rsc.org/Merck-Index/monograph/print/mono1500007889/progesterone?q=authorize, accessed at 2013, search Feb. 24, 2014."
Mesley, R.J., "Clathrate formation From Steroids," Chemistry & industry 37:1594-1595, John Wiley & Sons Ltd., England (1965).
Miao, Wenbin, et al., Chemical Properties of Progesterone American Chemical Society & U.S. National Library of Medicine (2014).
Miles, R.A., et al., "Pharmacokinetics and Endometrial Tissue Levels of Progesterone After Administration by intramuscular and Vaginal Routes : A Comparative Study," Fertility and Sterility 62(3):485-490, Elsevier for the American Society for Reproductive Medicine, United States (1994).
Miller, J.A., et al., "Safety and Feasibility of Topical Application of Limonene As a Massage Oil to the Breast," Journal of Cancer Therapy 3(5A), Scientific Research Publishing, United States (2012).
Mueck, A.O., et al., "Genomic and Non-Genomic Actions of Progestogens in The Breast," the Journal of steroid biochemistry and molecular biology 142:62-67, Pergamon, England (2014).
Muramatsu, Mitsuo, "Thermodynamic Relationship between a- and B-Forms of Crystalline Progesterone," Journal of Pharmaceutical Sciences 68(2):175-178, American Pharmacists Association (1979).
Ng, Jo-Han., et al., "Advances in biodiesel fuel for application in compression ignition engines," Clean Technologies and Environmental Policy 12:459-493, Springer-Verlag (2010).
Nicklas, M., et al., "Preparation and Characterization of Marine Sponge Collagen Nanoparticles and Employment for the Transdermal Delivery of 17Beta-Estradiol-Hemihydrate," Drug development and industrial pharmacy 35(9):1035-1042, Informa Healthcare, England (2009).
Nilsson, U., et al., "Analysis of Contact Allergenic Compounds in Oxidized d-Limonene," Chromatographia 42:199-205, (1996).
Non Final Office Action dated Dec. 12, 2011 for U.S. Appl. No. 12/561,515, filed Sep. 17, 2009.
Non-Final Office Action dated Feb. 18, 2014 for U.S. Appl. No. 14/099,545, filed Dec. 6, 2013.
Non-Final Office Action dated Mar. 20, 2013 for U.S. Appl. No. 13/684,002, filed Nov. 21, 2012.
Notelovitz, M., et al., "initial 17Beta-Estradiol Dose for Treating Vasomotor Symptoms," Obstetrics and Gynecology 95(5):726-731, Lippincott Williams & Wilkins, United States (2000).
Notice of Allowance dated Dec. 6, 2013 for U.S. Appl. No. 13/684,002, filed Nov. 21, 2012.
Notice of Allowance dated Sep. 11, 2013 for U.S. Appl. No. 12/561,515, filed Sep. 17, 2009.
NuGen, "What is NuGen HP Hair Growth System?," http://www.skinenergizer.com/Nugen-HP-Hair-Grow1h-System-p/ senusystem.htm, 3 pages, undated.
NuGest 900™, http://www.lhehormoneshop.nel/nugest900.htm, 4 pages, undated.
O'Leary, P., et al., "Salivary, but Not Serum or Urinary Levels of Progesterone are Elevated After Topical Application of Progesterone Cream to Pre- and Postmenopausal Women," Clinical Endocrinology 53(5):615-620,Blackwell Scientific Publications, England (2000).
"Open Notebook, Science Solubility Challenge, Solubility of progesterone in organic solvents, accessed at http://lxsrv7.oru.edu/-alang/onsc/solubility/allsolvents.php?solute=progesterone, accessed on Jul. 16, 2013".
Opinion on Diethylene glycol monoethyl ether, Scientific Committee on Consumer Products, The SCCP adopted this opinion at its 10th plenary,27 pages (2006).
Outterson, K. "The Drug Quality and Security Act—Mind the Gaps," The New England Journal of Medicine 370(2):97-99,Massachusetts Medical Society., United States (2014).
Panay, N., et al., "The 2013 British Menopause Society & Women's Health Concern recommendations on hormone replacement therapy," DOI: 0.1177/1754045313489645, min.sagepub.com. Menopause International: The Integrated Journal of Post reproductive Health 0(0):1-10, (2013).
Panay, N., et al., "The 2013 British Menopause Society & Women's Health Concern Recommendations on Hormone Replacement Therapy," Menopause international 19(2):59-68, Sage, England (2013).
Panay, N., et al., "The 2013 British Menopause Society & Women's Health Concern recommendations on hormone replacement therapy," Menopause International: The Integrated Journal of Postreproductive Health, published online May 23, 2013, Sage Publications. http://min.sagepub.com/content/early/2013/05/23/1754045313489645.1.
Panchagnula, R. and Ritschel, W.A., "Development and Evaluation of an intracutaneous Depot formulation of Corticosteroids Using Transcutol as a Cosolvent: in-Vitro, Ex-Vivo and in-Vivo Rat Studies," The Journal of pharmacy and pharmacology 43(9):609-614, Wiley, England (1991).
Parasuraman, S., et al., "Blood Sample Collection in Small Laboratory Animals," Journal of Pharmacology &Amp; Pharmacotherapeutics 1(2):87-93, Medknow Publications and Media, India (2010).
Park, J.S., et al., "Solvent Effects on Physicochemical Behavior of Estradiols Recrystallized for Transdermal Delivery," Archives of pharmacal research 31(1):111-116, Pharmaceutical Society of Korea., Korea (South) (2008).

(56) References Cited

OTHER PUBLICATIONS

Park, J.S., et al., "Use of Cp/Mas Solid-State Nmr for the Characterization of Solvate Molecules within Estradiol Crystal forms," European journal of pharmaceutics and biopharmaceutics 60(3):407-412, Elsevier Science, Netherlands (2005).
Parrish, D.A. and Pinkerton, A.A., "A New Estra-1,3,5(10)-Triene-3,17Beta-Diol Solvate: Estradiol-Methanol-Water (3/2/1)," Acta crystallographica. Section C, Crystal structure communications 59(Pt2):o80-82, Wiley-Blackwell, United States (2003).
Patel., et al., "Transdermal Drug Delivery System: A Review," The Pharma Innovation, The Pharma Journal 1(4), (2012).
Payne, R.S., et al., "Examples of Successful Crystal Structure Prediction: Polymorphs of Primidone and Progesterone," International Journal of Pharmaceutics 177(2):231-245, Elsevier/North-Holland Biomedical Press., Netherlands (1999).
PCCA, Apothogram, PCCA, Houston, TX, (2014).
Persson, Linda C, et al., "Physicochemical Properties of Progesterone Selecte," 1-5, American Chemical Society & U.S. National Library of Medicine (2014).
Pfaus, J.G., et al., "Selective Facilitation of Sexual Solicitation in the Female Rat by a Melanocortin Receptor Agonist," Proceedings of the National Academy of Sciences of the United States of America 101(27):10201-10204, National Academy of Sciences, United States (2004).
Pheasant, Richard, , "Polymorphism of 17-Ethinylestradiol," Schering Corporation, Bloomfield, NJ (1950).
Pickles, V.R. "Cutaneous Reactions to injection of Progesterone Solutions into the Skin," British Medical Journal 2(4780):373-374, British Medical Association, England (1952).
Pinkerton, J.V. and Thomas, S., "Use of Serms for Treatment in Postmenopausal Women," The Journal of Steroid Biochemistry and Molecular Biology 142:142-154, Pergamon, England (2014).
Pinkerton, J.V. "What are the Concerns About Custom-Compounded "Bioidentical" Hormone therapy?," Menopause 21(12):1298-1300, Lippincott-Raven Publishers, United States (2014).
Pisegna, Gisia L, "A High-pressure Vibrational Spectroscopic Study of Polymorphism in Steroids," Thesis, McGill University, Dept. of Chem:National Library of Canada (1999).
Prajapati, Hetal N., et al., "A comparative Evaluation of Mono-, Di- and Triglyceride of Medium Chain Fatty Acids by Lipid/Surfactan UWater," Springerlink.com, pp. 1-21, (2011).
Prausnitz, M.R. and Langer, R., "Transdermal Drug Delivery," Nature Biotechnology 26(11):1261-1268, Nature America Publishing, United States (2008).
Price, S.L., "The Computational Prediction of Pharmaceutical Crystal Structures and Polymorphism," Advanced drug delivery reviews 56(3):301-319, Elsevier Science Publishers, B.V., Netherlands (2004).
Product Safety Assessment, Diethylene Glycol Monoethyl Ether, The Dow Chemical Company Page, 5 Pages (2007).
Progynova TS 100, available online at file:I//C:!Users/Caii%20Family/Desktop/Progynova%20TS%20100%2012%20Patches_Pack%20%28Estradioi%20Hemihydrate%29.html, 2010.
Provider Data Sheet, "About Dried Blood Spot Testing," ZRT Laboratory, 3 pages (2014).
Rahn, D.D., et al., "Vaginal Estrogen for Genitourinary Syndrome of Menopause: a Systematic Review," Obstetrics and Gynecology 124(6):1147-1156, Lippincott Williams & Wilkins, United States (2014).
Reisman, S.A., et al., "Topical Application of the Synthetic Triterpenoid Rta 408 Protects Mice From Radiation-induced Dermatitis," Radiation Research 181(5):512-520, Radiation Research Society, United States (2014).
Restriction/Election Requirement dated Mar. 5, 2014 for U.S. Appl. No. 14/099,623, filed Dec. 6, 2013.
Restriction/Election Requirement dated Feb. 20, 2014 for U.S. Appl. No. 14/099,562, filed Dec. 6, 2013.
Rosilio, V., et al., "Physical Aging of Progesterone-Loaded Poly(D,L,-Lactide-Co-Glycolide) Microspheres," Pharmaceutical research 15(5):794-798, Kluwer Academic/Plenum Publishers, United States (1998).
Ross, D., et al., "Randomized , Double-Blind , Dose-Ranging Study of the Endometrial Effects of a Vaginal Progesterone Gel in Estrogen-Treated Postmenopausal Women," American Journal of Obstetrics and Gynecology 177(4):937-941, Elsevier, United States (1997).
Ruan, X. and Mueck, A.O., "Systemic Progesterone therapy—Oral, Vaginal , injections and Even Transdermal ?," Maturitas 79(3):248-255, Elsevier/North Holland Biomedical Press, Ireland (2014).
Salem, H.F. "Sustained-Release Progesterone Nanosuspension Following intramuscular injection in Ovariectomized Rats," International Journal of Nanomedicine 10:943-954,DOVE Medical Press, New Zealand (2010).
Salole, E.G., "The Physicochemical Properties of Oestradiol," Journal of Pharmaceutical and Biomedical Analysis 5(7):635-648, Elsevier Science, England (1987).
Salole, Eugene G., "Estradiol, Analyllical Profiles of Drug Substances," vol. 15, pp. 283-318, (1986).
Santen, R.J., "Menopausal Hormone Therapy and Breast Cancer," The Journal of Steroid Biochemistry and Molecular Biology 142:52-61, Pergamon, England (2014).
Santen, R.J. "Vaginal Administration of Estradiol : Effects of Dose, Preparation and Timing on Plasma Estradiol Levels," The Journal of the International Menopause Society :1-14, Informa Healthcare, England (2014).
Sarkar, Basu, et al., "Chemical Stability of Progesterone in Compounded Topical Preparations using PLO Transdermal CreamTM and HRT CreamTM Base," Steroids and Hormonal Science 4:2, (2013).
Sarrel. and Philip., "The Mortality Toll of Estrogen Avoidance: An Analysis of Excess Deaths Among Hysterectomized Women Aged 50 to 59 Years," American Journal of Public Health, Research and Practice, pp. e1-e6, Published online ahead of print Jul. 18, 2013.
Satyanarayana, D, et al., "Aqueous Solubility Predictions of Aliphatic Alcohols, Alkyl Substituted Benzoates and Steroids," Asian Journal of Chemistry 9(3): 418-26, (1997).
Scavarelli, Rosa Maria, et al., Progesterone and Hydrate or Solvate, SciFinder, pp. 1-2, American Chemical Society (2014).
Schindler, A.E., "The "Newer" Progestogens and Postmenopausal Hormone Therapy (Hrt)," The Journal of Steroid Biochemistry and Molecular Biology 142:48-51, Pergamon, England (2014).
Schutte, S.C. and Taylor, R.N., "A Tissue-Engineered Human Endometrial Stroma That Responds to Cues for Secretory Differentiation , Decidualization , and Menstruation," Fertility and Sterility 97(4):997-1003, Elsevier for the American Society for Reproductive Medicine, United States (2012).
Schweikart, K.M., et al., "Comparative Uterotrophic Effects of Endoxifen and Tamoxifen in Ovariectomized Sprague-Dawley Rats," Toxicologic Pathology 42(8):1188-1196, Sage Publications, United States (2014).
SciFinder Scholar Prednisone Chemical Properties, SciFinde, pp. 1-7, National Library of Medicine (2014).
SciFinder Scholar Prednisone Physical Properties, SciFinder, pp. 1-10, Natioinal Library of Medicine (2014).
SciFinder Scholar Progesterone Experimental Properties, SciFinder, pp. 1-9, American Chemical Society (2014).
Serantoni, Foresti, et al., "4-Pregnen-3, 20-Dione (progesterone, form II)," Crystal Structure Communications 4(1):189-92, CAPLUS Database (1975).
Shao, R., et al., "Direct Effects of Metformin in the Endometrium: A Hypothetical Mechanism for the Treatment of Women with Pcos and Endometrial Carcinoma," Journal of Experimental & Clinical Cancer Research 33:41, BioMed Central, England (2014).
Sharma, H.C., et al., "Physical Properties of Progesterone Selected Refer, SciFinder," pp. 1-5, American Chemical Society & U.S. National Library of Medicine (2014).
Shrier, L.A., et al., "Mucosal Immunity of the Adolescent Female Genital Tract," The Journal of Adolescent Health 32(3):183-186, Elsevier, United States (2003).
Shufelt, C.L., et al., "Hormone Therapy Dose , formulation , Route of Delivery , and Risk of Cardiovascular Events in Women : Findings From the WomenS Health initiative Observational Study," Menopause 21(3):260-266, Lippincott-Raven Publishers, United States (2014).

(56) References Cited

OTHER PUBLICATIONS

Siew, A, et al.,"Bioavailability Enhancement with Lipid-Based Durg-Delivery Systems" Phamraceutical Technology 28,30-31, (2014).
Sigma-Aldrich, Progesterone-Water Soluble: powder, BioReagent, suitable for cell culture), MSDS available online: http://www.sigmaaldrich.com/catalog/producl/sigma/p7556.
Simon, J., et al., "Effective Treatment of Vaginal Atrophy with an Ultra-Low-Dose Estradiol Vaginal Tablet," Obstetrics and gynecology 112(5):1053-1060, Lippincott Williams & Wilkins, United States (2008).
Simon, J.A. "What If the Women'S Health initiative Had Used Transdermal Estradiol and Oral Progesterone instead?," Menopause 21(7):769-783, Lippincott-Raven Publishers, United States (2014).
Sitruk-Ware. and Regine., "Oral Micronized Progesterone—Bioavailability Pharmacokinetics, Pharmacological and Therapeutic Implications—A Review," Contraception 36(4):373-402, (1987).
Sitruk-Ware, R., "Progestogens in Hormonal Replacement Therapy: New Molecules, Risks, and Benefits," Menopause 9(1):6-15, Lippincott-Raven Publishers, United States (2002).
Smith and Nicholas., "Lower Risk of Cardiovascular Events in Postmenopausal Women Taking Oral Estradiol Compared with Oral Conjugated Equine Estrogens," JAMA Intern Med, pp. e1-e7, published online Sep. 30, 2013.
Smyth, H.F., et al., "A 2-Yr Study of Diethylene Glycol Monoethyl Ether in Rats," Food and Cosmetics Toxicology 2:641-642, Pergamon Press, England (1964).
Stanczyk, F.Z. and Bhavnani, B.R., "Current Views of Hormone Therapy for the Management and Treatment of Postmenopausal Women," The Journal of steroid biochemistry and molecular biology 142:1-2, Pergamon, England (2014).
Stanczyk, F.Z. and Bhavnani, B.R., "Use of Medroxyprogesterone Acetate for Hormone Therapy in Postmenopausal Women: Is It Safe?," The Journal of steroid biochemistry and molecular biology 142:30-38, Pergamon, England (2014).
Stanczyk, F.Z., et al., "Ethinyl Estradiol and $17\hat{I}^2$-Estradiol in Combined Oral Contraceptives: Pharmacokinetics, Pharmacodynamics and Risk assessment," Contraception 87(6):706-727, Elsevier, United States (2013).
Stanczyk, F.Z., et al., "therapeutically Equivalent Pharmacokinetic Profile Across Three Application Sites for Ag200-15 , A Novel Low-Estrogen Dose Contraceptive Patch," Contraception 87(6):744-749, Elsevier, United States (2013).
Stein, Emily A., et al., "Progesterone, SciFinder Scholar Search" 1-46, American Chemical Society & U.S. National Library of Medicine, Feb. 24, 2014.
Stein, Emily A., et al., "Progesterone Physical Properties," 1-46, American Chemical Society & U.S. National Library of Medicine, Feb. 24, 2014.
Stein, Emily A., et al., "Progesterone Physical Properties," 1-46, American Chemical Society & U.S. National Library of Medicine, Mar. 3, 2014.
Strickley, R.G., "Solubilizing Excipients in Oral and injectable formulations," Pharmaceutical research 21(2):201-230, Kluwer Academic/Plenum Publishers, United States (2004).
Strocchi, Antonino, Fatty Acid Composition, and Triglyceride Structure of Corn Oil, Hydrogenated Corn Oil, and Corn Oil Margarine, Journal of Food Science 47, pp. 36-39, (1981).
Struhar, M., et al., "Preparation of the Estradiol Benzoate injection Suspension," Ceskoslovenska farmacie 27(6):245-249, Ceskoslovenska Lekarska Spolecnost, Czech Republic (1978).
Sullivan, D.W.Jr., et al., "A review of the nonclinical safety of Transcutol®, a highly purified form of diethylene glycol monoethyl ether (DEGEE) used as a pharmaceutical excipient," Food and Chemical Toxicology 72:40-50, Elsevier Science Ltd, England (2014).
Sun, J. "D-Limonene : Safety and Clinical Applications," Alternative Medicine Review 12(3):259-264, Alternative Medicine Review, United States (2007).

Tahition Noni. "Body Balance Cream," http://products.lni.com/dominican_republic/sa_spanish/nonistore/producl/3438/3416/, 1 page, undated.
Tait, A.D., "Characterization of the Products From the Oxidation of Progesterone with Osmium Tetroxide," Steroids 20(5):531-542, Elsevier, United States (1972).
Takacs, M., et al., "The Light Sensitivity of Corticosteroids in Crystalline form Photochemical Studies 59 (1)," Pharmaceutica acta Helvetiae 66(5-6):137-140, Schweizerische Apotheker-Verein, Switzerland (1991).
Tan, Melvin, S., et al., "A Sensitive Method for the Determination of Progesterone in Human Plasma by LC-MS-MS, M1025," Cedra Corporation, Austin.
Tang, F.Y., et al., "Effect of Estrogen and Progesterone on the Development of Endometrial Hyperplasia in the Fischer Rat," Biology of Reproduction 31(2):399-413, Society for the Study of Reproduction, United States (1984).
Tas, M., et al., "Comparison of Antiproliferative Effects of Metformine and Progesterone on Estrogen-induced Endometrial Hyperplasia in Rats," Gynecological Endocrinology 29(4):311-314, Informa Healthcare, England (2013).
Tella, S.H., Gallagher, J.C., "Prevention and treatment of postmenopausal osteoporosis," The Journal of Steroid Biochemistry and Molecular Biology 142:155-170, Elsevier Ltd., United Kingdom (2014).
Thomas, J., et al., "The Effect of Water Solubility of Solutes on Their Flux Through Human Skin in Vitro: an Extended Flynn Database Fitted to the Roberts-Sloan Equation," International Journal of Pharmaceutics 339(1-2):157-167, Elsevier/North-Holland Biomedical Press., Netherlands (2007).
Thomas, P. "Characteristics of Membrane Progestin Receptor Alpha (Mpralpha) and Progesterone Membrane Receptor Component 1 (Pgmrc1) and their Roles in Mediating Rapid Progestin Actions," Frontiers in Neuroendocrinology 29(2):292-312, Academic Press, United States (2008).
Tripathi, R., et al., "Study of Polymorphs of Progesterone by Novel Melt Sonocrystallization Technique: A Technical Note," AAPS PharmSciTech 11(3):1493-1498, Elsevier/North-Holland Biomedical Press., Netherlands (2010).
Trommer, H. and Neubert, R.H., "Overcoming the Stratum Corneum: the Modulation of Skin Penetration A Review," Skin Pharmacology and Physiology 19(2):106-121, Karger, Switzerland (2006).
Ueda, T., et al., "Topical and Transdermal Drug Products," Pharmacopeial Forum 35(3):750-764, (2009).
USP, 401 Fats and Fixed Oils, Chemical Tests, Second Suplementto USP36-NF 31, pp. 6141-6151, (2013).
USP, Lauroyl Polyoxylglycerides, Saftey Data Sheet, US, 5611 Version #02, pp. 1-9, (2013).
"USP Monographs: Progesterone. USP29, accessed at www.pharmacopeia.cn/v29240/usp29nf24sO_m69870.html, accessed on Feb. 25, 2014."
USP, Official Monographs, Corn Oil, NF 31, pp. 1970-1971, (2013).
USP. Official Monographs, Lauroyl Polyoxylglycerides, NF 31, pp. 2064-2066, (2013).
USP, Official Monographs, Medium Chain Triglycerides, NF 31, pp. 2271-2272, (2013).
USP, Official Monographs, Mono- and Di-glycerides, NF 31, pp. 2101, (2013).
USP, USP Certificate-Corn Oil, Lot GOL404, Jul. 2013.
Utian, W.H., et al., "Relief of Vasomotor Symptoms and Vaginal Atrophy with Lower Doses of Conjugated Equine Estrogens and Medroxyprogesterone Acetate," Fertility and sterility 75(6):1065-1079, Elsevier for the American Society for Reproductive Medicine, United States (2001).
Voegtline, K.M. and Granger, D.A., "Dispatches From the interface of Salivary Bioscience and Neonatal Research," Frontiers in Endocrinology 5:25,Frontiers Research Foundation, Switzerland (2014).
Waddell, B.J. and Bruce, N.W., "The Metabolic Clearance of Progesterone in the Pregnant Rat : Absence of a Physiological Role for the Lung," Biology of Reproduction 40(6):1188-1193, Society for the Study of Reproduction, United States (1989).

(56) References Cited

OTHER PUBLICATIONS

Waddell, B.J. and Oleary, P.C., "Distribution and Metabolism of Topically Applied Progesterone in a Rat Model," The Journal of Steroid Biochemistry and Molecular Biology 80(4-5):449-455, Pergamon, England (2002).
Walter, L.M., et al., "The Role of Progesterone in Endometrial Angiogenesis in Pregnant and Ovariectomised Mice," Reproduction 129(6):765-777,Reproduction and Fertility by BioScientifica, England (2005).
Cole, W. and Julian, P.L., "A Study of the 22-Ketosteroids," Journal of the American Chemical Society 67(8):1369-1375, (1945).
Weber, E.J. "Corn Lipids," Cereal Chemistry Journal 55(5): 572-584, American Association of Cereal Chemists (1978).
Weber, M.T., et al., "Cognition and Mood in Perimenopause: A Systematic Review and Meta-Analysis," The Journal of Steroid Biochemistry and Molecular Biology 142:90-98, Pergamon, England (2014).
Whitehead, M.I., et al., "Absorption and Metabolism of Oral Progesterone," British medical journal 280(6217):825-827, British Medical Association, England (1980).
Duax, W.L., et al., "Conformation of Progesterone Side Chain: Conflict between X-ray Data and Force-Field Calculations," Journal of the American Chemical Society 103(22):6705-6712, (1981).
Wiranidchapong, Chutima et al., "Method of preparation does not affect the miscibility between steroid hormone and polymethacrylate," Thermochimica Acta 485(1-2):57-64, Elsevier B.V., Netherlands (2009).
Wood, C.E., et al., "Effects of estradiol with micronized progesterone or medroxyprogesterone acetate on risk markers for breast cancer in postmenopausal monkeys," Breast Cancer Research and Treatment 101:125-134, Springer Science+ Business Media B.V (2006), published online Jul. 14, 2006.
Wren, B.G., et al., "Effect of Sequential Transdermal Progesterone Cream on Endometrium , Bleeding Pattern , and Plasma Progesterone and Salivary Progesterone Levels in Postmenopausal Women," The Journal of the International Menopause Society 3(3):155-160, Informa Healthcare, England (2000).
Wu, X., et al., "Gene Expression Profiling of the Effects of Castration and Estrogen Treatment in the Rat Uterus," Biology of Reproduction 69(4):1308-1317, Society for the Study of Reproduction, United States (2003).
Yalkowsky, Samuel, H. , "Handbook of Acqueous Solubility Data," 1110-1111, CRC Press, United States.
Yalkowsky, S.H. and Valvani, S.C., "Solubility and Partitioning I: Solubility of Nonelectrolytes in Water," Journal of Pharmaceutical Sciences 69(8):912-922, Wiley-Liss, United States (1980).
Yue, W., et al., "Genotoxic Metabolites of Estradiol in Breast: Potential Mechanism of Estradiol induced Carcinogenesis," The Journal of Steroid Biochemistry and Molecular Biology 86(3-5):477-486, Pergamon, England (2003).
Zava, D. "Topical Progesterone Delivery and Levels in Serum, Saliva, Capillary Blood, and Tissues" Script:4-5.
Zava, D.T., et al., "Percutaneous absorption of progesterone," Maturitas 77:91-92, Elsevier/North Holland Biomedical Press, Ireland (2014).
Geelen, M.J.H., et al., "Dietary Medium-Chain Fatty Acids Raise and (n-3) Polyunsaturated Fatty Acids Lower Hepatic Triacylglycerol Synthesis in Rats," The Journal of Nutrition 125:2449-2456, American Institute of Nutrition, United States (1995).
Herman, A and Herman, A.P., "Essential oils and their constituents as skin penetration enhancer for transdermal drug delivery: a review," Journal of Pharmacy and Pharmacology 67(4):473-485, Royal Pharmaceutical Society, England (2014).
Manson, J.E., et al., "Menopausal Hormone Therapy and Health Outcomes During the Intervention and Extended Poststopping Phases of the Women's Health Initiative Randomized Trials," The Journal of the American Medical Association 310:1353-1368, American Medical Association, United States (2013).
Notice of Allowance, dated Dec. 10, 2014, in U.S. Appl. No. 14/099,562, Bernick, B.A., filed Dec. 6, 2013, 10 pages.
Notice of Allowance, dated Dec. 10, 2014, in U.S. Appl. No. 14/099,598, Bernick, B.A., filed Dec. 6, 2013, 8 pages.
Notice of Allowance, dated Dec. 15, 2014, in U.S. Appl. No. 14/099,623, Bernick, B.A., filed Dec. 6, 2013, 9 pages.
Notice of Allowance, dated Feb. 11, 2015, in U.S. Appl. No. 14/475,864, Bernick, B.A., filed Sep. 3, 2014, 9 pages.
Notice of Allowance, dated Feb. 13, 2015, in U.S. Appl. No. 14/475,814, Bernick, B.A., filed Sep. 3, 2014, 6 pages.
Notice of Allowance, dated Jan. 22, 2015, in U.S. Appl. No. 14/099,582, Bernick, B.A., filed Dec. 6, 2013, 5 pages.
Notice of Allowance, dated Jul. 14, 2014, in U.S. Appl. No. 14/099,545, Bernick, B.A., filed Dec. 6, 2013, 9 pages.
Notice of Allowance, dated Jul. 15, 2014, in U.S. Appl. No. 14/099,571, Bernick, B.A., filed Dec. 6, 2013, 11 pages.
Notice of Allowance, dated Nov. 26, 2014, in U.S. Appl. No. 14/099,612, Bernick, B.A., filed Dec. 6, 2013, 12 pages.
Notice of Allowance, dated Nov. 7, 2014, in U.S. Appl. No. 14/099,582, filed Dec. 6, 2013, 14 pages.
Office Action, dated Apr. 14, 2015, in U.S. Appl. No. 14/125,554, Bernick, B.A., filed Dec. 12, 2013, 9 pages.
Office Action, dated Apr. 7, 2015, in U.S. Appl. No. 14/624,051, Bernick B.A., filed Feb. 17, 2015, 10 pages.
Office Action, dated Dec. 8, 2014, in U.S. Appl. No. 14/106,655, Bernick, B.A., filed Dec. 13, 2013, 9 pages.
Office Action, dated Feb. 18, 2015, in U.S. Appl. No. 14/521,230, Bernick, B.A., filed Oct. 22, 2014, 8 pages.
Office Action, dated Jul. 18, 2014, in U.S. Appl. No. 14/099,623, Bernick, B.A., filed Dec. 6, 2013, 12 pages.
Office Action, dated Jul. 2, 2014, in U.S. Appl. No. 14/099,562, Bernick, B.A., filed Dec. 6, 2013, 9 pages.
Office Action, dated Jul. 3, 2014, in U.S. Appl. No. 14/099,598, Bernick, B.A., filed Dec. 6, 2013, 16 pages.
Office Action, dated Jul. 30, 2014, in U.S. Appl. No. 14/099,612, Bernick, B.A., filed Dec. 6, 2013, 12 pages.
Office Action, dated Jun. 17, 2014, in U.S. Appl. No. 14/099,582, Bernick, B.A., filed Dec. 6, 2013, 14 pages.
Office Action, dated Mar. 12, 2015, in U.S. Appl. No. 14/136,048, Bernick, B.A., filed Dec. 20, 2013, 24 pages.
Office Action, dated Mar. 27, 2014, in U.S. Appl. No. 14/099,562, Bernick, B.A., filed Dec. 6, 2013, 8 pages.
Office Action, dated Oct. 1, 2014, in U.S. Appl. No. 14/475,814, Bernick, B.A., filed Sep. 3, 2014, 6 pages.
Office Action, dated Oct. 2, 2014, in U.S. Appl. No. 14/475,864, Bernick, B.A., filed Sep. 3, 2014, 6 pages.
Portman, D., et al., "One-year treatment persistence with local estrogen therapy in postmenopausal women diagnosed as having vaginal atrophy," Menopause 22(11): 7 pages, The North American Menopause Society, United States (2015).
Rao, R. and Rao, S., "Intra Subject Variability of Progesterone 200 mg Soft Capsules in Indian Healthy Adult Postmenopausal Female Subjects under Fasting Conditions," Journal of Bioequivalence & Bioavailability 6(4):139-143, Open Access (2014).
Restriction Requirement, dated Apr. 14, 2015, in U.S. Appl. No. 13/843,428, Bernick, B.A., filed Mar. 15, 2013, 7 pages.
Restriction Requirement, dated Apr. 29, 2014, in U.S. Appl. No. 14/099,582, Bernick, B.A., filed Dec. 6, 2013, 9 pages.
Restriction Requirement, dated Dec. 5, 2014, in U.S. Appl. No. 14/125,554, Bernick, B.A., filed Dec. 12, 2013, 7 pages.
Restriction Requirement, dated Dec. 5, 2014, in U.S. Appl. No. 14/521,230, Bernick, B.A., filed Oct. 22, 2014, 9 pages.
Restriction Requirement, dated Jul. 3, 2014, in U.S. Appl. No. 14/106,655, Bernick, B.A., filed Dec. 13, 2013, 6 pages.
Restriction Requirement, dated Mar. 16, 2015, in U.S. Appl. No. 13/843,362, Bernick, B.A., filed Mar. 15, 2013, 7 pages.
Restriction Requirement, dated Mar. 20, 2014, in U.S. Appl. No. 14/099,612, Bernick, B.A., filed Dec. 6, 2013, 9 pages.
Restriction Requirement, dated Mar. 26, 2015, in U.S. Appl. No. 14/476,040, Bernick, B.A., filed Sep. 3, 2014, 7 pages.
Restriction Requirement, dated Mar. 28, 2014, in U.S. Appl. No. 14/099,571, Bernick, B.A., filed Dec. 6, 2013, 7 pages.
International Search Report and Written Opinion of International Application No. PCT/US2015/023041, Korean Intellectual Property Office, Republic of Korea, dated Jun. 30, 2015, 14 pages.

(56) References Cited

OTHER PUBLICATIONS

Sarpal, K., et al., "Self-Emulsifying Drug Delivery Systems: A Strategy to Improve Oral Bioavailability," *Current Research & Information on Pharmaceuticals Sciences* 11(3):42-49, Niper, India (Jul.-Sep. 2010).

Co-pending Application, U.S. Appl. No. 15/454,898, inventors Cacace, J., et al., filed Mar. 9, 2017 (Not Published).

\* cited by examiner

STEROID HORMONE COMPOSITIONS IN MEDIUM CHAIN OILS

CROSS-REFERENCE TO RELATED APPLICATIONS

This application claims priority to U.S. Provisional Application No. 62/317,056, entitled "STEROID HORMONE COMPOSITIONS IN MEDIUM CHAIN OILS," filed on Apr. 1, 2016, the entirety of which is hereby incorporated by reference.

FIELD

This disclosure relates to the field of steroid hormones and in particular, provides a pharmaceutical composition comprising a fully-solubilized steroid hormone having enhanced oral bioavailability compared with currently marketed pharmaceutical compositions.

BACKGROUND

Steroid hormones are vital constituents for the proper functioning of the human body and can be classified into five groups based on the receptors to which they bind, namely: glucocorticoids, mineralocorticoids, androgens, estrogens, and progestogens. It is known that steroid hormones aid in regulating metabolism, regulating water and salt function, regulating immune function, controlling inflammation, and developing sexual characteristics.

Despite their wide ranging biological activity, steroid hormones are difficult to deliver to a subject experiencing a disease or disorder where additional steroid hormone could help treat the disease or disorder. Progesterone, for example, has extremely poor oral bioavailability due to its limited water solubility. As a result, when given orally, it must be administered in a sufficiently high dose to obtain the desired pharmacokinetic profile. Higher dosages, however, are inherently less desirable as the greater the quantity dosed, the greater the risk that additional drug, beyond what the patient requires, could enter the bloodstream.

Progesterone is a naturally occurring C-21 steroid hormone belonging to the progestogen class. It is produced by the cells of the corpus luteum during the post-ovulatory luteal phase and to a lesser degree by the adrenal glands and the placenta during the second part of pregnancy. In women, progesterone levels are relatively low during the pre-ovulatory phase of the menstrual cycle, rise after ovulation, and are elevated during the luteal phase. Progesterone is commonly referred to as the "hormone of pregnancy" as it plays an important role in fetal development. Further, progesterone insufficiency can lead to premenstrual syndromes and menstrual irregularities.

Progesterone is used to support pregnancy in Assisted Reproductive Technology (ART) cycles, to control persistent ovulatory bleeding, to prepare the uterine lining in infertility therapy, and to support early pregnancy. Further, progesterone can be used for regularizing menstruation.

Progesterone is also used to oppose uterine hyperplasia and uterine cancer in women who are treating the symptoms of menopause with estrogen therapies.

Because progesterone does not dissolve in water and is poorly absorbed, currently marketed oral progesterone dosage forms administered to patients result in both intra- and inter-patient variability. To overcome the drawbacks of poor bioavailability associated with natural progesterone, researchers have used various synthetic progesterone derivatives such as medroxyprogesterone, norethisterone, methylestrenolone, chlormadinone acetate, 6-dehydroretroprogesterone, and lynestrenol. But, use of these derivatives is associated with side-effects not associated with natural progesterone.

SUMMARY

This disclosure is directed to pharmaceutical compositions capable of fully solubilizing a steroid hormone and that form micelles upon administration. The pharmaceutical compositions comprise a steroid hormone, various medium chain oils, a polysorbate, and, optionally, a terpene. In certain embodiments, the steroid hormone can be a progestogen, such as progesterone. In certain embodiments, the medium chain oils are predominantly C6-C14 medium chain oils. In certain embodiments, the optional terpene can be a monocyclic terpene such as d-limonene. In certain embodiments, the pharmaceutical composition comprises, in addition to the progesterone, a bio-identical estrogen. In certain embodiments, the estrogen is estradiol. The pharmaceutical compositions provide oral bioavailability, as measured by AUC, of the steroid hormone, which in certain embodiments is progesterone, of at least 125%, at least 150%, at least 175%, and in certain instances, at least 200% relative to a reference product such as PROMETRIUM.

This disclosure further provides methods of treating, inhibiting, or preventing a condition or disorder characterized by a steroid hormone deficiency, and in particular, conditions or disorders characterized by low levels of one or more steroid hormones, and particularly progesterone. The methods comprise administering to a subject a therapeutically effective amount of at least one pharmaceutical composition described herein.

In one embodiment, the present disclosure provides a pharmaceutical composition for providing enhanced oral bioavailability of progesterone, the pharmaceutical composition comprising: progesterone, a polysorbate, and a medium chain oil, wherein the medium chain oil comprises at least about 50 weight percent of a predominantly medium chain monoglyceride; and the progesterone is fully solubilized.

In certain embodiments, the medium chain oil comprises at least about 55 weight percent of a predominantly medium chain monoglyceride.

In other embodiments, the medium chain oil comprises at least about 60 weight percent of a predominantly medium chain monoglyceride.

In certain embodiments the medium chain oil comprises at least about 65 weight percent of a predominantly medium chain monoglyceride.

In certain embodiments, the medium chain oil comprises at least about 70 weight percent of a predominantly medium chain monoglyceride.

In certain embodiments, the polysorbate is selected from the group consisting of polysorbate 20, polysorbate 40, polysorbate 60, polysorbate 65, and polysorbate 80.

In certain embodiments, the pharmaceutical composition provides an oral bioavailability of at least about 150 percent as measured by an increase in AUC when compared to a reference product.

In certain embodiments, the pharmaceutical composition further comprises a polyoxyethylene hydrogenated castor oil.

In certain embodiments, the pharmaceutical composition further comprises a d-α-tocopherol polyethylene glycol succinate derivative.

In certain embodiments, the pharmaceutical composition further comprises a terpene.

In certain embodiments, the predominantly medium chain monoglyceride and the progesterone can be present at a weight ratio of about 10:1 to about 15:1.

In certain embodiments, the predominantly medium chain monoglyceride comprises at least about 60 weight percent of the medium chain oil.

In certain embodiments, the predominantly medium chain monoglyceride comprises at least about 70 weight percent of the medium chain oil.

In certain embodiments, the predominantly medium chain monoglyceride comprises at least about 80 weight percent of the medium chain oil.

In certain embodiments, the predominantly medium chain monoglyceride comprises at least about 90 weight percent of the medium chain oil.

In certain embodiments, the polysorbate is selected from the group consisting of polysorbate 20, polysorbate 40, polysorbate 60, polysorbate 65, and polysorbate 80.

In certain embodiments, the pharmaceutical composition provides an oral bioavailability of at least about 150 percent as measured by an increase in AUC when compared to a reference product.

In certain embodiments, the pharmaceutical composition further comprises a polyoxyethylene hydrogenated castor oil.

In certain embodiments, the pharmaceutical composition further comprises a d-α-tocopherol polyethylene glycol succinate derivative.

In certain embodiments, the pharmaceutical composition further comprises a terpene.

In certain embodiments, the present disclosure provides an oral, fully-solubilized progesterone pharmaceutical composition comprising: progesterone and a polysorbate in a weight ratio of from about 1:2 to about 2:1; and a medium chain oil comprising a mixture of medium chain mono- and diglycerides, the medium chain oil not containing more than about 10 weight percent triglycerides.

In certain embodiments, the polysorbate is selected from the group consisting of polysorbate 20, polysorbate 40, polysorbate 60, polysorbate 65, and polysorbate 80.

In certain embodiments, the pharmaceutical composition provides an oral bioavailability of at least about 150 percent as measured by an increase in AUC when compared to a reference product.

In certain embodiments, the pharmaceutical composition further comprises a polyoxyethylene hydrogenated castor oil.

In certain embodiments, the pharmaceutical composition further comprises a d-α-tocopherol polyethylene glycol succinate derivative.

In certain embodiments, the pharmaceutical composition further comprises a terpene.

In other embodiments, the present disclosure provides a method of treating a disease or condition associated with reduced progesterone levels, the method comprising administering to a subject in need thereof a pharmaceutical composition comprising: progesterone, a polysorbate, and a medium chain oil, wherein the medium chain oil comprises at least about 50 weight percent of a predominantly medium chain monoglyceride; and the progesterone is fully solubilized.

In certain embodiments, the method comprising administering to a subject in need thereof a pharmaceutical composition comprising: progesterone and a polysorbate in a weight ratio of from about 1:2 to about 2:1; and a medium chain oil comprising a mixture of medium chain mono- and diglycerides, the medium chain oil not containing more than about 10 weight percent triglycerides.

In certain embodiments, the disease or condition associated with reduced progesterone levels is selected from the group consisting of endometrial hyperplasia; secondary amenorrhea; prevention of preterm birth; and osteoporosis.

In certain embodiments, the disease or condition associated with reduced progesterone levels is menopause.

In addition to the foregoing, the present disclosure also provides a pharmaceutical composition for providing enhanced oral bioavailability of progesterone, the pharmaceutical composition comprising: progesterone, a polysorbate, and a medium chain oil, wherein the medium chain oil comprises at least about 50 weight percent of a first medium chain oil component; and the progesterone is fully solubilized.

In some embodiments, the medium chain oil further comprises a second medium chain oil component.

In some embodiments, the first medium chain oil component is a predominantly medium chain monoglyceride.

In some embodiments, the second medium chain oil component is a predominantly medium chain diglyceride.

In some embodiments, the predominantly medium chain diglyceride is a mixed or complex diglyceride.

BRIEF DESCRIPTION OF THE DRAWINGS/FIGURES

The foregoing summary, as well as the following detailed description, will be better understood when read in conjunction with the appended figures. For the purpose of illustration, the figures may describe the use of specific embodiments. It should be understood, however, that this disclosure is not limited to the precise embodiments discussed or described in these figures.

FIG. 1 is a graph of plasma concentration of progesterone vs. time for rats dosed with 20 μl of each of the various embodiments of the pharmaceutical composition described herein or 20 μl PROMETRIUM. Because of the way it is formulated, PROMETRIUM contains 400 mg progesterone/g of formulation. As such, the amount of progesterone dosed in rats treated with 20 μl PROMETRIUM far exceeded the amount of progesterone delivered to rats treated with 20 μl of the pharmaceutical compositions of this disclosure.

FIG. 2 is the log-linear version of FIG. 1.

FIG. 3 is a graph of plasma concentration of progesterone metabolite allopregnanolone sulfate vs. time for various embodiments of the pharmaceutical composition described herein and PROMETRIUM. As discussed above, the amount of progesterone administered to rats treated with 20 μl PROMETRIUM far exceeded the amount of progesterone administered to rats treated with 20 μl of the pharmaceutical compositions of this disclosure.

FIG. 4 is a log-linear version of FIG. 3.

FIG. 5 is a graph of plasma concentration of progesterone metabolite 20α-dihydroprogesterone vs. time for various embodiments of the pharmaceutical composition described herein and PROMETRIUM. As discussed above, the amount of progesterone administered to rats treated with 20 μl PROMETRIUM far exceeded the amount of progesterone administered to rats treated with 20 µl of the pharmaceutical compositions of this disclosure.

DETAILED DESCRIPTION

Definitions

Figure 1:
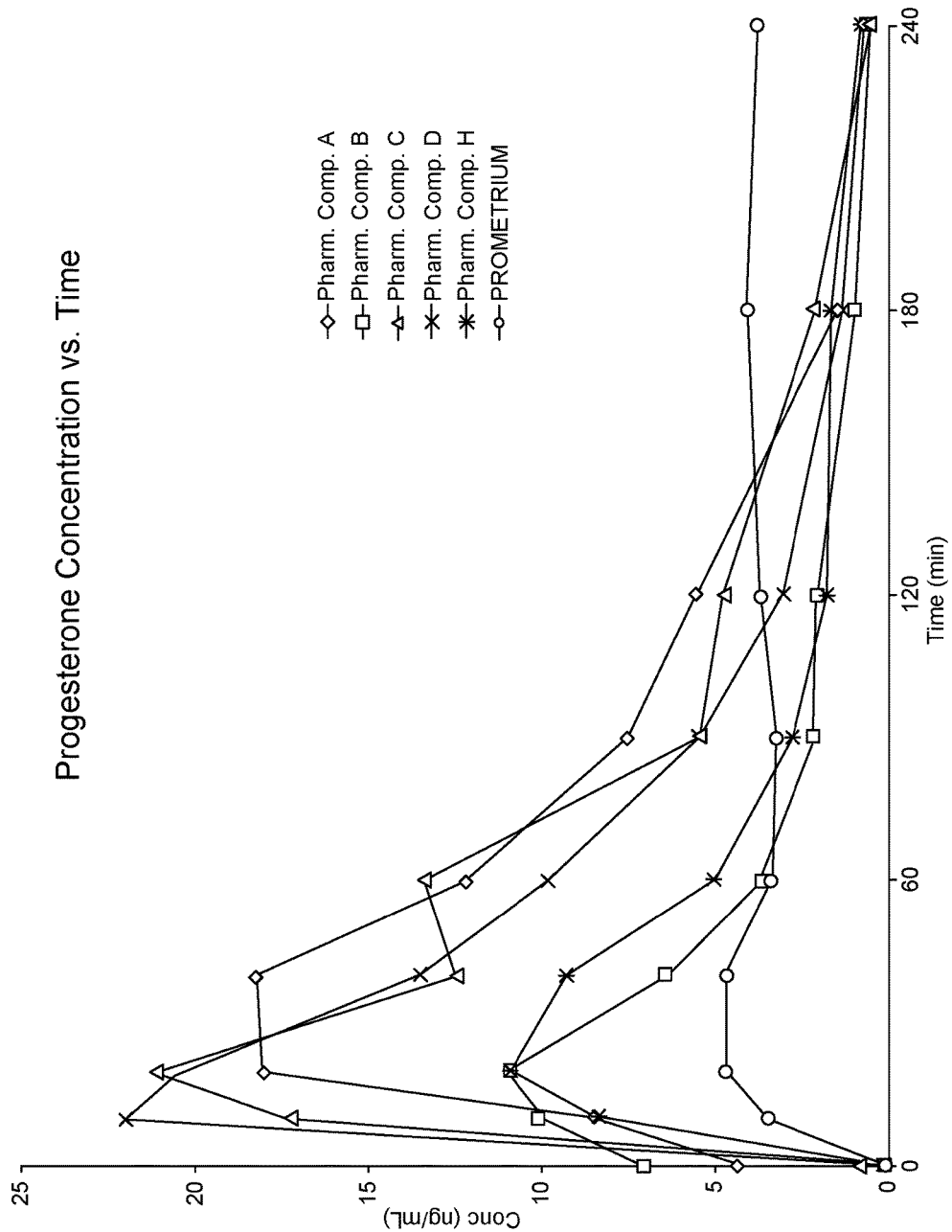
Figure 2:
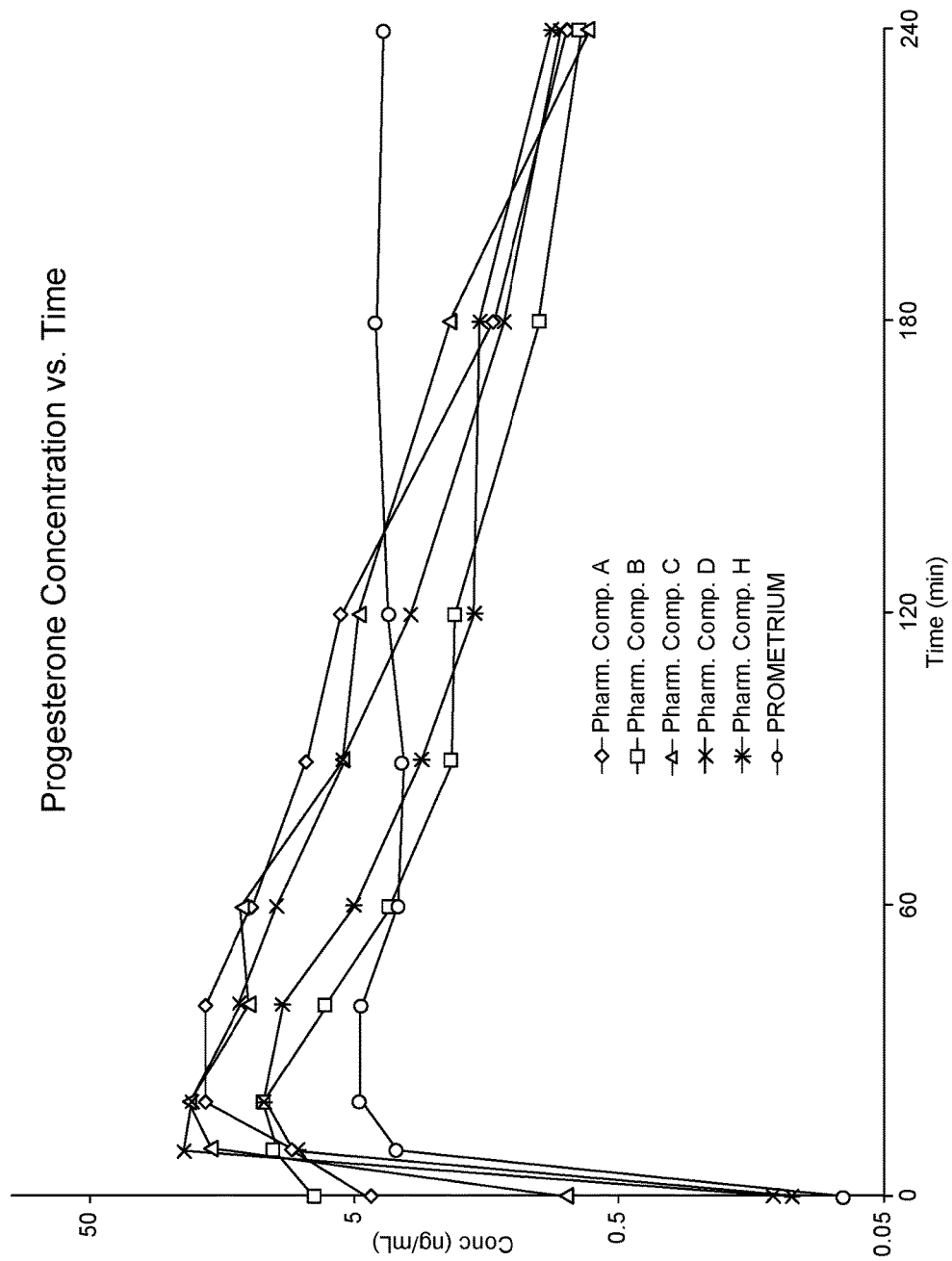

The singular forms "a," "an," and "the" include plural referents unless the context clearly dictates otherwise.

As used herein, the term "or" is a logical disjunction (i.e., and/or) and does not indicate an exclusive disjunction unless expressly indicated as such with the terms "either," "unless," "alternatively," and words of similar effect.

The term "area under the curve" ("AUC") refers to the area under the curve defined by changes in the blood concentration of an active pharmaceutical ingredient (e.g., progesterone or estradiol), or a metabolite of the active pharmaceutical ingredient, over time following the administration of a dose of the active pharmaceutical ingredient. "$AUC_{0-\infty}$" is the area under the concentration-time curve extrapolated to infinity following the administration of a dose. "$AUC_{0-t}$" is the area under the concentration-time curve from time zero to time t following the administration of a dose, wherein t is the last time point with a measurable concentration.

The term "$C_{max}$" refers to the maximum value of blood concentration shown on the curve that represents changes in blood concentrations of an active pharmaceutical ingredient (e.g., progesterone or estradiol), or a metabolite of the active pharmaceutical ingredient, over time.

The term "$t_{max}$" refers to the earliest time at which the blood concentration of an active pharmaceutical ingredient (e.g., progesterone or estradiol), or a metabolite of the active pharmaceutical ingredient is at its maximum value.

The term "bioavailability," which has the meaning defined in 21 C.F.R. § 320.1(a), refers to the rate and extent to which an active ingredient or active moiety is absorbed from a drug product and becomes available at the site of action. For drug products that are not intended to be absorbed into the bloodstream, bioavailability may be assessed by measurements intended to reflect the rate and extent to which the active ingredient or active moiety becomes available at the site of action. For example, bioavailability can be measured as the amount of active ingredient in the blood (serum or plasma) as a function of time. Pharmacokinetic (PK) parameters such as AUC, $C_{max}$, or $t_{max}$ may be used to measure and assess bioavailability.

The term "bioequivalent," has the meaning defined in 21 C.F.R. § 320.1(e) and refers to the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. Where there is an intentional difference in rate (e.g., in certain extended release dosage forms), certain pharmaceutical equivalents or alternatives may be considered bioequivalent if there is no significant difference in the extent to which the active ingredient or moiety from each product becomes available at the site of drug action. This applies only if the difference in the rate at which the active ingredient or moiety becomes available at the site of drug action is intentional and is reflected in the proposed labeling, is not essential to the attainment of effective body drug concentrations on chronic use, and is considered medically insignificant for the drug. In practice, two products are considered bioequivalent if the 90% confidence interval of the AUC or $C_{max}$ is within 80.00% to 125.00%.

The term "bio-identical hormone" refers to an active pharmaceutical ingredient that is structurally identical to a hormone naturally or endogenously found in the human body (e.g., progesterone or estradiol).

As used herein, the term "about" refers to ±10% of the noted value, unless otherwise specified, and unless the upper bound of the range would exceed 100% of the pharmaceutical composition, in which case the upper limit of the range is limited to 99.9%. Thus, and by way of example only, a pharmaceutical composition including about 10 weight percent of a given compound could have from 9 to 11 weight percent of the compound. Similarly, a pharmaceutical composition including about 95 weight percent of a given compound could have from 85.5 to 99.9 weight percent of the compound in the pharmaceutical composition.

The term "estradiol" refers to (17β)-estra-1,3,5(10)-triene-3,17-diol. Estradiol is also interchangeably called 17β-estradiol, oestradiol, or E2, and is found endogenously in the human body. As used herein, estradiol refers to the bio-identical or body-identical form of estradiol found in the human body having the structure:

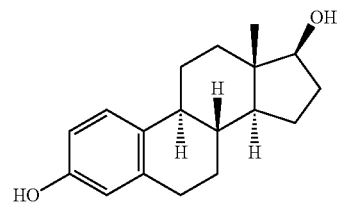

Estradiol is supplied in an anhydrous or hemi-hydrate form. For the purposes of this disclosure, the anhydrous form or the hemihydrate form can be substituted for the other by accounting for the water or lack of water according to well-known and understood techniques.

The term "solubilized estradiol" means that the estradiol or a portion thereof is solubilized or dissolved in the solubilizing agent(s) or the pharmaceutical compositions disclosed herein. Solubilized estradiol may include estradiol that is about 80% solubilized, about 85% solubilized, about 90% solubilized, about 95% solubilized, about 96% solubilized, about 97% solubilized, about 98% solubilized, about 99% solubilized or about 100% solubilized. In some embodiments, the estradiol is "fully solubilized" with all or substantially all of the estradiol being solubilized or dissolved in the solubilizing agent. Fully solubilized estradiol may include estradiol that is about 97% solubilized, about 98% solubilized, about 99% solubilized or about 100% solubilized. Solubility can be expressed as a mass fraction (% w/w, which is also referred to as wt %).

The term "glyceride" refers to an ester of glycerol (1,2,3-propanetriol) with acyl radicals of fatty acids and is also known as an acylglycerol. If only one position of the glycerol molecule is esterified with a fatty acid, a "monoglyceride" or "monoacylglycerol" is produced; if two positions are esterified, a "diglyceride" or "diacylglycerol" is produced; and if all three positions of the glycerol are esterified with fatty acids, a "triglyceride" or "triacylglycerol" is produced. A glyceride is "simple" if all esterified positions contain the same fatty acid; whereas a glyceride is "mixed" if the esterified positions are substituted with different fatty acids. A glyceride is "complex" if it contains a combination of simple and mixed glycerides. The carbons of the glycerol backbone are designated sn-1, sn-2 and sn-3, with sn-2 being the middle carbon and sn-1 and sn-3 being the end carbons of the glycerol backbone.

As used herein, the term "hormone deficiency" refers to a low level of one or more steroid hormones in a subject. Normal hormone levels will vary from subject to subject and can be determined via known methods. Low hormone levels may or may not be associated with symptoms including, but not limited to, fatigue, irregular bleeding, lowered libido, and depression. Conditions associated with progesterone deficiency include endometrial hyperplasia; secondary amenorrhea; prevention of preterm birth; menopause-related symptoms including, for example, vasomotor symptoms (e.g., hot flashes and night sweats); in relation to treatment of hypoestrogenism related symptoms including, for example and without limitation, vasomotor symptoms, sleep disturbances, mood changes, and vulvovaginal atrophy; and osteoporosis and other non-menopausal disease states or conditions treated with supplemental progesterone.

As used herein, the terms "host," "subject," and "patient" refer to any animal, including humans.

As used herein, the term "prevent" refers to the prophylactic treatment of a subject who is at risk of developing a condition (e.g., steroid hormone deficiency) resulting in a decrease in the probability that the subject will develop the condition.

The term "progesterone" refers to pregn-4-ene-3,20-dione. Progesterone is also interchangeably called P4 and is found endogenously in the human body. As used herein, progesterone refers to the bio-identical or body-identical form of progesterone found in the human body and having the structure:

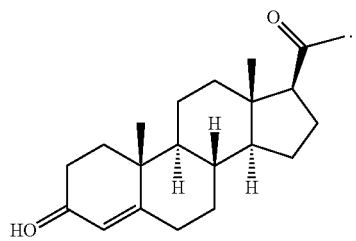

The term "solubilized progesterone" means that the progesterone or a portion thereof is solubilized or dissolved in the compositions disclosed herein. Solubilized progesterone may include progesterone that is about 80% solubilized, about 85% solubilized, about 90% solubilized, about 95% solubilized, about 96% solubilized, about 97% solubilized, about 98% solubilized, about 99% solubilized or about 100% solubilized. In some embodiments, the progesterone is "fully solubilized" with all or substantially all of the progesterone being solubilized or dissolved in a given composition. Fully solubilized progesterone may include progesterone that is about 97% solubilized, about 98% solubilized, about 99% solubilized or about 100% solubilized. Solubility can be expressed as a mass fraction (% w/w, which is also referred to as weight percent (wt %)).

The terms "micronized progesterone" and "micronized estradiol," as used herein, include micronized progesterone and micronized estradiol having an X50 particle size value below about 15 microns or having an X90 particle size value below about 25 microns. The term "X50" means that one-half of the particles in a sample are smaller in diameter than a given number. For example, micronized progesterone having an X50 of 5 microns means that, for a given sample of micronized progesterone, one-half of the particles have a diameter of less than 5 microns. Similarly, the term "X90" means that ninety percent (90%) of the particles in a sample are smaller in diameter than a given number.

The term "solubilizing agent" refers to an agent or combination of agents that solubilize an active pharmaceutical ingredient (e.g., progesterone or estradiol). For example and without limitation, suitable solubilizing agents include medium chain oils and other solvents and co-solvents that solubilize or dissolve an active pharmaceutical ingredient to a desirable extent. Solubilizing agents suitable for use in the pharmaceutical compositions disclosed herein are pharmaceutical grade solubilizing agents (e.g., pharmaceutical grade medium chain oils). It will be understood by those of skill in the art that other excipients or components can be added to or mixed with the solubilizing agent to enhance the properties or performance of the solubilizing agent or resulting pharmaceutical composition. Examples of such excipients include, but are not limited to, surfactants, emulsifiers, thickeners, colorants, flavoring agents, terpenes, etc. In some embodiments, the solubilizing agent is a medium chain oil and, in some other embodiments, the medium chain oil is combined with a co-solvent(s) or other excipient(s).

The term "medium chain" is used to describe the aliphatic chain length of fatty acid containing molecules. "Medium chain" specifically refers to fatty acids, fatty acid esters, or fatty acid derivatives that contain fatty acid aliphatic tails or carbon chains that contain, for example, 6 to 14 carbon atoms, 8 to 12 carbon atoms, or 8 to 10 carbon atoms.

The terms "medium chain fatty acid" and "medium chain fatty acid derivative" are used to describe fatty acids or fatty acid derivatives with aliphatic tails (i.e., carbon chains) having 6 to 14 carbon atoms. Fatty acids consist of an unbranched or branched aliphatic tail attached to a carboxylic acid functional group. Fatty acid derivatives include, for example, fatty acid esters and fatty acid containing molecules, including, without limitation, mono-, di- and triglycerides that include components derived from fatty acids. Fatty acid derivatives also include fatty acid esters of ethylene or propylene glycol. The aliphatic tails can be saturated or unsaturated (i.e., the latter having one or more double bonds between carbon atoms). In some embodiments, the aliphatic tails are saturated (i.e., no double bonds between carbon atoms). Medium chain fatty acids or medium chain fatty acid derivatives include those with aliphatic tails having 6-14 carbons, including those that are C6-C14, C6-C12, C8-C14, C8-C12, C6-C10, C8-C10, or others. Examples of medium chain fatty acids include, without limitation, caproic acid, caprylic acid, capric acid, lauric acid, myristic acid, and derivatives thereof. In certain embodiments, the medium chain fatty acids used to prepare the various medium chain oils described herein are C8, C10, or a combination thereof.

The term "oil," as used herein, refers to any pharmaceutically acceptable oil, especially medium chain oils, and specifically excluding peanut oil, that can suspend or solubilize bioidentical progesterone or estradiol, including starting materials or precursors thereof, including micronized progesterone and/or micronized estradiol as described herein.

The terms "treat," "treating," "treatment" and the like refer to any indicia of success in the treatment or amelioration of an injury, disease, or condition, including any objective or subjective parameter such as abatement; remission; diminishing of symptoms or making the injury, disease, or condition more tolerable to the patient; slowing in the rate of degeneration or decline; or improving a patient's physical or mental well-being. The treatment or amelioration of symptoms can be based on objective or subjective parameters, including the results of a physical examination, neuropsychiatric examinations, or psychiatric evaluation.

The term "medium chain oil" refers to an oil wherein the composition of the fatty acid fraction of the oil is substantially medium chain (i.e., C6 to C14) fatty acids, i.e., the composition profile of fatty acids in the oil is substantially medium chain. As used herein, "substantially" means that between 20% and 100% (inclusive of the upper and lower limits) of the fatty acid fraction of the oil is made up of medium chain fatty acids, i.e., fatty acids with aliphatic tails (i.e., carbon chains) having 6 to 14 carbons. In some embodiments, about 25%, about 30%, about 35%, about 40%, about 45%, about 50%, about 55%, about 60%, about 65%, about 70%, about 75%, about 85%, about 90% or about 95% of the fatty acid fraction of the oil is made up of medium chain fatty acids. Those of skill in the art will readily appreciate that the terms "alkyl content" or "alkyl distribution" of an oil can be used in place of the term "fatty acid fraction" of an oil in characterizing a given oil or solubilizing agent, and these terms are used interchangeably herein. As such, medium chain oils suitable for use in the pharmaceutical compositions disclosed herein include medium chain oils wherein the fatty acid fraction of the oil is substantially medium chain fatty acids, or medium chain oils wherein the alkyl content or alkyl distribution of the oil is substantially medium chain alkyls e.g., C6-C14 alkyls, but also including, for example, C6-C12 alkyls, C8-C12 alkyls, and C8-C10 alkyls. It will be understood by those of skill in the art that the medium chain oils suitable for use in the pharmaceutical compositions disclosed herein are pharmaceutical grade (e.g., pharmaceutical grade medium chain oils). Examples of medium chain oils include, for example and without limitation, medium chain fatty acids, medium chain fatty acid esters of glycerol (e.g., for example, mono-, di-, and triglycerides), medium chain fatty acid esters of propylene glycol, medium chain fatty acid derivatives of polyethylene glycol, and combinations thereof.

The term "ECN" or "equivalent carbon number" means the sum of the number of carbon atoms in the fatty acid chains of an oil, and can be used to characterize an oil as, for example, a medium chain oil or a long-chain oil. For example, tripalmitin (tripalmitic glycerol), which is a simple triglyceride containing three fatty acid chains of 16 carbon atoms, has an ECN of 3×16=48. Conversely, a triglyceride with an ECN=40 may have "mixed" fatty acid chain lengths of 8, 16, and 16; 10, 14, and 16; 8, 14, and 18; etc. Naturally occurring oils are frequently "mixed" with respect to specific fatty acids, but tend not to contain both long chain fatty acids and medium chain fatty acids in the same glycerol backbone. Thus, triglycerides with ECN's of 21-42 typically contain predominately medium chain fatty acids; while triglycerides with ECN's of greater than 43 typically contain predominantly long chain fatty acids. For example, the ECN of corn oil triglyceride in the USP would be in the range of 51-54. Medium chain diglycerides with ECN's of 12-28 will often contain predominately medium chain fatty chains, while diglycerides with ECN's of 32 or greater will typically contain predominately long chain fatty acid tails. Monoglycerides will have an ECN that matches the chain length of the sole fatty acid chain. Thus, monoglyceride ECN's in the range of 6-14 contain mainly medium chain fatty acids, and monoglycerides with ECN's 16 or greater will contain mainly long chain fatty acids.

The average ECN of a medium chain triglyceride oil is typically 21-42. For example, as listed in the US Pharmacopeia (USP), medium chain triglycerides have the following composition as the exemplary oil set forth in the table below:

| Fatty-acid Tail Length | % of oil | Exemplary Oil |
| --- | --- | --- |
| 6 | ≤2.0 | 2.0 |
| 8 | 50.0-80.0 | 70.0 |
| 10 | 20.0-50.0 | 25.0 |
| 12 | ≤3.0 | 2.0 |
| 14 | ≤1.0 | 1.0 | and would have an average ECN of 3*[(6*0.02)+(8*0.70)+(10*0.25)+(12*0.02)+(14*0.01)]=25.8. The ECN of the exemplary medium chain triglycerides oil can also be expressed as a range (per the ranges set forth in the USP) of 24.9-27.0. For oils that have mixed mono-, di-, and triglycerides, or single and double fatty acid glycols, the ECN of the entire oil can be determined by calculating the ECN of each individual component (e.g., C8 monoglycerides, C8 diglycerides, C10 monoglycerides, and C10 diglycerides) and taking the sum of the relative percentage of the component multiplied by the ECN normalized to a monoglyceride for each component. For example, an oil having C8 and C10 mono- and diglycerides shown in the table below has an ECN of 8.3, and is thus a medium chain oil.

| Fatty-acid Chain Length | % of oil | ECN as % of oil (chain length) × (% in oil) | ECN as % of oil normalized to monoglyceride |
| --- | --- | --- | --- |
| C8 monoglyceride | 47 | 8 × 0.47 = 3.76 | 3.76 |
| C10 monoglyceride | 8 | 10 × 0.08 = 0.8 | 0.8 |
| C8 diglyceride | 38 | 2 × (8 × 0.38) = 6.08 | 6.08/2 = 3.04 |
| C10 diglyceride | 7 | 2 × (10 × 0.07) = 1.4 | 1.4/2 = 0.7 |
| OIL ECN (normalized to monoglycerides) | | | 8.3 |

Expressed differently, ECN can be calculated as each chain length in the composition multiplied by its relative percentage in the oil: (8*0.85)+(10*0.15)=8.3.

The term "polysorbate" refers to a compound having the structure:

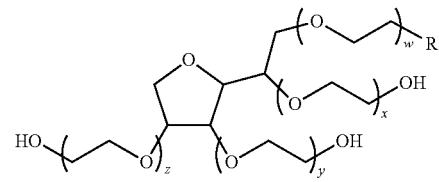

wherein w+x+y+z ranges from about 10 to about 50, and in particular embodiments, from about 10 to about 30, and wherein R is a C6-C18 fatty acid radical. Exemplary polysorbates within the scope of the present definition include, but are not limited to, polysorbate 20, polysorbate 40, polysorbate 60, polysorbate 65, and polysorbate 80.

The term "excipients," as used herein, refers to non-API ingredients such as solubilizing agents, anti-oxidants, oils, lubricants, dissolution aids, terpenes, and others used in formulating pharmaceutical products.

The phrase "therapeutically effective amount" refers to an amount of a pharmaceutical composition or of a given steroid hormone suitable to treat a particular symptom, disorder, or disease.

As used herein, the phrase "substantially pure" means that an identified component is at least about 90% pure by weight, in certain embodiments, at least about 95% pure by weight, and in still further embodiments, at least about 98% pure by weight.

As used herein, the phrase "steroid hormone" refers to progesterone, 17-hydroxyprogesterone, 5α-dihydroprogesterone, and estradiol.

As used herein, the term "d-limonene" refers to (4R)-1-methyl-4-(1-methylethenyl)-cyclohexene (CAS No. 5989-27-5), which is also known by synonyms including (+)-4-isopropenyl-1-methylcyclohexene, (+)-p-mentha-1,8-diene, and (R)-(+)-Limonene.

As used herein, the phrase "reference product" refers to PROMETRIUM for progesterone and ESTRACE tablets for estradiol, unless otherwise specified.

Pharmaceutical Compositions

The pharmaceutical compositions disclosed herein are capable of fully solubilizing steroid hormones, and in particular, progesterone and estradiol. Surprisingly, the pharmaceutical compositions in this disclosure provide a significantly better pharmacokinetic ("PK") profile for steroid hormones, and progesterone in particular, in a subject in need thereof than currently marketed pharmaceutical compositions, such as PROMETRIUM. The present pharmaceutical compositions achieve this enhanced PK profile despite containing from about ⅙ to about ⅛ as much progesterone as a comparable volume of PROMETRIUM. PROMETRIUM, for example, contains approximately 400 mg of progesterone per gram of formulation, while the pharmaceutical compositions provided in this disclosure contain, in certain embodiments, from about 10 to about 100 mg progesterone per gram of pharmaceutical composition, and in certain embodiments, about 60 mg progesterone per gram of pharmaceutical composition. Thus, and by way of example only, if a human subject were administered a 500 mg gel cap (a common gelcap size) of PROMETRIUM or a gelcap containing 500 mg of a pharmaceutical compositions disclosed herein comprising about 6 weight percent progesterone, the PROMETRIUM dose would contain 200 mg of progesterone compared to only 30 mg of progesterone in the exemplary pharmaceutical composition. Thus, the human receiving the exemplary composition would receive significantly less progesterone than the subject dosed with PROMETRIUM. Despite the discrepancy in the amount of progesterone dosed, it has now been surprisingly found, that the present compositions provide significantly increased bioavailability compared to PROMETRIUM. The enhanced bioavailability of progesterone or other steroid hormone in the present composition allows for a significant reduction in the amount progesterone, or other steroid hormone, that must be administered to a subject per dose to achieve the same or better results as PROMETRIUM.

Without wishing to be bound by any particular theory, it is believed that, in certain embodiments, the described pharmaceutical compositions form micelles upon administration that both protect the steroid hormone(s) from the digestive milieu and facilitate absorption of the steroid hormone(s) across the gut mucosa and into the blood stream, which may facilitate the enhanced bioavailability. That said, in other embodiments, and without wishing to be bound by any particular theory, the enhanced bioavailability observed in all of the present compositions may be due to the fully-solubilized nature of the progesterone present in the compositions and the absence of suspended (insoluble) progesterone. Thus, in some embodiments, the pharmaceutical composition can be characterized as a fully-solubilized progesterone pharmaceutical composition capable of forming micelles. Other embodiments, however, may comprise fully-solubilized progesterone but may not form micelles. In still other embodiments, the presence of both fully-solubilized progesterone and the formation of micelles together in the same pharmaceutical composition may result in an effect that further enhances the bioavailability of the progesterone above the bioavailability that would result if either only micelles were formed or only fully-solubilized progesterone were present.

Progesterone Compositions Capable of Forming Micelles

In certain embodiments, this disclosure provides a pharmaceutical composition providing enhanced oral bioavailability of a steroid hormone, such as progesterone, wherein the pharmaceutical composition can comprise a steroid hormone, such as progesterone, a polysorbate, and a medium chain oil.

In certain embodiments, the medium chain oil in the pharmaceutical composition can comprise at least about 50 weight percent of a medium chain monoglyceride. In certain embodiments, the medium chain monoglyceride and progesterone can be present at a weight ratio of about 8:1 to about 15:1, about 9:1 to about 15:1, about 9:1 to about 14:1, about 9:1 to about 13:1, about 9:1 to about 12:1, about 9:1 to about 11:1, or about 10:1. In particular embodiments, the medium chain monoglyceride and progesterone can be present in a ratio of about 10:1.

In certain embodiments, the polysorbate can comprise from about 1 weight percent to about 15 weight percent of the pharmaceutical composition and in particular embodiments, can be about 1 weight percent, about 2 weight percent, about 3 weight percent, about 4 weight percent, about 5 weight percent, about 6 weight percent, about 7 weight percent, about 8 weight percent, about 9 weight percent, about 10 weight percent, about 11 weight percent, about 12 weight percent, about 13 weight percent, about 14 weight percent, or about 15 weight percent of the pharmaceutical composition. In particular embodiments, the polysorbate can be about 5 weight percent or about 7 weight percent of the pharmaceutical composition.

In certain embodiments, the steroid hormone and the polysorbate present in the pharmaceutical composition are present in a weight ratio of about 1:2 to about 2:1.

In certain embodiments, the polysorbate can be selected from the group consisting of polysorbate 20, polysorbate 40, polysorbate 60, polysorbate 65, and polysorbate 80. These polysorbates are commercially available and well known to those of skill in the art. In certain embodiments, the polysorbate can be polysorbate 80. In even more particular embodiments, the polysorbate 80 can comprise about 5 weight percent or about 7 weight percent of the pharmaceutical composition.

In certain embodiments, the medium chain oil can comprise from about 50 weight percent to about 90 weight percent of the pharmaceutical composition. In particular embodiments, the medium chain oil can comprise from about 60 weight percent to about 90 weight percent, from about 65 weight percent to about 90 weight percent, from about 70 weight percent to about 90 weight percent, from about 75 weight percent to about 90 weight percent, or from about 75 weight percent to about 85 weight percent. In particular embodiments, the medium chain oil can comprise about 80 weight percent or about 85 weight percent of the pharmaceutical composition.

In certain embodiments, the medium chain oil can comprise a single medium chain oil component. In other embodiments, the medium chain oil can comprise a first medium chain oil component and a second medium chain oil component. In still further embodiments, the medium chain oil can comprise a first medium chain oil component, a second medium chain oil component, and a third medium chain oil component. In still further embodiments, the medium chain oil can comprise first, second, third and fourth; first, second, third, fourth, and fifth; or first, second, third, fourth, fifth, and sixth medium chain oil components.

In certain embodiments, the medium chain oil components themselves can be multi-component oils. For example, certain medium chain oils comprise a mixture of mono and diglycerides or a mixture of mono-, di-, and triglycerides, etc.

In particular embodiments, the medium chain oil can comprise a first medium chain oil component and a second medium chain oil component, with the first medium chain oil component comprising from about 30 weight percent to about 98 weight percent of the medium chain oil. In other embodiments, the first medium chain oil component can comprise from about 40 weight percent to about 95 weight percent of the medium chain oil. In still further embodiments, the first medium chain oil component can comprise from about 50 weight percent to about 90 weight percent of the medium chain oil.

In certain embodiments, the medium chain oil can comprise at least about 50 weight percent of a medium chain monoglyceride. In particular embodiments, the medium chain oil can comprise at least about at least about 55 weight percent of a medium chain monoglyceride, at least about at least about 60 weight percent of a medium chain monoglyceride, at least about 65 weight percent of a medium chain monoglyceride, at least about 70 weight percent of a medium chain monoglyceride, at least about 71 weight percent of a medium chain monoglyceride, at least about 72 weight percent of a medium chain monoglyceride, at least about 73 weight percent of a medium chain monoglyceride, at least about 74 weight percent of a medium chain monoglyceride, at least about 75 weight percent of a medium chain monoglyceride, at least about 76 weight percent of a medium chain monoglyceride, at least about 77 weight percent of a medium chain monoglyceride, at least about 78 weight percent of a medium chain monoglyceride, at least about 79 weight percent of a medium chain monoglyceride, at least about 80 weight percent of a medium chain monoglyceride, at least about 81 weight percent of a medium chain monoglyceride, at least about 82 weight percent of a medium chain monoglyceride, at least about 83 weight percent of a medium chain monoglyceride, at least about 84 weight percent of a medium chain monoglyceride, at least about 85 weight percent of a medium chain monoglyceride, at least about 86 weight percent of a medium chain monoglyceride, at least about 87 weight percent of a medium chain monoglyceride, at least about 88 weight percent of a medium chain monoglyceride, at least about 89 weight percent of a medium chain monoglyceride, or at least about 90 weight percent of a medium chain monoglyceride. In certain embodiments, the medium chain oil can comprise at least about 85 weight percent of a medium chain monoglyceride and in an even further embodiment, the medium chain oil can comprise at least about 90 weight percent of a medium chain monoglyceride.

The medium chain monoglyceride can be, predominantly, a single medium chain monoglyceride, such as glyceryl monocaproate, glyceryl monocaprylate, glyceryl monocaprate, glyceryl monolaurate, or glyceryl monomyristate. These monoglycerides are well known to those of ordinary skill in the art and are available in various commercial embodiments, including from ABITEC Corp, a division of Associated British Food, PLC, as CAPMUL 708G, CAPMUL 808G, CAPMUL MCM C8, and CAPMUL MCM C10. In particular embodiments, the medium chain monoglyceride can be, predominantly, a single medium chain monoglyceride such as glyceryl monocaproate, glyceryl monocaprylate, or glyceryl monocaprate. In specific embodiments, the medium chain monoglyceride can be, predominantly, glyceryl monocaprylate, commercially available as CAPMUL 708G.

In other embodiments, the medium chain monoglyceride can comprise a mixture of medium chain monoglycerides, such as a combination of two or more of glyceryl monocaproate, glyceryl monocaprylate, glyceryl monocaprate, glyceryl monolaurate, or glyceryl monomyristate. In particular embodiments, the mixture of medium chain monoglycerides can be a mixture of glyceryl monocaprylate and glyceryl monocaprate. In embodiments such as this, the glyceryl monocaprylate can comprise at least about 80 weight percent, at least about 85 weight percent, at least about 86 weight percent, at least about 87 weight percent, at least about 88 weight percent, at least about 88 weight percent, at least about 89 weight percent, or at least about 90 weight percent of the mixture of monoglycerides.

In certain embodiment, in addition to comprising a medium chain monoglyceride, the medium chain oil can further comprise one or more medium chain diglycerides. The one or more medium chain diglycerides can be simple diglycerides, such as glyceryl dicaproate, glyceryl dicaprylate, glyceryl dicaprate, glyceryl dilaurate, or glyceryl dimyristate. Alternatively, the one or more medium chain diglycerides can be mixed or complex diglycerides such as glyceryl caproate/caprylate, glyceryl caproate/caprate, glyceryl caproate/laurate, glyceryl caproate/myristate, glyceryl caprylate/caprate, glyceryl caprylate/laurate, glyceryl caprylate/myristate, glyceryl caprate/laurate, glyceryl caprate/myristate, or glyceryl laurate/myristate. In specific embodiments, the one or more medium chain diglycerides can be glyceryl caprylate/caprate. Exemplary commercially available medium chain diglycerides include, but are not limited to, CAPMUL 471, CAPMUL MCM, CAPMUL MCM NF, CAPMUL MCM EP, and IMWITOR 742. The CAPMULs are commercially available from ABITEC Corp.

The one or more medium chain diglycerides can comprise up to about 10 weight percent of the medium chain oil or alternatively from about 5 to about 10 weight percent of the pharmaceutical composition. In particular embodiments, the one or more medium chain diglycerides can comprise about 5 weight percent, about 6 weight percent, about 7 weight percent, about 8 weight percent, about 9 weight percent, or about 10 weight percent of the pharmaceutical composition. In specific embodiments, the one or more medium chain diglycerides can comprise about from about 8 to about 9 weight percent of the pharmaceutical composition, such as about 8 weight percent, about 8.1 weight percent, about 8.2 weight percent, about 8.3 weight percent, about 8.4 weight percent, about 8.5 weight percent, about 8.6 weight percent, about 8.7 weight percent, about 8.8 weight percent, about 8.9 weight percent, or about 9 weight percent of the pharmaceutical composition.

In certain embodiments, the one or more medium chain diglycerides can be glyceryl caprylate/caprate and the pharmaceutical composition can comprise about 8 weight percent to about 9 weight percent of this component. A commercially available component suitable for use in the pharmaceutical composition is CAPMUL MCM NF.

Because of the manner in which they are prepared, medium chain oils often contain some amount of material that is greater in length than C14. That said, this fraction is typically small and does not affect the overall performance of a given medium chain oil. As such, and in certain embodiments, the amount of material greater than C14 in a given medium chain oil comprises less than 20 weight percent, less than 15 weight percent, less than 5 weight percent, less than 2.5 weight percent, less than 1 weight percent, less than 0.5 weight percent, or less than 0.1 weight percent of a given medium chain oil.

Similarly, monoglycerides and diglycerides often contain di- and triglyceride components in the case of a monoglyceride or mono- and triglycerides in the case of diglycerides. The quantity of these components in a given mono- or diglyceride can vary, but is typically less than 20 weight percent, less than 15 weight percent, less than 5 weight percent, less than 2.5 weight percent, less than 1 weight percent, less than 0.5 weight percent, or less than 0.1 weight percent of the mono- or diglyceride. In all cases, the average ECN will be in the range of 12-28 for diglycerides and 6-14 for monoglycerides.

In addition to the components noted above, in certain embodiments, the pharmaceutical composition can optionally further include a polyoxyethylene hydrogenated castor oil. In particular embodiments, the polyoxyethylene hydrogenated castor oil can be referred to as a "PEG (or polyoxyl) X Hydrogenated Castor Oil," wherein X refers to the amount of pegylation. In particular embodiments, X can be a number from 1 to 100 and in certain embodiments, can be 7, 40, 40-45, or 60. Exemplary commercially available PEG/polyoxyl X hydrogenated castor oils include CREMOPHOR EL, CREMOPHOR RH40 (available commercially from BASF as polyoxyl 40 hydrogenated castor oil (also known as KOLLIPHOR RH 40)), ETOCAS 40, CRODURET 7, CRODURET 40, CRODURET 50, CRODURET 60, and KOLLIPHOR HS 15. In particular embodiments, the polyoxyethylene hydrogenated castor oil can be polyoxyl 40 hydrogenated castor oil (KOLLIPHOR RH 40).

When present, the polyoxyethylene hydrogenated castor oil can comprise from about 1 to about 10 weight percent of the pharmaceutical composition. In particular embodiments, the polyoxyethylene hydrogenated castor oil can comprise from about 2 to about 9 weight percent of the pharmaceutical composition, from about 3 to about 7 weight percent of the pharmaceutical composition, from about 4 to about 6 weight percent of the pharmaceutical composition, or about 4 to about 5 weight percent of the pharmaceutical composition. In particular embodiments, the polyoxyethylene hydrogenated castor oil can comprise about 4 weight percent of the pharmaceutical composition, about 4.1 weight percent of the pharmaceutical composition, about 4.2 weight percent of the pharmaceutical composition, about 4.3 weight percent of the pharmaceutical composition, about 4.4 weight percent of the pharmaceutical composition, about 4.5 weight percent of the pharmaceutical composition, about 4.6 weight percent of the pharmaceutical composition, about 4.7 weight percent of the pharmaceutical composition, about 4.8 weight percent of the pharmaceutical composition, or about 4.9 weight percent of the pharmaceutical composition.

In other embodiments, the pharmaceutical composition can optionally include a d-α-tocopherol polyethylene glycol succinate (TPGS) derivative having the formula:

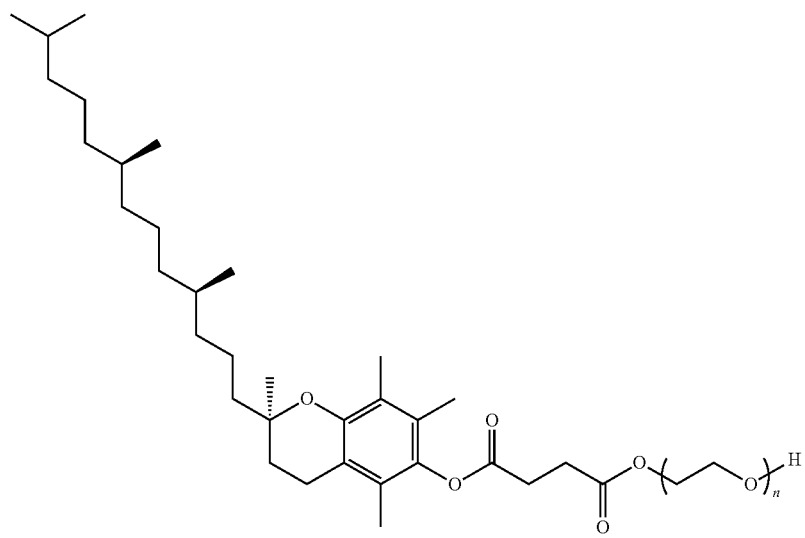

wherein n can range from 1 to about 100, and in particular embodiments, from about 1 to about 50 or about 1 to about 25. In particular embodiments, the D-α-Tocopherol polyethylene glycol succinate derivative can be d-α-tocopherol polyethylene glycol 1000 succinate, also referred to as TPGS-1000 (n≈22).

The d-α-tocopherol polyethylene glycol succinate derivative, when present, can comprise from about 0.1 weight percent to about 5 weight percent of the pharmaceutical composition and in particular embodiments about 1 weight percent, about 1.5 weight percent, about 1.75 weight percent, about 2 weight percent, about 2.1 weight percent, about 2.2 weight percent, about 2.3 weight percent, about 2.4 weight percent, about 2.5 weight percent, about 2.75 weight percent, about 3 weight percent, about 3.25 weight percent, about 3.5 weight percent, about 3.75 weight percent, about 4 weight percent, about 4.25 weight percent, about 4.5 weight percent, or about 4.75 weight percent of the pharmaceutical composition. In certain embodiments, the d-α-tocopherol polyethylene glycol succinate derivative can comprise about 2.3 weight percent of the pharmaceutical composition. In other embodiments, the pharmaceutical composition can comprise TPGS-1000 at about 2.3 weight percent.

Generally speaking, and in certain embodiments, when the pharmaceutical composition includes a d-α-tocopherol polyethylene glycol succinate derivative, the pharmaceutical composition does not include a polyoxyethylene hydrogenated castor oil. Similarly, and in certain embodiments, when the pharmaceutical composition includes a polyoxyethylene hydrogenated castor oil, the pharmaceutical composition does not include a d-α-tocopherol polyethylene glycol succinate derivative.

As noted at the outset, the pharmaceutical compositions of the present disclosure are believed to form micelles after oral administration. Micelle formation can be observed by adding the pharmaceutical compositions described herein to water or other aqueous-based fluid such as simulated gastric fluid (SGF). The size or size distribution of the micelles resulting from mixing the pharmaceutical compositions with water or SGF can be measured using photon correlation spectroscopy. In certain embodiments, the particles can have a size distribution ranging from about 1 nm to about 1400 nm in water, or from about 130 nm to about 465 nm in water, or from about 100 nm to about 210 nm in water.

In certain embodiments, the micelles can have a zeta potential (mV) ranging from about −10 to about −30 mV. In certain embodiments, the zeta potential of the micelles can be about −10 mV, about −11 mV, about −12 mV, about −13 mV, about −14 mV, about −15 mV, about −16 mV, about −17 mV, about −18 mV, about −19 mV, about −20 mV, about −21 mV, about −22 mV, about −23 mV, about −24 mV, about −25 mV, about −26 mV, about −27 mV, about −28 mV, about −29 mV, or about −30 mV. In certain embodiments, the zeta potential can be about −16 to about −17 mV. In other embodiments, the zeta potential can be about −18 to about −19 mV. In still other embodiments, the zeta potential can be about −20 to about −21 mV.

Non-Micelle Forming Pharmaceutical Compositions

In another embodiment, the present disclosure provides non-micelle forming, fully-solubilized steroid hormone pharmaceutical compositions. These compositions comprise one or more steroid hormones, and in particular embodiments, progesterone and a medium chain oil.

In certain embodiments, the medium chain oil in the pharmaceutical composition can comprise at least about 50 weight percent of a medium chain monoglyceride. In certain embodiments, the medium chain monoglyceride and progesterone can be present at a weight ratio of about 8:1 to about 15:1, about 9:1 to about 15:1, about 9:1 to about 15:1, about 10:1 to about 15:1, about 11:1 to about 15:1, about 12:1 to about 15:1, about 13:1 to about 15:1, or about 14:1. In particular embodiments, the medium chain monoglyceride and progesterone can be present in a ratio of about 14:1.

In certain embodiments of the non-micelle forming pharmaceutical composition, the medium chain oil can comprise from about 50 weight percent to about 95 weight percent of the pharmaceutical composition. In particular embodiments, the medium chain oil can comprise from about 60 weight percent to about 95 weight percent, from about 65 weight percent to about 95 weight percent, from about 70 weight percent to about 95 weight percent, from about 75 weight percent to about 95 weight percent, or from about 85 weight percent to about 95 weight percent. In particular embodiments, the medium chain oil can comprise about 94 weight percent of the non-micelle forming pharmaceutical composition.

In certain embodiments, the medium chain oil can comprise a single medium chain oil component. In other embodiments, the medium chain oil can comprise a first medium chain oil component and a second medium chain oil component. In still further embodiments, the medium chain oil can comprise a first medium chain oil component, a second medium chain oil component, and a third medium chain oil component. In still further embodiments, the medium chain oil can comprise first, second, third and fourth; first, second, third, fourth, and fifth; or first, second, third, fourth, fifth, and sixth medium chain oil components.

In certain embodiments, the medium chain oil components themselves can be multi-component oils. For example, certain medium chain oils comprise a mixture of mono and diglycerides or a mixture of mono-, di-, and triglycerides, etc.

In particular embodiments, the medium chain oil can comprise a first medium chain oil component and a second medium chain oil component, with the first medium chain oil component comprising from about 30 weight percent to about 98 weight percent of the medium chain oil. In other embodiments, the first medium chain oil component can comprise from about 40 weight percent to about 95 weight percent of the medium chain oil. In still further embodiments, the first medium chain oil component can comprise from about 50 weight percent to about 90 weight percent of the medium chain oil.

In certain embodiments, the medium chain oil can comprise at least about 50 weight percent of a medium chain monoglyceride. In particular embodiments, the medium chain oil can comprise at least about at least about 55 weight percent of a medium chain monoglyceride, at least about at least about 60 weight percent of a medium chain monoglyceride, at least about 65 weight percent of a medium chain monoglyceride, at least about 70 weight percent of a medium chain monoglyceride, at least about 71 weight percent of a medium chain monoglyceride, at least about 72 weight percent of a medium chain monoglyceride, at least about 73 weight percent of a medium chain monoglyceride, at least about 74 weight percent of a medium chain monoglyceride, at least about 75 weight percent of a medium chain monoglyceride, at least about 76 weight percent of a medium chain monoglyceride, at least about 77 weight percent of a medium chain monoglyceride, at least about 78 weight percent of a medium chain monoglyceride, at least about 79 weight percent of a medium chain monoglyceride, at least about 80 weight percent of a medium chain monoglyceride, at least about 81 weight percent of a medium chain monoglyceride, at least about 82 weight percent of a medium chain monoglyceride, at least about 83 weight percent of a medium chain monoglyceride, at least about 84 weight percent of a medium chain monoglyceride, at least about 85 weight percent of a medium chain monoglyceride, at least about 86 weight percent of a medium chain monoglyceride, at least about 87 weight percent of a medium chain monoglyceride, at least about 88 weight percent of a medium chain monoglyceride, at least about 89 weight percent of a medium chain monoglyceride, at least about 90 weight percent of a medium chain monoglyceride, or at least about 90 weight percent of a medium chain monoglyceride. In certain embodiments, the medium chain oil can comprise at least about 90 weight percent of a medium chain monoglyceride.

The medium chain monoglyceride can be, predominantly, a single medium chain monoglyceride, such as glyceryl monocaproate, glyceryl monocaprylate, glyceryl monocaprate, glyceryl monolaurate, or glyceryl monomyristate. These monoglycerides are well known to those of ordinary skill in the art and are available in various commercial embodiments, including from ABITEC Corp, a division of Associated British Food, PLC, as CAPMUL 708G, CAPMUL 808G, CAPMUL MCM C8, and CAPMUL MCM C10. In particular embodiments, the medium chain monoglyceride can be, predominantly, a single medium chain monoglyceride such as glyceryl monocaproate, glyceryl monocaprylate, or glyceryl monocaprate. In specific embodiments, the medium chain monoglyceride can be, predominantly, glyceryl monocaprylate, commercially available as CAPMUL 708G.

In other embodiments, the medium chain monoglyceride can comprise a mixture of medium chain monoglycerides, such as a combination of two or more of glyceryl monocaproate, glyceryl monocaprylate, glyceryl monocaprate, glyceryl monolaurate, or glyceryl monomyristate. In particular embodiments, the mixture of medium chain monoglycerides can be a mixture of glyceryl monocaprylate and glyceryl monocaprate. In embodiments such as this, the glyceryl monocaprylate can comprise at least about 80 weight percent, at least about 85 weight percent, at least about 86 weight percent, at least about 87 weight percent, at least about 88 weight percent, at least about 88 weight percent, at least about 89 weight percent, or at least about 90 weight percent of the mixture of monoglycerides.

In certain embodiment, in addition to comprising a medium chain monoglyceride, the medium chain oil can further comprise one or more medium chain diglycerides. The one or more medium chain diglycerides can be simple diglycerides, such as glyceryl dicaproate, glyceryl dicaprylate, glyceryl dicaprate, glyceryl dilaurate, or glyceryl dimyristate. Alternatively, the one or more medium chain diglycerides can be mixed or complex diglycerides such as glyceryl caproate/caprylate, glyceryl caproate/caprate, glyceryl caproate/laurate, glyceryl caproate/myristate, glyceryl caprylate/caprate, glyceryl caprylate/laurate, glyceryl caprylate/myristate, glyceryl caprate/laurate, glyceryl caprate/myristate, or glyceryl laurate/myristate. In specific embodiments, the one or more medium chain diglycerides can be glyceryl caprylate/caprate. Exemplary commercially available medium chain diglycerides include, but are not limited to, CAPMUL 471, CAPMUL MCM, CAPMUL MCM NF, CAPMUL MCM EP, and IMWITOR 742. The CAPMULs are commercially available from ABITEC Corp.

The one or more medium chain diglycerides can comprise up to about 10 weight percent of the medium chain oil or alternatively from about 5 to about 10 weight percent of the pharmaceutical composition. In particular embodiments, the one or more medium chain diglycerides can comprise about 5 weight percent, about 6 weight percent, about 7 weight percent, about 8 weight percent, about 9 weight percent, or about 10 weight percent of the pharmaceutical composition. In specific embodiments, the one or more medium chain diglycerides can comprise about from about 8 to about 9 weight percent of the pharmaceutical composition, such as about 8 weight percent, about 8.1 weight percent, about 8.2 weight percent, about 8.3 weight percent, about 8.4 weight percent, about 8.5 weight percent, about 8.6 weight percent, about 8.7 weight percent, about 8.8 weight percent, about 8.9 weight percent, or about 9 weight percent of the pharmaceutical composition.

In certain embodiments, the one or more medium chain diglycerides can be glyceryl caprylate/caprate and the pharmaceutical composition can comprise about 8 weight percent to about 10 weight percent of this component. A commercially available component suitable for use in the pharmaceutical composition is CAPMUL MCM NF.

Excluded Ingredients

In certain embodiments, the pharmaceutical compositions described in this disclosure are completely or substantially free of animal oils, vegetable oils, fractionated vegetable oils, all Omega-3 free fatty acids, all Omega-3 fatty acid esters, EPA fatty acid esters, and DHA fatty acid esters. Exemplary excluded animal oils include, but are not limited to, fish liver oils, shark oil, and mink oil. Exemplary excluded fractionated vegetable oils include, but are not limited to, fractionated coconut oils. Exemplary excluded vegetable oils include soy bean oil, safflower seed oil, corn oil, olive oil, cottonseed oil, arachis oil, sunflower seed oil, coconut oil, palm oil, and rape seed oil. Exemplary excluded Omega-3 free fatty acids and Omega-3 fatty acid esters, include, for example, hexadecatrienoic acid, α-linolenic acid, stearidonic acid, eicosatrienoic acid, eicosapentaenoic acid, heneicosapentaenoic acid, docosapentenoic acid, docosahexaenoic acid, tetracosapentenoic acid, tetracosahexaenoic acid, combinations thereof, and esters thereof Steroid Hormones In certain embodiments, the pharmaceutical compositions in this disclosure can comprise from about 0.025 weight percent to about 15 weight percent of a steroid hormone. In certain embodiments, the pharmaceutical composition can comprise from about 0.025 weight percent steroid hormone to about 10 weight percent steroid hormone, from about 1 to about 10 weight percent steroid hormone, about 1 to about 9 weight percent steroid hormone, from about 1 to about 8 weight percent steroid hormone, from about 1 to about 7 weight percent steroid hormone, from about 2 to about 7 weight percent steroid hormone, from about 3 to about 7 weight percent steroid hormone, from about 4 to about 7 weight percent steroid hormone, from about 5 to about 7 weight percent steroid hormone, or about 6 weight percent steroid hormone. In certain embodiments, the pharmaceutical compositions of this disclosure can comprise about 6 weight percent steroid hormone, and in even still other embodiments, about 6 weight percent progesterone. In further embodiments, progesterone can be the sole active ingredient in the pharmaceutical composition.

The steroid hormone, and in particular embodiments, progesterone, can be partially solubilized (i.e., less than about 80% solubilized), solubilized, or fully solubilized, depending upon the specific components of the composition. In typical embodiments, the steroid hormone is at least solubilized and in certain embodiments, fully solubilized in the pharmaceutical composition. In some embodiments, the pharmaceutical composition is saturated such that additional steroid hormone will not dissolve. In some embodiments, the pharmaceutical composition contains both solubilized and suspended (insoluble) steroid hormone. That said, and more typically, the steroid hormone is at least about 80%, at least about 85%, at least about 90%, at least about 95%, at least about 99%, or 100% solubilized in the pharmaceutical composition at a given concentration. In certain embodiments, the steroid hormone, and in particular progesterone, is fully solubilized, i.e., at least about 95 percent solubilized, at least about 98% solubilized, or at least about 99% solubilized as measured according to the methodology described below. However, in other embodiments, the progesterone can be solubilized or only partially solubilized.

The solubility of a given steroid hormone can be measured using standard techniques by weighing a piece of filter paper, placing the weighed filter paper in a buchner funnel (porcelain or glass with a glass frit), and drawing a known quantity of pharmaceutical composition through the filter paper using vacuum (such as with a side-arm flask fitted with a neoprene collar). After drying for an appropriate period of time (either at room temperature or at elevated temperature), the filter paper is reweighed. The amount of steroid hormone on the filter paper is calculated and the amount or percentage of solubilized and insoluble steroid hormone is calculated.

In certain embodiments, the steroid hormone is progesterone and in particular embodiments, the progesterone can comprise about 6 weight percent of the pharmaceutical composition. In some embodiments, progesterone is the sole active ingredient in the pharmaceutical composition.

In certain embodiments, the steroid hormone can be a combination of progesterone and estradiol. In certain embodiments, the steroid hormone is a progestogen, including, but not limited to bio-identical progesterone or progesterone analogs. In certain embodiments the steroid hormone is an estrogen, including estradiol, estrone, estriol, or estrogen analog.

Although the steroid hormone used to formulate the pharmaceutical composition can have any particle size, in certain embodiments, the steroid hormone can have an average particle size of less than about 100 microns. In certain embodiments, the steroid hormone can be micronized. Without wishing to be bound by any particular theory, it is believed that steroid hormones having a smaller average particle size will be more soluble in the pharmaceutical composition.

Terpenes

All of the pharmaceutical compositions described in this disclosure can optionally include a terpene. Terpenes are the primary constituents of the essential oils of many types of plants and flowers and are typically formed directly from one or more isoprene ($C_5H_8$) units. Terpenes can be naturally occurring or prepared synthetically. Terpenes can be obtained from their natural source, for example, isolated from a natural oil such as citrus oil or orange oil, and optionally purified to be substantially pure, or synthesized chemically.

In certain embodiments, the terpene can be a terpenoid. Examples of terpenes are provided, for example, in Dev et al., "CRC Handbook of Terpenoids: Acyclic, Monocyclic, Bicyclic, Tricyclic, and Tetracyclic Terpenoids" (1989) CRC Press Inc.; Hanson, J. R., Annu. Rep. Prog. Chem., Sect. B: Org. Chem., (1985) 82, 353-375; and Degenhardt et al., Phytochemistry (2009) 70:1621-1637. Each of these references is hereby incorporated by reference in its entirety.

The optional terpene can be linear or cyclic (including aromatic). A cyclic terpene can be a monocyclic terpene or a bicyclic terpene. In a particular embodiment, the cyclic terpene can be a monocyclic terpene. In certain embodiments, the cyclic terpene can be non-aromatic. Examples of cyclic terpenes include, without limitation, limonene (as d-limonene, l-limonene, or a mixture thereof), phellandrene (alpha or beta), camphor, menthol, menthene, carvone, terpinene (alpha, beta, or gamma), terpineol (alpha, beta, or gamma), alpha-ionone, thujone, and derivatives thereof. In certain embodiments, the cyclic terpene is limonene, menthene, menthol, phellandrene, terpinene, or terpineol. In some embodiments, the optional terpene can be d-limonene.

In certain embodiments, when the terpene is present, the terpene can comprise from about 0.5 weight percent to about 10 weight percent of the pharmaceutical composition; from about 1 weight percent to about 10 weight percent of the pharmaceutical composition; from about 2 weight percent to about 9 weight percent of the pharmaceutical composition; from about 3 weight percent to about 8 weight percent of the pharmaceutical composition; from about 4 weight percent to about 8 weight percent of the pharmaceutical composition; from about 5 weight percent to about 7 weight percent of the pharmaceutical composition, or about 6 weight percent of the pharmaceutical composition.

In certain embodiments, the optional terpene is d-limonene and is present in any of the amounts noted above. In other embodiments, the optional terpene is d-limonene and is present at about 6 weight percent of the pharmaceutical composition.

Antioxidants

In certain embodiments, the pharmaceutical compositions can further include an antioxidant such as α-tocopherol acetate, acetone sodium bisulfite, acetylcysteine, ascorbic acid, ascorbyl palmitate, butylated hydroxyanisole (BHA), butylated hydroxytoluene (BHT), cysteine, cysteine hydrochloride, α-tocopherol, dithiothreitol, monothioglycerol, nordihydroguaiaretic acid, propyl gallate, sodium bisulfite, sodium formaldehyde sulfoxylate, sodium metabisulfite, sodium sulfite, sodium thiosulfate, thiourea, tocopherol, or any combination thereof. In particular embodiments, the antioxidant is BHT.

The antioxidant can be included in an amount appropriate to inhibit oxidation of any, some, or all of the components of the pharmaceutical composition for a desired period of time. For example, the antioxidant can inhibit oxidation of any of the steroid hormone(s) present in the pharmaceutical composition, the medium chain oil, the polysorbate, the polyoxyethylene hydrogenated castor oil, the D-α-Tocopherol polyethylene glycol succinate derivative, or the terpene to the extent these components are present in the composition. In certain embodiments, the antioxidant is present to inhibit the oxidation of the terpene, which in certain embodiments, can be d-limonene. In certain embodiments, the BHT is present in the pharmaceutical composition at from about 0.01 to about 0.1 weight percent. In other embodiments, the BHT is present at about 0.03 weight percent.

Methods of Treating Hormone Deficiencies

In certain embodiments, this disclosure provides methods for treating one or more conditions associated with hormone deficiency in a subject. The methods comprise orally administering to a subject in need thereof an effective amount of the pharmaceutical composition described herein.

In some embodiments, the condition being treated can be a progesterone deficiency. In some embodiments, the condition can be endometrial hyperplasia, secondary amenorrhea, hot flashes, night sweats, sleep disturbances, mood changes, or osteoporosis. In some embodiments, the pharmaceutical composition disclosed herein can be used to counteract side effects of estradiol in subjects receiving estradiol therapy.

In some embodiments, the condition being treated can be an estrogen deficiency.

In some embodiments, the condition can be hot flashes, night sweats, sleep disturbances, mood changes, vulvovaginal atrophy, or osteoporosis.

In certain embodiments, the pharmaceutical composition can be administered to a subject in need thereof, such that the subject receives steroid hormone, and in particular embodiments, progesterone, in an amount ranging from about 0.1 mg to about 1 g; about 1 mg to about 600 mg; or about 10 mg to about 500 mg. In certain specific embodiments, the steroid hormone is progesterone.

In other embodiments, the progesterone can be administered to a subject in need thereof, and in particular a human, using the pharmaceutical compositions in this disclosure so that the subject/human in need thereof receives an amount of progesterone ranging from about 10 mg to about 500 mg, and in certain embodiments, about 10 mg, about 15 mg, about 20 mg, about 25mg, 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, or any range encompassing any of the noted values.

In particular embodiments, the amount of progesterone administered per dose using the pharmaceutical composition in this disclosure to a human in need thereof, can range from about 10 mg to about 50 mg or from about 15 mg to about 45 mg. In certain embodiments, the amount of progesterone administered to a subject in need thereof using the pharmaceutical composition of this disclosure can be about 15 mg, about 16 mg, about 17 mg, about 18 mg, about 19 mg, about 20 mg, about 25 mg, about 30 mg, about 31 mg, about 32 mg, about 33 mg, about 34 mg, about 35 mg, about 36 mg, about 37, about 38 mg, about 39 mg, or about 40 mg progesterone. In particular embodiments, a human in need thereof can receive either about 20 mg progesterone per dose or about 36 mg progesterone per dose when the pharmaceutical composition is administered.

To receive the desired amount of progesterone per dose, the human in need thereof can, in certain embodiments, be administered from about 300 mg to about 2000 mg of the pharmaceutical composition, from about 350 mg to about 1700 mg of the pharmaceutical composition, from about 400 mg to about 1400 mg of the pharmaceutical composition, from about 450 mg to about 1100 mg of the pharmaceutical composition, from about 500 mg to about 800 mg of the pharmaceutical composition, from about 550 mg to about 750 mg of the pharmaceutical composition, from about 575 mg to about 625 mg of the pharmaceutical composition, or about 600 mg of the pharmaceutical formulation. In other embodiments, the human in need thereof can be administered about 300 to about 350 mg of the pharmaceutical composition. In other embodiments, the human in need thereof can be administered about 350 to about 400 mg of the pharmaceutical composition. In other embodiments, the human in need thereof can be administered about 400 to about 450 mg of the pharmaceutical composition. In other embodiments, the human in need thereof can be administered about 450 to about 500 mg of the pharmaceutical composition. In other embodiments, the human in need thereof can be administered about 500 to about 550 mg of the pharmaceutical composition. In other embodiments, the human in need thereof can be administered about 550 to about 600 mg of the pharmaceutical composition. In other embodiments, the human in need thereof can be administered about 600 to about 650 mg of the pharmaceutical composition.

In embodiments wherein the amount of progesterone in the composition is about 6 weight percent of the composition and wherein the amount of progesterone to be administered to the human in need thereof is about 20 mg, the amount of the pharmaceutical formulation that can be administered to the human can be about 333 mg.

In embodiments wherein the amount of progesterone in the composition is about 6 weight percent of the composition and wherein the amount of progesterone to be administered to the human in need thereof is about 36 mg, the amount of the pharmaceutical formulation that can be administered to the human can be about 600 mg.

These dosages reflect the surprisingly enhanced bioavailability of progesterone provided by the present pharmaceutical compositions. These compositions provide the opportunity to reduce the amount of progesterone administered to a human in need thereof relative to currently marketed products such as PROMETRIUM. As discussed elsewhere herein, the PK parameters observed when the present pharmaceutical compositions are dosed are highly surprising in view of the known PK parameters associated with PROMETRIUM.

In certain embodiments, the pharmaceutical compositions can be administered to a human in need thereof in the amounts described above for the treatment of a disease or conditions treatable with progesterone. Such diseases and conditions include, but are not limited to, endometrial hyperplasia; secondary amenorrhea; prevention of preterm birth; and osteoporosis.

In certain embodiments, a human can be administered from about 300 mg to about 650 mg of a pharmaceutical compositions described herein to treat endometrial hyperplasia.

In other embodiments, a human can be administered from about 300 mg to about 1000 mg of a pharmaceutical compositions described herein to treat secondary amenorrhea.

In other embodiments, a human can be administered from about 300 mg to about 650 mg of a pharmaceutical compositions described herein to treat preterm birth.

In other embodiments, a human can be administered from about 300 mg to about 650 mg of a pharmaceutical compositions described herein to treat osteoporosis.

In each of the above described embodiments, a human can be administered about a dose of about 333 mg or about 600 mg of the pharmaceutical composition, such that the human receives about 20 mg or about 36 mg of progesterone per dose of the pharmaceutical composition.

In certain embodiments, the pharmaceutical composition can be administered once daily within in any of the above noted amounts until the disease or condition is treated.

In further embodiments, about 333 mg of the pharmaceutical composition can be administered once daily to treat the disease or condition.

In still another embodiments, about 600 mg of the pharmaceutical composition can be administered once daily to treat the disease or condition.

In certain embodiments, the amount of pharmaceutical composition administered to a given human subject can be an amount that renders the pharmaceutical composition bioequivalent to PROMETRIUM.

In certain embodiments, the amount of the pharmaceutical composition that is bioequivalent to PROMETRIUM can be from about 300 to about 350 mg of the pharmaceutical composition. In certain embodiments, the pharmaceutical composition can comprise about 6 weight percent progesterone. And in still further embodiments, the amount of progesterone administered to the human subject using the present pharmaceutical compositions to achieve bioequivalence to PROMETRIUM can be about 20 mg progesterone.

In certain embodiments, the steroid hormone is estradiol. In some embodiments, the pharmaceutical composition can be administered such that a subject in need thereof receives an amount of estradiol in the range of about 0.01 mg to about 2 mg, and in certain embodiments, about 2 mg, about 1 mg, about 0.75 mg, about 0.5 mg, about 0.25 mg, about 0.1 mg, about 0.075 mg, about 0.050 mg, about 0.025 mg, about 0.01 mg, or any range encompassing any of the noted values.

In certain embodiments, the steroid hormone is a combination of progesterone and estradiol, with dosages as described in the preceding paragraphs.

Although the pharmacokinetic profiles of many progesterone formulations can be affected by whether or not the formulation is taken with food, it has been surprisingly discovered that, in some embodiments, the present pharmaceutical compositions can deliver progesterone consistently both in the presence and absence of food. That is, and surprisingly, in some embodiments, the present pharmaceutical compositions do not show a food effect. This is an extremely beneficial property of certain embodiments of the disclosed pharmaceutical compositions as it allows for less restrictive dosing and increases the likelihood of patient compliance with a given dosing regimen. Lack of a food effect may further reduce both inter- and intra-patient variability when the pharmaceutical compositions of the present disclosure are dosed.

Pharmacokinetics and Metabolites

The disclosed pharmaceutical compositions can provide enhanced pharmacokinetics versus the currently marketed drug PROMETRIUM. For example, in certain embodiments, the pharmaceutical composition can have an $AUC_{0-t}$ that is at least about 1.1, at least about 1.2, at least about 1.3, at least about 1.4, at least about 1.5, at least about 1.6, at least about 1.7, at least about 1.8, at least about 1.9, or at least about 2 times greater than PROMETRIUM when the pharmaceutical compositions are dosed in the fasting state. That is, the pharmaceutical compositions can have AUCs that are at least about 110 percent, at least about 120 percent, at least about 130 percent, at least about 140 percent, at least about 150 percent, at least about 160 percent, at least about 170 percent, at least about 180 percent, at least about 190 percent, or at least about 200 percent the AUC of PROMETRIUM when the pharmaceutical compositions are dosed in the fasting state.

Similarly, in certain embodiments, the pharmaceutical composition can have a $C_{max}$ that is at least about 1.1, at least about 1.2, at least about 1.3, at least about 1.4, at least about 1.5, at least about 1.6, at least about 1.7, at least about 1.8, at least about 1.9, at least about 2, at least about 2.2, at least about 2.4, at least about 2.6, at least about 2.8, or at least about 3 times greater than PROMETRIUM when the pharmaceutical compositions are dosed in the fasting state.

In certain embodiments, the pharmaceutical composition can have a $t_{max}$ that is at least about 3, at least about 4, at least about 5, at least about 6, at least about 7, at least about 8, at least about 9, at least about 10, at least about 11, at least about 12, at least about 13, at least about 14, at least about 15, at least about 16, or at least about 17 times shorter than PROMETRIUM when the pharmaceutical compositions are dosed in the fasting state. That is, and in certain embodiments, the pharmaceutical compositions disclosed herein reach their $C_{max}$ considerably earlier than PROMETRIUM.

Methods for Preparing the Pharmaceutical Compositions

In certain embodiments, the compositions described herein can be prepared according to the following general procedure. In certain embodiments, and in a first step, the steroid hormone, and in particular embodiments, progesterone, can be solubilized in the medium chain oil by mixing the steroid hormone with the medium chain oil under mild heating, i.e. from about 35° C. to about 60° C., and in certain embodiments at about 40 ° C. The mixture can be mixed for an amount of time sufficient to solubilize and uniformly distribute the steroid hormone in the medium chain oil. Typically, the solubilization can be performed in an appropriate vessel, such as optionally temperature-controlled jacketed stainless steel vessel of the type typically found in medium and large scale formulation manufacturing facilities.

The medium chain oil can have properties described elsewhere herein and can be added in the amounts specified elsewhere herein. In particular embodiments, the medium chain oil can comprise a mixture of a medium chain monoglyceride and a medium chain diglyceride. In other embodiments, however, the medium chain oil can comprise a medium chain monoglyceride or a medium chain diglyceride.

As discussed elsewhere herein, the medium chain monoglyceride can be, predominantly, a single medium chain monoglyceride, such as glyceryl monocaproate, glyceryl monocaprylate, glyceryl monocaprate, glyceryl monolaurate, or glyceryl monomyristate. These monoglycerides are well known to those of ordinary skill in the art and are available in various commercial embodiments, including from ABITEC Corp, a division of Associated British Food, PLC, as CAPMUL 708G, CAPMUL 808G, CAPMUL MCM C8, and CAPMUL MCM C10. In particular embodiments, the medium chain monoglyceride can be, predominantly, a single medium chain monoglyceride such as glyceryl monocaproate, glyceryl monocaprylate, or glyceryl monocaprate. In specific embodiments, the medium chain monoglyceride can be, predominantly, glyceryl monocaprylate, commercially available as CAPMUL 708G.

Similarly, and also discussed previously, the one or more medium chain diglycerides can be simple diglycerides, such as glyceryl dicaproate, glyceryl dicaprylate, glyceryl dicaprate, glyceryl dilaurate, or glyceryl dimyristate. Alternatively, the one or more medium chain diglycerides can be mixed or complex diglycerides such as glyceryl caproate/caprylate, glyceryl caproate/caprate, glyceryl caproate/laurate, glyceryl caproate/myristate, glyceryl caprylate/caprate, glyceryl caprylate/laurate, glyceryl caprylate/myristate, glyceryl caprate/laurate, glyceryl caprate/myristate, or glyceryl laurate/myristate. In specific embodiments, the one or more medium chain diglycerides can be glyceryl caprylate/caprate. Exemplary commercially available medium chain diglycerides include, but are not limited to, CAPMUL 471, CAPMUL MCM, CAPMUL MCM NF, CAPMUL MCM EP, and IMWITOR 742. The CAPMULs are commercially available from ABITEC Corp.

In certain embodiments, the one or more medium chain diglycerides can be glyceryl caprylate/caprate. A commercially available version of this component suitable for use in the pharmaceutical composition is CAPMUL MCM NF.

Once the steroid hormone has sufficiently dissolved in the medium chain oil, additional components which can be included in a given composition as specified elsewhere herein, can be added. For example, in certain embodiments, a polysorbate can be added to the medium chain oil/steroid hormone mixture in the amounts specified elsewhere herein. In certain embodiments, the polysorbate can be selected from the group consisting of polysorbate 20, polysorbate 40, polysorbate 60, polysorbate 65, and polysorbate 80. In certain embodiments, the polysorbate can be polysorbate 80.

In certain embodiments, and in addition to the polysorbate, a d-α-tocopherol polyethylene glycol succinate (TPGS) derivative and an antioxidant can be added to the medium chain oil/steroid hormone mixture. Each of the d-α-tocopherol polyethylene glycol succinate (TPGS) derivative and an antioxidant can be added in the amounts and specific embodiments discussed elsewhere herein.

In other embodiments, in addition to the polysorbate, a PEG X hydrogenated castor oil and an antioxidant can also be added to the medium chain oil/steroid hormone mixture. Each of the PEG X hydrogenated castor oil and an antioxidant can be added in the amounts and specific embodiments discussed elsewhere herein.

In each of the above noted embodiments, addition of the antioxidant can be omitted.

Typically, and when added to a given composition, the various additional components are added with mixing and under mild heating to ensure homogenous distribution of the various components in the composition. When present, each of the antioxidant, the polysorbate, the d-α-tocopherol polyethylene glycol succinate (TPGS) derivative, and the PEG X hydrogenated castor oil, can be added in the amounts and embodiments disclosed elsewhere herein.

Once the addition of all of the necessary or desired components is complete, the composition can be stirred until it reaches room temperature. Once at room temperature, and when desired, a terpene, such as d-limonene, can be added to the composition in any of the amounts specified elsewhere herein.

The resulting composition, after an optional deaeration process, can then be used as the fill material in the encapsulation process disclosed elsewhere herein.

In another embodiment, the compositions described herein may be prepared by mixing the desired components, exclusive of the optional terpene, at room temperature and subsequently warming the resulting mixture to from about 35° C. to about 60° C., and in certain embodiments to about 40° C. to affect dissolution of the steroid hormone. Following a sufficient amount of stirring to ensure the desired level of dissolution and homogenous distribution of the various components in the composition, the mixture can be cooled to room temperature. After cooling, and as in the alternative embodiment discussed above, a terpene, such as d-limonene, can be added to the composition in any of the amounts specified elsewhere herein.

The resulting composition, after an optional deaeration process, can then be used as the fill material in the encapsulation process discussed below.

Encapsulation

Although the pharmaceutical composition can be dosed as a liquid, in certain embodiments, the pharmaceutical composition can be encapsulated in a gelatin capsule, or other similar encapsulated dosage form known to those of skill in the art. The gelatin capsule can be a soft gelatin capsule or a hard gelatin capsule. The hard gelatin capsule can be a two-piece, standard gelatin capsule which typically includes a first capsule portion (i.e., half or bottom) and a second capsule portion (i.e., the other half or top). The soft gelatin capsule can be a two-piece capsule wherein two portions are sealed together or a one-piece, hermetically sealed capsule.

In certain embodiments, the soft gelatin capsule can be a one-piece, hermetically sealed gelatin based capsule which can be made by techniques known to those skilled in the art. In certain embodiments, the gelatin used to form the soft gelatin capsule can include water, gelatin, and a plasticizer to control the softness and flexibility of the capsule. Other additives for use in the gelatin suitable for preparing the soft gelatin capsule, include but are not limited to, flavorants, colorants, and opacifiers.

Soft gelatin capsules can be produced in a known manner, including with a rotary die process in which a molten mass of a gelatin containing the appropriate or necessary additives, is fed from a reservoir onto drums to form two spaced sheets or ribbons of gelatin in a semi-molten state. These ribbons are fed around rollers and brought together at convergent angle into the nip of a pair of roller dies that include opposed die cavities. A liquid fill formulation, such as the pharmaceutical composition of this disclosure, can then be fed into the wedge-shaped joinder of the ribbons. The gelatin ribbons are continuously conveyed between the dies, with portions of the fill formulation being trapped between the sheets inside the die cavities. The sheets are then pressed together, and severed around each die so that opposed edges of the sheet flow together to form a continuous gelatin sheath around the entrapped liquid pharmaceutical composition. The part of the gelatin sheet that is severed from the segments forming the capsules can then be collected for recycling or can be discarded. The resulting soft capsules can then be dried and packaged.

Various gelatin compositions known in the prior art can be used to encapsulate the pharmaceutical composition of this disclosure. For example, suitable gelatin capsules can be prepared from a gelatin mixture comprising from about 30% w/w to about 85% w/w gelatin and in certain embodiments, about 30% w/w to about 50% w/w; about 15% w/w to about 40% w/w of one or more plasticizer; and from 25% w/w to about 50% w/w of water. In certain embodiments, the gelatin will have a bloom in the rage of about 150 to about 275, and can be Type A or B gelatins or a mixture thereof.

Examples of suitable Type A gelatin include without limitation acid bone gelatin.

Examples of suitable Type B gelatin include without limitation lime bone gelatin.

Suitable gelatin plasticizers are well known to those of ordinary skill in the art and include, but are not limited to, polyhydric alcohols such as sorbitol, glycerin, mannitol, xylitol, maltitol, and sorbitan; dialkylphthalates; lower alkyl citrates wherein the lower alkyl has 1-6 carbon atoms; glycols and polyglycols including polyethylene glycols with a molecular weight range of about 200 to about 2,000, methoxyl-propylene-glycol, and 1,2-propylene glycol; esters of polyhydroxy-alcohols such as mono-, di-, and tri-acetates of glycerol; ricinoleic acid and esters thereof; and mixtures of the above. The gelatin pharmaceutical composition can also contain other ingredients including, but not limited to, taste modifiers, coloring agents, opacifiers, and moisture retaining agents.

Additional Non-Limiting Embodiments

Additional non-limiting embodiments of the pharmaceutical compositions and methods disclosed herein are described below:

(A) A pharmaceutical composition for providing enhanced oral bioavailability of progesterone, the pharmaceutical composition comprising: progesterone, a polysorbate, and a medium chain oil, wherein the medium chain oil comprises at least about 50 weight percent of a predominantly medium chain monoglyceride; and the progesterone is fully solubilized.

(B) The pharmaceutical composition of embodiment (A), wherein the medium chain oil comprises at least about 60 weight percent of a predominantly medium chain monoglyceride.

(C) The pharmaceutical composition of embodiment (A), wherein the medium chain oil comprises at least about 70 weight percent of the predominantly medium chain monoglyceride.

(D) The pharmaceutical composition of embodiment (A), wherein the medium chain oil comprises at least about 80 weight percent of the predominantly medium chain monoglyceride.

(E) The pharmaceutical composition of embodiment (A), wherein the medium chain oil comprises at least about 90 weight percent of the predominantly medium chain monoglyceride.

(F) The pharmaceutical composition of embodiment (E), wherein the polysorbate is selected from the group consisting of polysorbate 20, polysorbate 40, polysorbate 60, polysorbate 65, and polysorbate 80.

(G) The pharmaceutical composition of embodiment (A), wherein the pharmaceutical composition provides an oral bioavailability of at least about 150 percent as measured by an increase in AUC when compared to a reference product.

(H) The pharmaceutical composition of embodiment (A), further comprising a polyoxyethylene hydrogenated castor oil.

(I) The pharmaceutical composition of embodiment (A), further comprising a D-α-Tocopherol polyethylene glycol succinate derivative.

(J) The pharmaceutical composition of embodiment (A), further comprising a terpene.

(K) The pharmaceutical composition of embodiment (A), wherein the predominantly medium chain monoglyceride and the progesterone can be present at a weight ratio of about 10:1 to about 15:1.

(L) The pharmaceutical composition of embodiment (K), wherein the predominantly medium chain monoglyceride comprises at least about 60 weight percent of the medium chain oil.

(M) The pharmaceutical composition of embodiment (K), wherein the predominantly medium chain monoglyceride comprises at least about 70 weight percent of the predominantly medium chain oil.

(N) The pharmaceutical composition of embodiment (K), wherein the predominantly medium chain monoglyceride comprises at least about 80 weight percent of the medium chain oil.

(O) The pharmaceutical composition of embodiment (A), wherein the predominantly medium chain monoglyceride comprises at least about 90 weight percent of the medium chain oil.

(P) The pharmaceutical composition of embodiment (O), wherein the polysorbate is selected from the group consisting of polysorbate 20, polysorbate 40, polysorbate 60, polysorbate 65, and polysorbate 80.

(Q) The pharmaceutical composition of embodiment (K), wherein the pharmaceutical composition provides an oral bioavailability of at least about 150 percent as measured by an increase in AUC when compared to a reference product.

(R) The pharmaceutical composition of embodiment (K), further comprising a polyoxyethylene hydrogenated castor oil.

(S) The pharmaceutical composition of embodiment (K), further comprising a D-α-Tocopherol polyethylene glycol succinate derivative.

(T) The pharmaceutical composition of embodiment (A), further comprising a terpene.

(U) An oral, fully-solubilized progesterone pharmaceutical composition comprising: progesterone and a polysorbate in a weight ratio of from about 1:2 to about 2:1; and a medium chain oil comprising a mixture of medium chain mono- and diglycerides, the medium chain oil not containing more than about 10 weight percent triglycerides.

(V) The pharmaceutical composition of embodiment (U), wherein the polysorbate is selected from the group consisting of polysorbate 20, polysorbate 40, polysorbate 60, polysorbate 65, and polysorbate 80.

(W) The pharmaceutical composition of embodiment (U), wherein the pharmaceutical composition provides an oral bioavailability of at least about 150 percent as measured by an increase in AUC when compared to a reference product.

(X) The pharmaceutical composition of embodiment (U), further comprising a polyoxyethylene hydrogenated castor oil.

(Y) The pharmaceutical composition of embodiment (U), further comprising a D-α-Tocopherol polyethylene glycol succinate derivative.

(Z) The pharmaceutical composition of embodiment (U), further comprising a terpene.

(AA) The pharmaceutical composition of any of embodiments (A) through (T), wherein the predominantly medium chain monoglyceride is glyceryl monocaproate, glyceryl monocaprylate, glyceryl monocaprate, glyceryl monolaurate, or glyceryl monomyristate.

(BB) The pharmaceutical composition of embodiment (AA), wherein the medium chain monoglyceride is glyceryl monocaprylate.

(CC) The pharmaceutical composition of embodiment (BB), wherein the glyceryl monocaprylate comprises at least about 85 weight percent of the medium chain oil.

(DD) The pharmaceutical composition of embodiment (H), wherein the polyoxyethylene hydrogenated castor oil is a polyoxyl X hydrogenated castor oil and X is an integer from 1 to 100.

(EE) The pharmaceutical composition of embodiment (DD), wherein the polyoxyethylene hydrogenated castor oil is polyoxyl 40 hydrogenated castor oil.

(FF) The pharmaceutical composition of embodiment (EE), wherein the polyoxyl 40 hydrogenated castor oil comprises from about 1 to about 10 weight percent of the pharmaceutical composition.

(GG) The pharmaceutical composition of embodiment (FF), wherein the polyoxyl 40 hydrogenated castor oil comprises about 4 weight percent to about 5 weight percent of the pharmaceutical composition.

(HH) The pharmaceutical composition of any of embodiments (A) through (U), wherein the medium chain oil further comprises a diglyceride.

(II) The pharmaceutical composition of embodiment (HH), wherein the diglyceride is a mixed or complex diglyceride selected from the group consisting of glyceryl caproate/caprylate, glyceryl caproate/caprate, glyceryl caproate/laurate, glyceryl caproate/myristate, glyceryl caprylate/caprate, glyceryl caprylate/laurate, glyceryl caprylate/myristate, glyceryl caprate/laurate, glyceryl caprate/myristate, and glyceryl laurate/myristate.

(JJ) The pharmaceutical composition of embodiment (JJ), wherein the diglyceride is glyceryl caprylate/caprate.

(KK) The pharmaceutical composition of any of embodiments (HH) through (JJ), wherein the diglyceride comprises from about 5 weight percent to about 10 weight percent of the pharmaceutical composition.

(LL) The pharmaceutical composition of embodiment (KK), wherein the diglyceride comprises from about 8 to about 9 weight percent of the pharmaceutical composition.

(MM) The pharmaceutical composition of embodiments (I), wherein the d-α-tocopherol polyethylene glycol succinate derivative has the structure

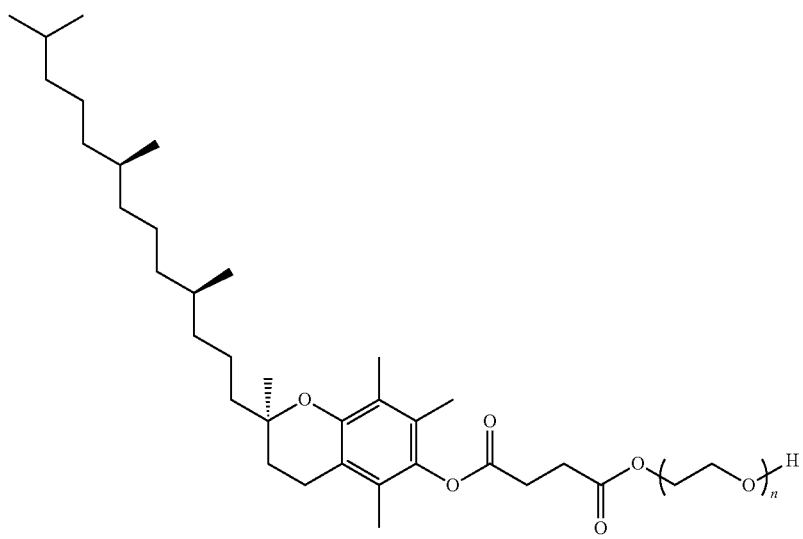

and n is 1-100.

(NN) The pharmaceutical composition of embodiment (MM), wherein n is 1 to 50.

(OO) The pharmaceutical composition of embodiment (NN), wherein n is 1 to 25.

(PP) The pharmaceutical composition of embodiment (OO), wherein n is about 22.

(QQ) The pharmaceutical composition of embodiment (MM), wherein the d-α-tocopherol polyethylene glycol succinate derivative is TPGS-1000.

(RR) The pharmaceutical compositions of any of embodiments (MM) through (QQ), wherein the d-α-tocopherol polyethylene glycol succinate derivative comprises from about 0.1 weight percent to about 5 weight percent of the pharmaceutical composition.

(SS) The pharmaceutical composition of embodiment (RR), wherein the d-α-tocopherol polyethylene glycol succinate derivative comprises from about 2 weight percent to about 3 weight percent of the pharmaceutical composition.

(TT) The pharmaceutical composition of embodiment (SS), wherein the d-α-tocopherol polyethylene glycol succinate derivative comprises about 2.3 weight percent or about 2.4 weight percent of the pharmaceutical composition.

(UU) The pharmaceutical composition of any of the foregoing embodiments, wherein the pharmaceutical composition provides an oral bioavailability of at least about 150 percent as measured by an increase in AUC when compared to a reference product.

(VV) The pharmaceutical composition of embodiment (UU), wherein the reference product is PROMETRIUM.

(WW) The pharmaceutical composition of any preceding embodiment, further comprising a terpene.

(XX) The pharmaceutical composition of embodiment (WW), wherein the terpene is d-limonene.

(YY) A method of treating a disease or condition associated with reduced progesterone levels, the method comprising administering to a subject in need thereof a pharmaceutical composition according to any of the preceding embodiments.

(ZZ) A method of treating a disease or condition associated with reduced progesterone levels, the method comprising administering to a subject in need thereof a pharmaceutical composition of any of the preceding embodiments.

(AAA) The method of embodiment (ZZ), wherein the disease or condition associated with reduced progesterone levels is selected from the group consisting of endometrial hyperplasia; secondary amenorrhea; prevention of preterm birth; and osteoporosis.
(BBB) The method of embodiment (AAA), wherein the disease or condition associated with reduced progesterone levels is menopause.
(CCC) A method of treating a disease or condition associated with reduced progesterone levels, the method comprising administering to a subject in need thereof a pharmaceutical composition comprising one or more predominantly medium chain oils and progesterone, wherein the pharmaceutical composition has an AUC that is at least 150% of the AUC of an equal amount of a reference product.
(DDD) The method of embodiment (CCC), wherein the pharmaceutical composition has a $C_{max}$ that is at least 150% of the $C_{max}$ of an equal amount of a reference product
(EEE) The pharmaceutical composition of any of the preceding embodiments, wherein progesterone is the sole active agent.

EXAMPLES

The pharmaceutical composition described herein is now further detailed with reference to the following examples. These examples are provided for the purpose of illustration only and the embodiments described herein should in no way be construed as being limited to these examples. Rather, the embodiments should be construed to encompass any and all variations which become evident as a result of the teaching provided herein.

Example 1

Pharmaceutical Compositions

Pharmaceutical compositions having the ingredients shown in Table 1 were prepared by combining the ingredients using standard preparatory techniques.

TABLE 1

Solubilized Progesterone Fill Formulas (all values presented in mg/g)

| Component | Pharma. Composition | | | | | | |
|---|---|---|---|---|---|---|---|
| | A | B | C | D | E | F | G |
| CAPMUL 708G | 761.06 | 723.01 | 723.01 | 761.06 | 834.62 | — | 751.16 |
| CAPMUL MCM, NF | 84.56 | 80.33 | 80.33 | 84.56 | — | 834.62 | 83.46 |
| Ultra High Purity d-limonene | — | 42.28 | 42.28 | — | — | — | — |
| BHT | 0.28 | 0.28 | 0.28 | 0.28 | — | — | — |
| Progesterone | 60.13 | 60.13 | 60.13 | 60.13 | 72.64 | 72.64 | 72.64 |
| Polysorbate 80 | 70.47 | 70.47 | 46.98 | 46.98 | 69.55 | 69.55 | 69.55 |
| TPGS 1000 | 23.49 | 23.49 | — | — | 23.18 | 23.18 | 23.18 |
| KOLLIPHOR RH 40 | — | — | 46.98 | 46.98 | — | — | — |

Example 2

Particle Size Analysis

Average particle sizes for each of Pharmaceutical Compositions A, B, C, and D as disclosed in Example 1 were measured using a DELSA Nano photon correlation spectrometer. Approximately 0.5 g of a given sample was diluted with 55 ml of filtered deionized water and the mean size of the resulting particle and the zeta potential was calculated.

TABLE 2

| Pharmaceutical composition | Mean size (nm) ± Std. Dev. | Zeta Potential (mV) |
|---|---|---|
| A | 301.6 ± 164.4 | −16.89 |
| B | 678.2 ± 698.6 | −16.87 |
| C | 575.2 ± 604.8 | −20.63 |
| D | 156.3 ± 52.2 | −18.37 |

Example 3

Oral Bioavailability in Rats

Oral bioavailability of the pharmaceutical compositions were assessed in male Sprague-Dawley rats. According to the protocol, 30 male rats were divided into 6 groups of 5 rats each. The rats were then treated with one of the pharmaceutical compositions discussed in Example 1 (Compositions A, B, C, and D), Pharmaceutical Composition H (a non-micelle forming, fully-solubilized progesterone pharmaceutical composition within the scope of this disclosure described more fully in Table 3), or PROMETRIUM according to the schedule shown in Table 4.

TABLE 3

Pharmaceutical Composition H

| Component | Chemical Name | Quantity (mg/g) |
|---|---|---|
| CAPMUL 708 G | Glyceryl Caprylate | 846 |
| CAPMUL MCM, NF | Caprylic/capric mono/diglycerides | 94 |
| Progesterone | API | 60 |

TABLE 4

| Study Day | Event |
|---|---|
| −4 | Animals were transferred to surgery facility and were group/gang housed. |
| −3 | Animals were observed. |

TABLE 4-continued

| Study Day | Event |
|---|---|
| −2 | Animals were observed. |
| −1 | Animals were fitted with jugular vein catheters (vaporized isoflurane anesthesia) and treated with analgesics. The animals were fasted for 12 hours starting at 8:00 PM. |
| 0 | Gavage capsules were filled with 20 μL of compound per capsule. Baseline plasma samples were collected, the animals received compound via capsule gavage, and additional plasma samples were taken at 10, 20, 40, 60, 90, 120, 180, and 240 minutes post dosing. Frozen plasma samples were shipped on dry ice for analysis. |

Although PROMETRIUM was dosed in a capsule filled with 20 μL of the PROMETRIUM formulation, the PROMETRIUM capsule contained at least 6 times as much progesterone (400 mg/g formulation) as the test pharmaceutical compositions (60 mg/g composition) due to the way in which PROMETRIUM is formulated.

Figure 11:
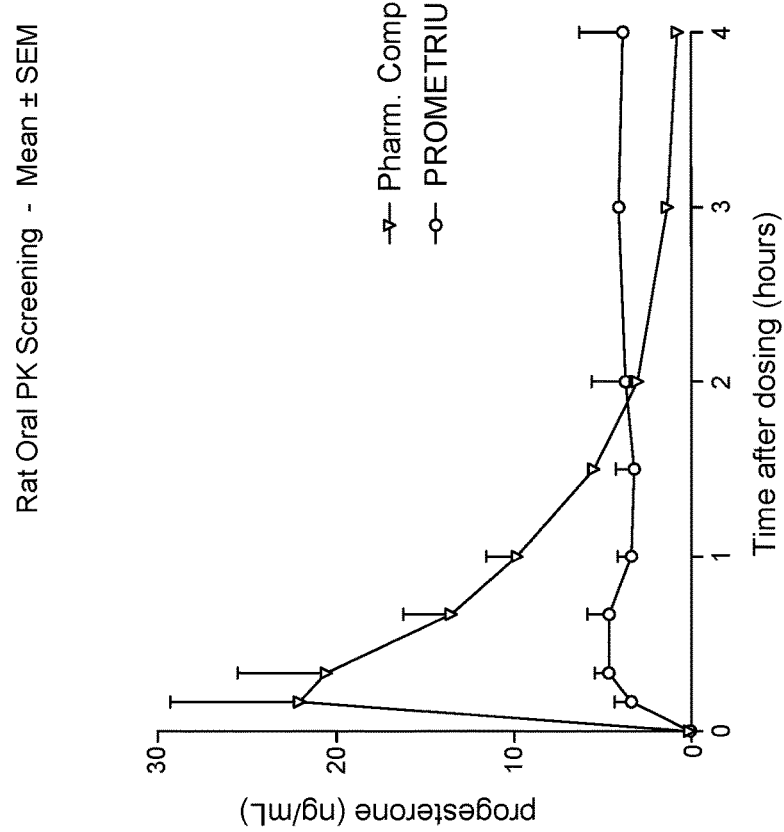
FIG. 11 is graph of plasma concentration of progesterone vs. time for PROMETRIUM and test pharmaceutical composition D.

The frozen plasma samples were then analyzed and the data plotted. The results are shown in FIGS. 1 (linear-linear) and 2 (log-linear). Both figures show that test Pharmaceutical Compositions A, C, and D performed better than Pharmaceutical Composition H and PROMETRIUM. FIG. 11 shows the performance of Pharmaceutical Composition D and PROMETRIUM, as both shown in FIG. 1, in the absence of the other tested formulations.

The means of the PK parameters observed (+/− standard deviation) are shown in Table 5.

TABLE 5

| Non-Normalized Progesterone PK Data | | | | | | |
|---|---|---|---|---|---|---|
| | A | B | C | D | H | PROMETRIUM |
| Dose (mg/kg) | 3.7 | 3.7 | 3.7 | 3.7 | 3.7 | 25 |
| $C_{max}$ (ng/mL) | 20.8 ± 12.8 | 13 ± 9 | 24.7 ± 11.2 | 23.5 ± 15.3 | 13.1 ± 6.9 | 6.9 ± 4.0 |
| $t_{max}$ (hr) | 0.467 ± 0.183 | 0.167 ± 0.167 | 0.4 ± 0.346 | 0.333 ± 0.204 | 0.367 ± 0.183 | 2.2 ± 1.609 |
| $AUC_{0-t}$ (ng · hr/mL) | 27.3 ± 23.0 | 12.5 ± 9.2 | 26.2 ± 11.9 | 24.2 ± 8.8 | 14.1 ± 7.6 | 15.1 ± 8.4 |
| $AUC_{0-\infty}$ (ng · hr/mL) | 28.0 ± 23.4 | 14.1 ± 11.1 | 27.1 ± 11.7 | 25.5 ± 8.2 | 15.6 ± 8.5 | 18.9 ± 13.6 |

Despite containing significantly less progesterone than PROMETRIUM, each of the test pharmaceutical compositions provided a higher $C_{max}$ (greater than 10-fold) and $AUC_{0-t}$ (4.5 to 10-fold—except for Pharmaceutical Composition H, which showed an AUC similar to PROMETRIUM), when normalized to a standard 1 mg dose than was observed for PROMETRIUM. Each of the test pharmaceutical compositions had a higher $C_{max}$ and shorter $t_{max}$ than PROMETRIUM, suggesting more rapid absorption.

Figure 3:
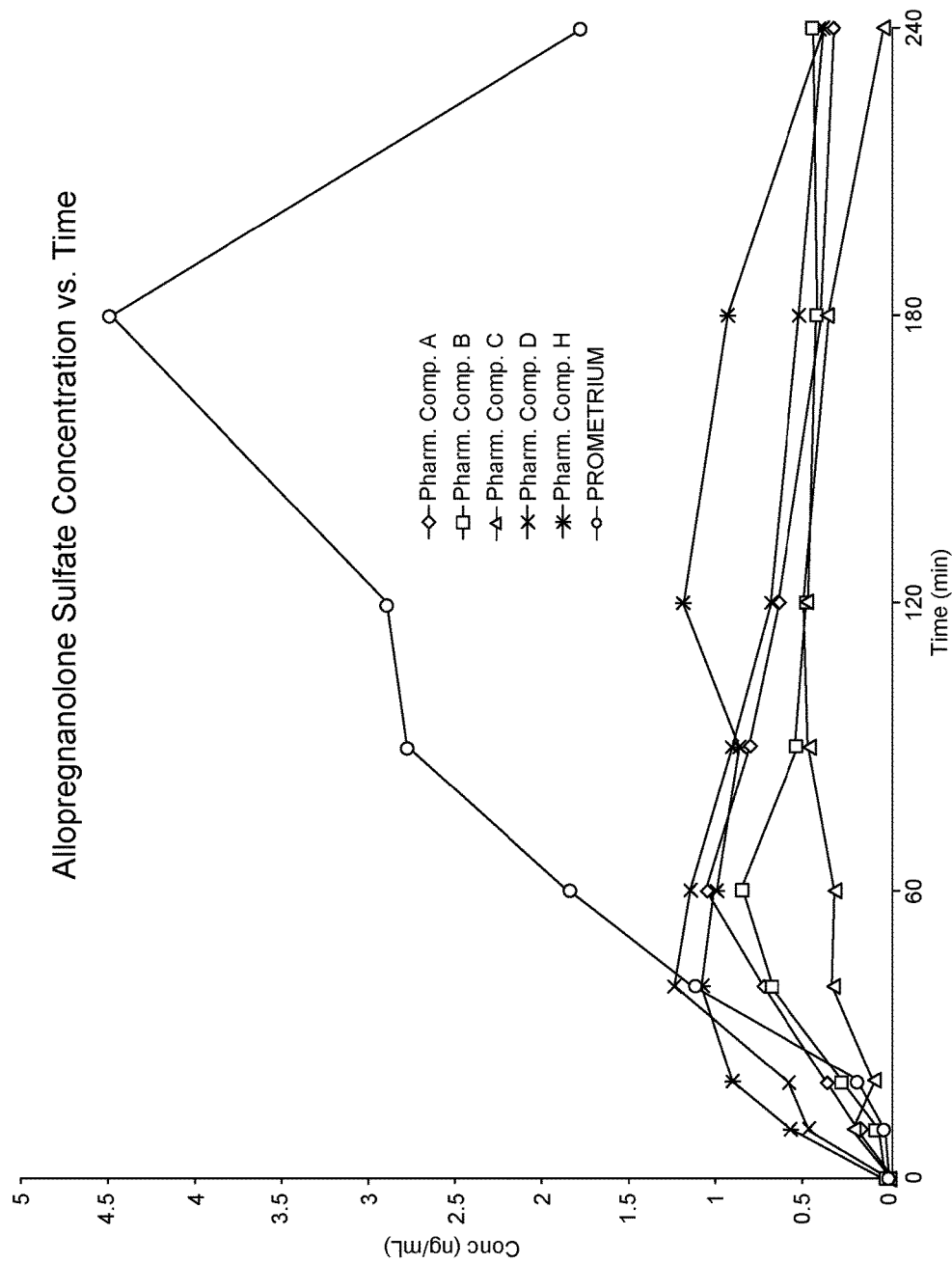
Figure 4:
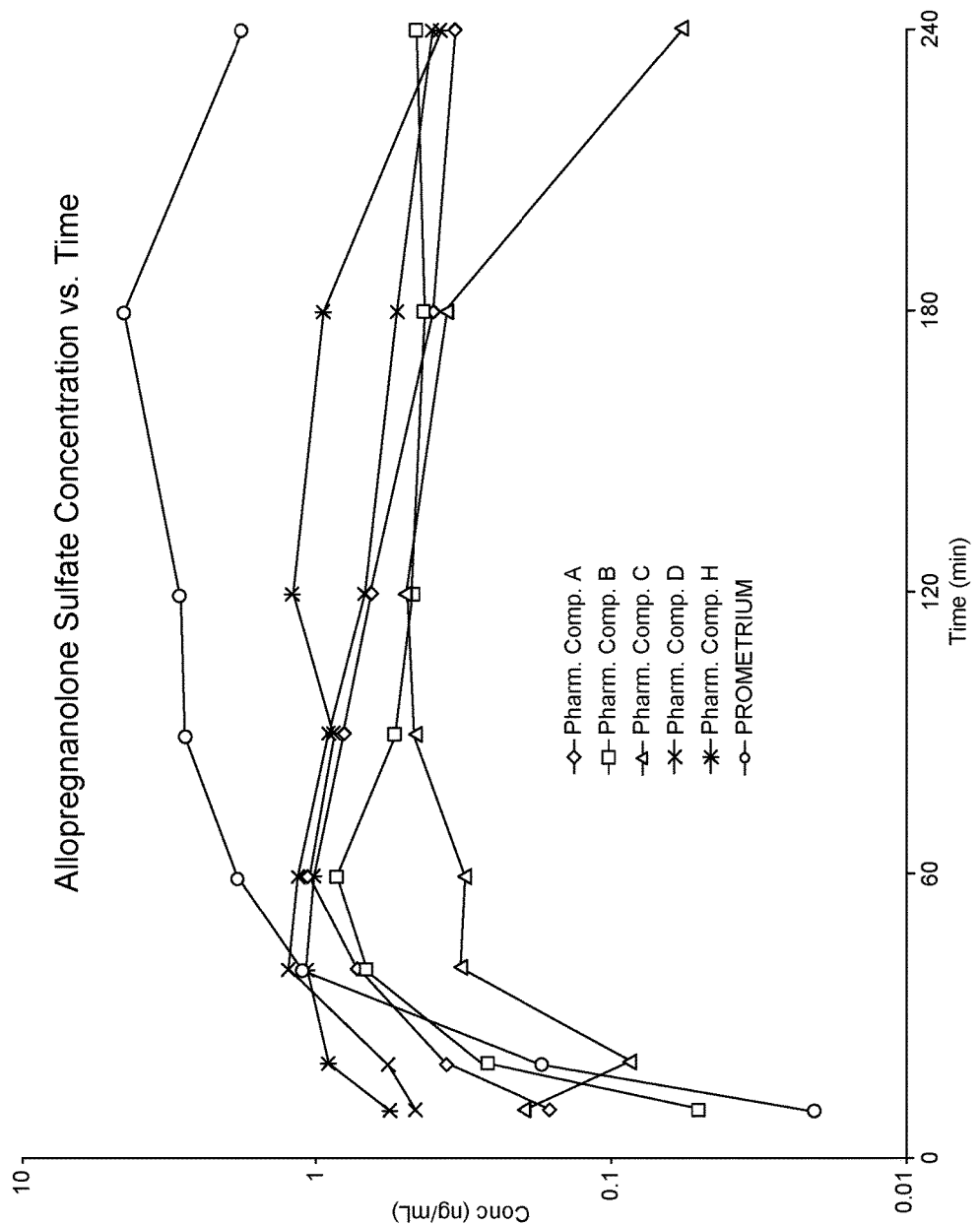
Figure 5:
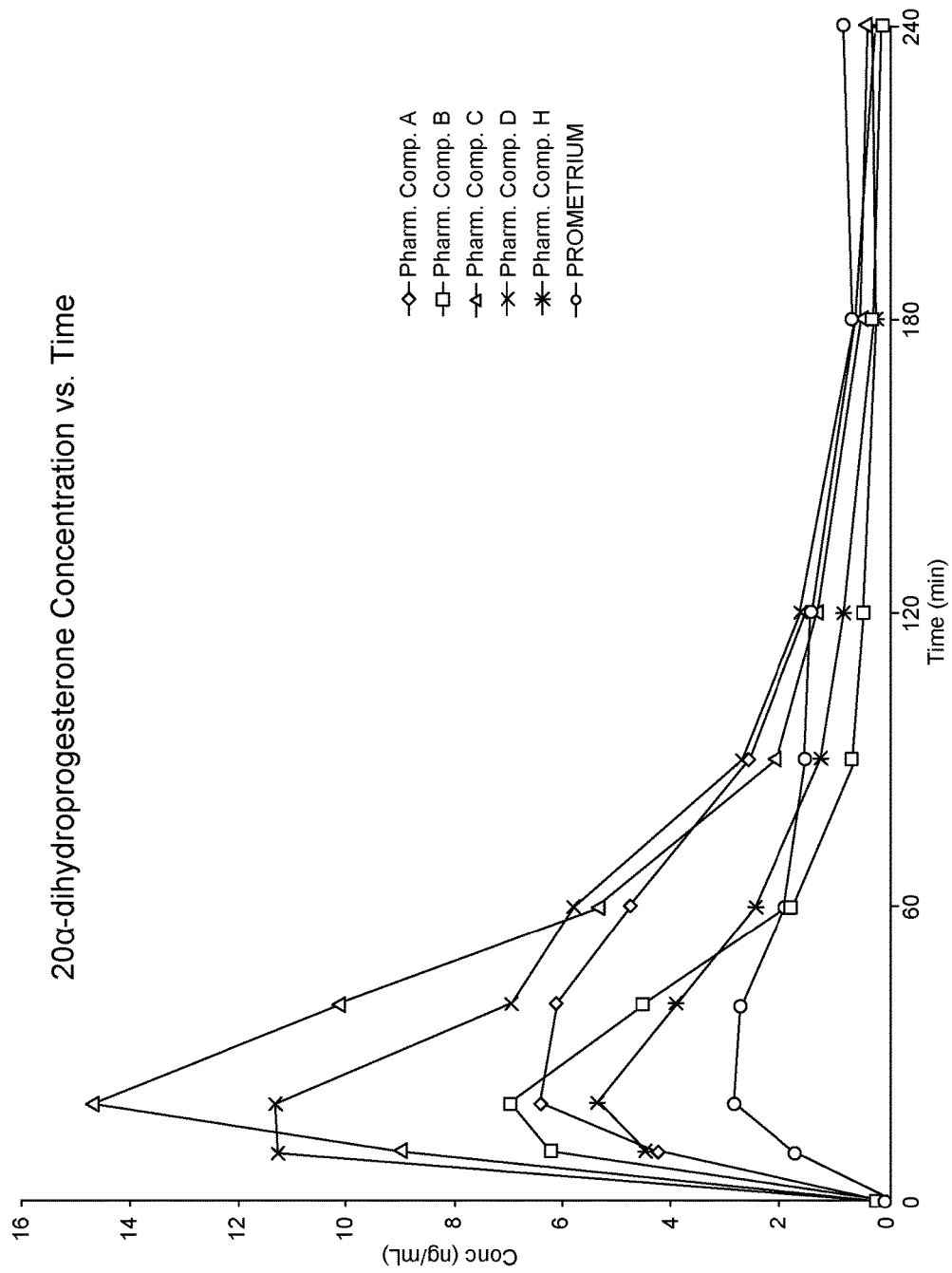
Figure 6:
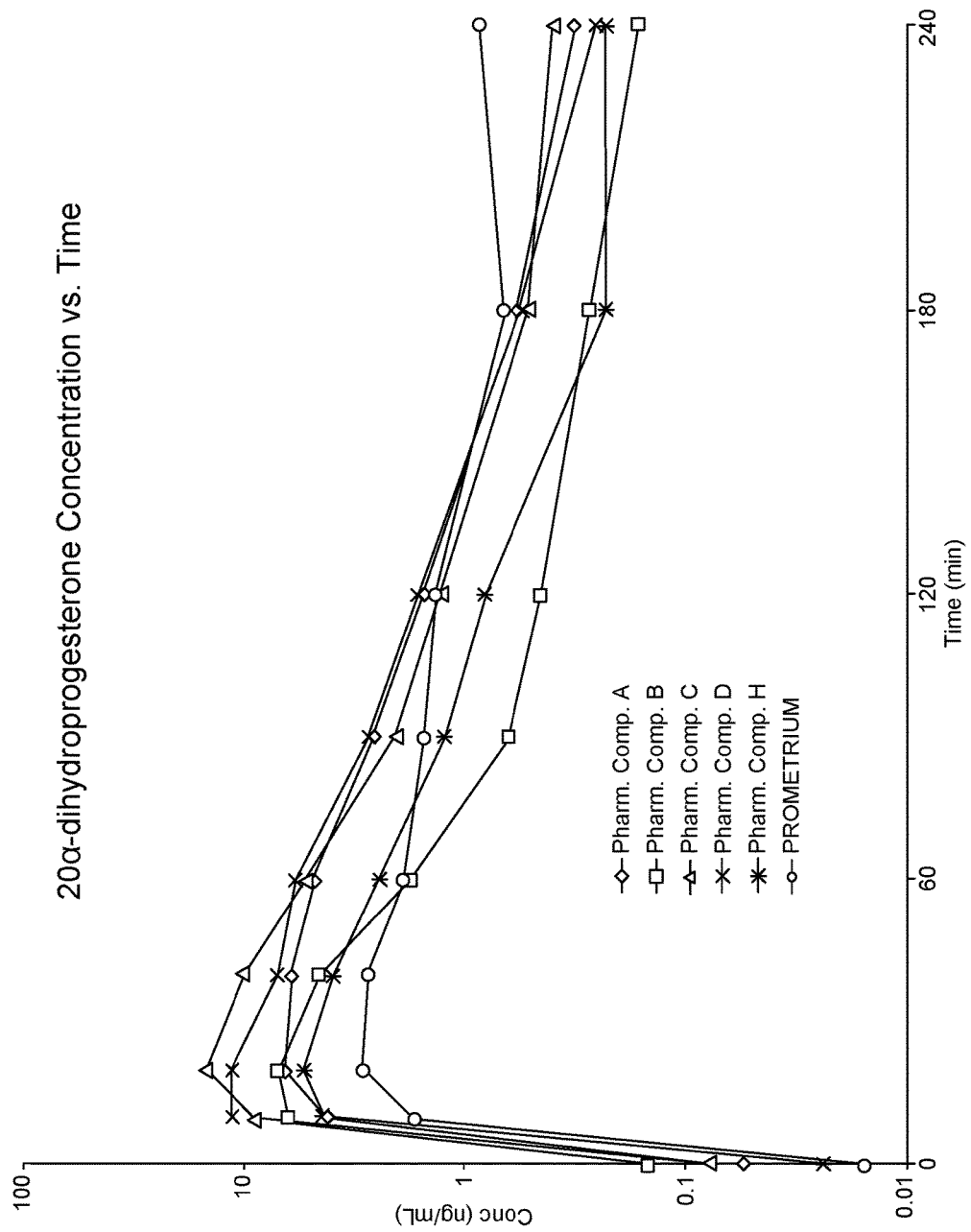
FIG. 6 is a log-linear version of FIG. 5.
Figure 7:
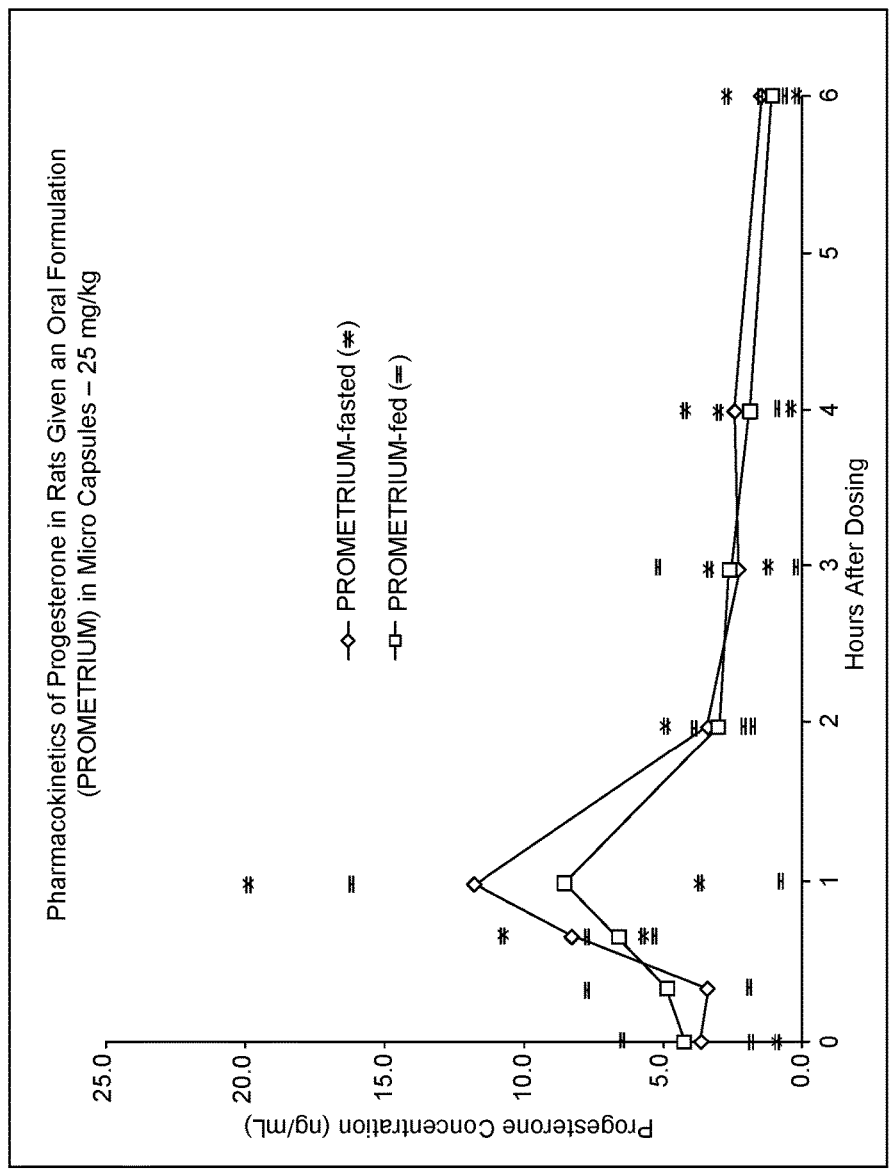
FIG. 7 is a graph of the plasma concentration of progesterone vs. time for fed and fasted rats dosed with 20 µl (25 mg/kg sample) of PROMETRIUM.
Figure 8:
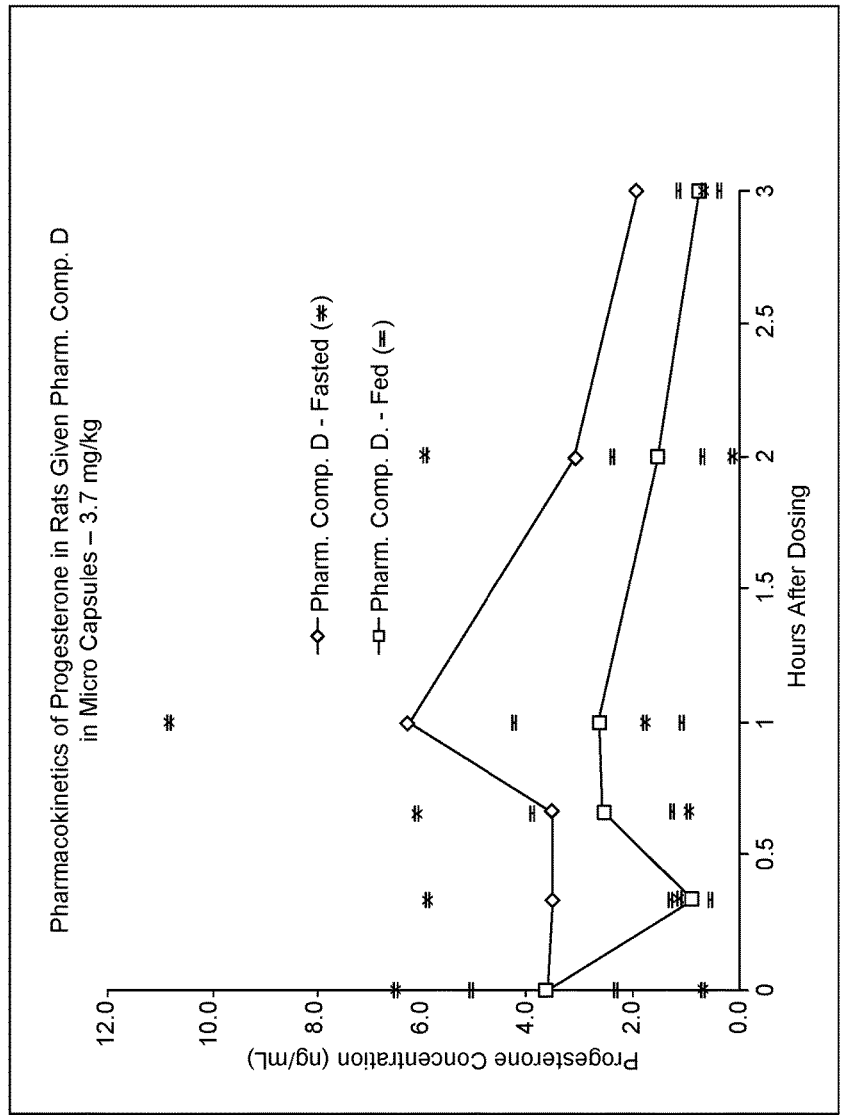
FIG. 8 is a graph of the plasma concentration of progesterone vs. time for fed and fasted rats dosed with 20 µl (3.7 mg/kg progesterone) of test pharmaceutical composition D in a gavage micro capsule.
Figure 9:
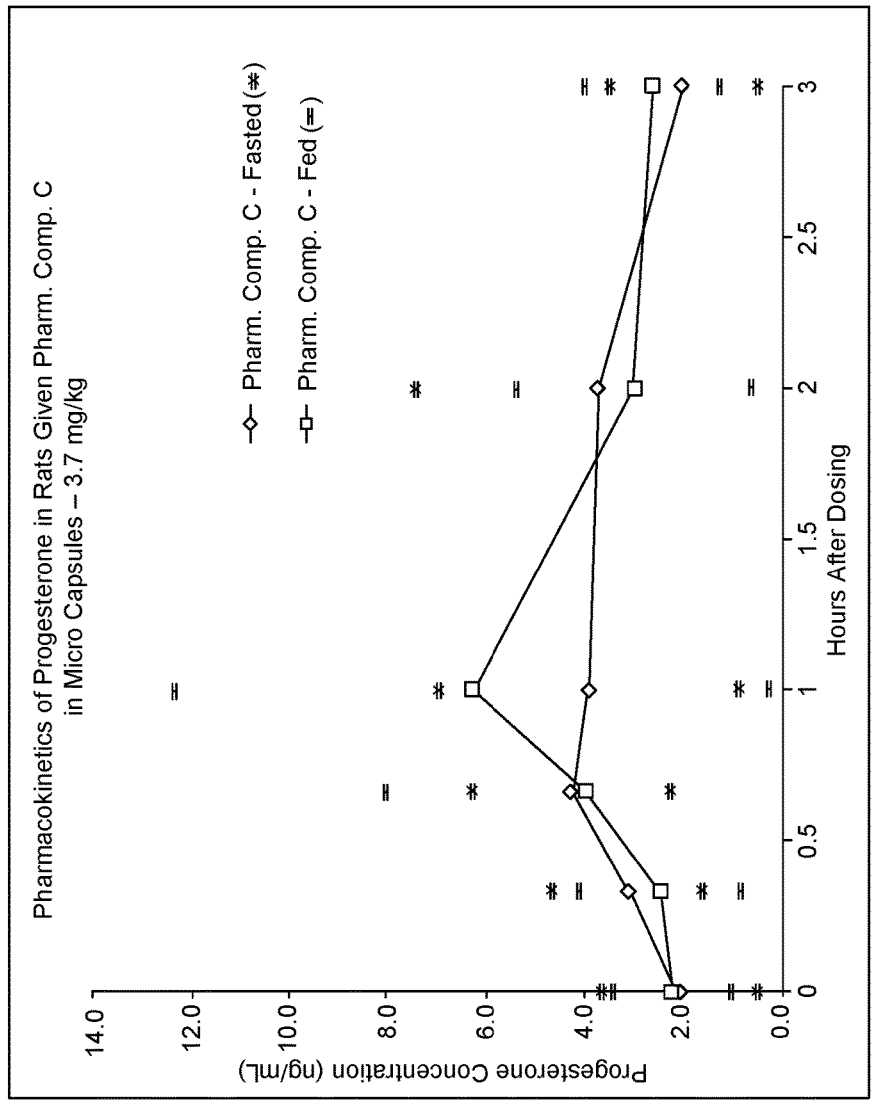
FIG. 9 is a graph of the plasma concentration of progesterone vs. time for fed and fasted rats dosed with 20 µl (3.7 mg/kg progesterone) of test pharmaceutical composition C in a gavage micro capsule.
Figure 10:
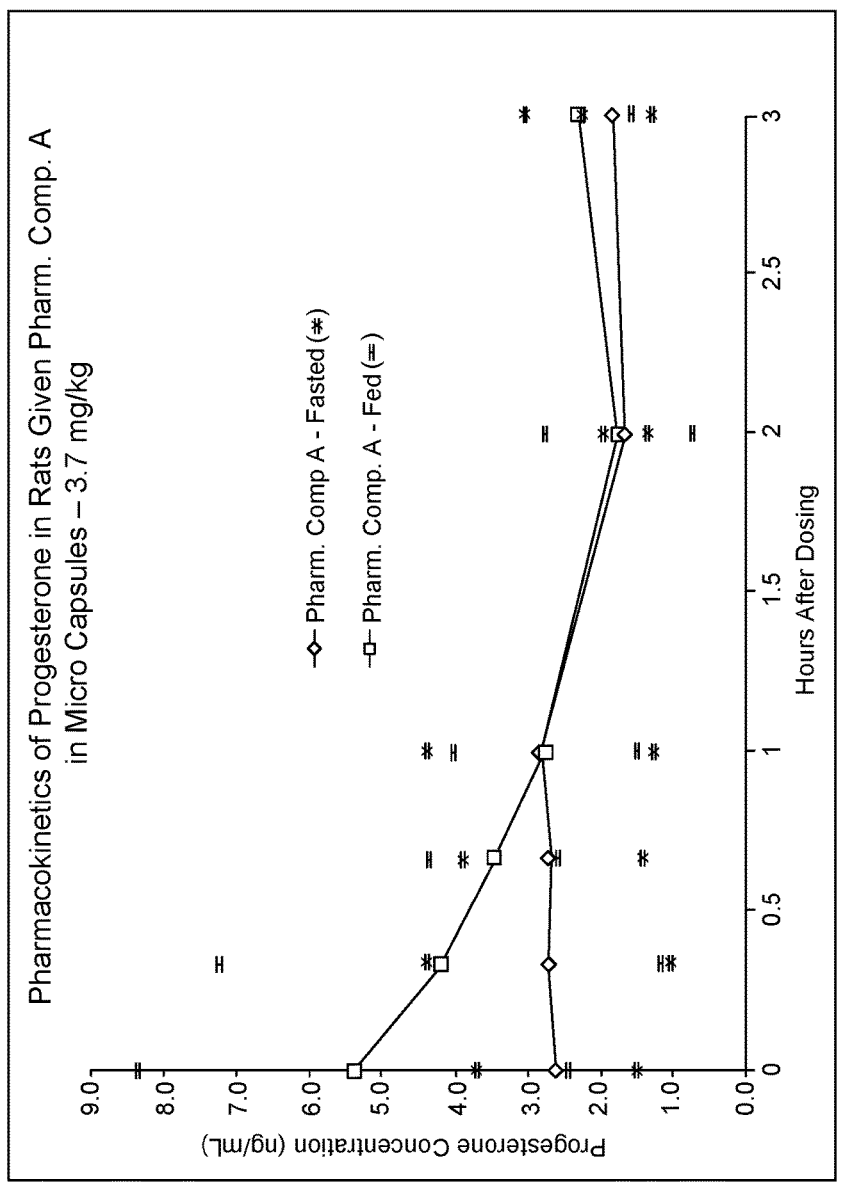
FIG. 10 is a graph of the plasma concentration of progesterone vs. time for fed and fasted rats dosed with 20 µl (3.7 mg/kg progesterone) of test pharmaceutical composition A in a gavage micro capsule.

In addition, the relative amount of a down-stream metabolite of progesterone (allopregnanolone sulfate) was much higher in rats dosed with PROMETRIUM (AUC approximately 90% of the AUC for progesterone) than with the test pharmaceutical compositions (approximately 6-15%). Allopregnolone is believed to be associated with somnolence side effect in humans. In certain embodiments, Pharmaceutical Compositions A, B, C, or D can be administered to reduce or eliminate a somnolence side effect in patients needing progesterone therapy. See, FIGS. 3 and 4.

Each of test pharmaceutical compositions also provided faster onset of action than PROMETRIUM by over an hour and a half In certain embodiments, a faster onset of action demonstrates the improved bioavailability over currently available hormone formulations. Given the vast difference in progesterone concentration between PROMETRIUM and the described pharmaceutical compositions, these results are highly surprising and unexpected.

Example 4

Food Effect on Oral Absorption

According to the protocol, 56 male Sprague-Dawley rats were divided into 8 groups of 7 rats each. Each group was given one of three test pharmaceutical compositions or PROMETRIUM as set forth in Table 6 according to the schedule shown in Table 7. Animals in "Fed" groups were presented with a pre-weighed amount of food 15 minutes prior to receiving a given pharmaceutical composition. The food was removed 45 minutes after dosing and weighed to calculate average consumption per animal. Animals in fasted groups received food approximately 4 hours after dosing.

TABLE 6

| Group | Pharmaceutical Composition | Fed/Fasted |
|---|---|---|
| 1 | PROMETRIUM | Fasted |
| 2 | PROMETRIUM | Fed |
| 3 | D | Fasted |
| 4 | D | Fed |

TABLE 6-continued

| Group | Pharmaceutical Composition | Fed/Fasted |
|---|---|---|
| 5 | A | Fasted |
| 6 | A | Fed |
| 7 | C | Fasted |
| 8 | C | Fed |

TABLE 7

| Study Day | Event |
|---|---|
| −4 | Animals were transferred to surgery facility and were group/gang housed. |
| −3 | Animals were observed. |
| −2 | Animals were observed. |
| −1 | Animals were fitted with jugular vein |

TABLE 7-continued

| Study Day | Event |
|---|---|
| | catheters (vaporized isoflurane anesthesia) and treated with analgesics. The animals were fasted for 16 hours starting at 4:00 PM. |
| 0 | Gavage capsules were filled with 20 μl of composition per capsule. The Animals were either fed or fasted, as noted above, and given compositions via capsule gavage. Plasma samples were taken at 10, 20, 40, 60, 90, 120, 180, and 240 minutes post dosing. Frozen plasma samples were shipped on dry ice for analysis. |

The results of this study are show in FIGS. 7, 8, 9, and 10 and show that there was no clear food effect on the PK of any of the pharmaceutical compositions, but dose-normalized progesterone exposure for the test pharmaceutical compositions was approximately 5-fold higher for $C_{max}$ and 3-fold higher for $AUC_{0-t}$ than for PROMETRIUM.

In certain embodiments, the $C_{max}$ and $AUC_{0-t}$ differences between the test compositions and PROMETRIUM are surprising given that PROMETRIUM contains about 400 mg progesterone per gram of formulation, whereas the test pharmaceutical compositions contain 60 mg progesterone per gram of formulation (i.e. about 6 weight percent). In view of this significant difference in the amount of available progesterone when both compositions were dosed at equal volumes (i.e. 20 μl), a person of ordinary skill in the art would not have predicted that the present pharmaceutical compositions would enhanced oral bioavailability versus the reference composition (PROMETRIUM).

The breadth and scope of the present invention should not be limited by any of the above-described exemplary embodiments, but should be defined only in accordance with the following claims and their equivalents.

All patents, patent applications, and other reference noted or referenced in this application are hereby incorporated by reference in their entirety.

What is claimed is:

1. A method of treating a disease or condition associated with reduced progesterone levels, the method comprising administering to a subject in need thereof a pharmaceutical composition comprising:
    about 6 weight percent progesterone,
    from about 1 weight percent to about 15 weight percent of a polysorbate, and
    from about 70 weight percent to about 90 weight percent of a medium chain oil,
    wherein
    the medium chain oil comprises at least about 50 weight percent of a predominantly medium chain monoglyceride and up to about 10 weight percent of a complex medium chain diglyceride; and
    the progesterone is fully solubilized.

2. A method of treating a disease or condition associated with reduced progesterone levels, the method comprising administering to a subject in need thereof an oral, fully-solubilized progesterone pharmaceutical composition comprising:
    a polysorbate and about 6 weight percent progesterone, wherein the progesterone and the polysorbate are present in a weight ratio of from about 1:2 to about 2:1; and
    a medium chain oil comprising at least about 50 weight percent of a predominantly medium chain monoglyceride and up to about 10 weight percent of a complex medium chain diglyceride, the medium chain oil not containing more than about 10 weight percent triglycerides.

3. The method of claim 1, wherein the disease or condition associated with reduced progesterone levels is selected from the group consisting of menopause, endometrial hyperplasia; secondary amenorrhea; prevention of preterm birth; and osteoporosis.

4. The method of claim 2, wherein the disease or condition associated with reduced progesterone levels is selected from the group consisting of menopause, endometrial hyperplasia; secondary amenorrhea; prevention of preterm birth; and osteoporosis.

5. The method of claim 1 wherein the predominantly medium chain monoglyceride and the progesterone are present at a weight ratio of about 10:1 to about 15:1.

6. The method of claim 1, wherein the medium chain oil comprises at least about 70 weight percent of a predominantly medium chain monoglyceride.

7. The pharmaceutical composition of claim 6, wherein the polysorbate is selected from the group consisting of polysorbate 20, polysorbate 40, polysorbate 60, polysorbate 65, and polysorbate 80.

8. The method of claim 1, wherein the pharmaceutical composition provides an oral bioavailability of at least about 150 percent as measured by an increase in AUC when compared to a reference product.

9. The method of claim 1, wherein the pharmaceutical composition further comprises at least one of a polyoxyethylene hydrogenated castor oil, a D-α-Tocopherol polyethylene glycol succinate derivative, or a terpene.

10. The method of claim 9, wherein the predominantly medium chain monoglyceride comprises at least about 90 weight percent of the medium chain oil.

11. The method of claim 10, wherein the polysorbate is selected from the group consisting of polysorbate 20, polysorbate 40, polysorbate 60, polysorbate 65, and polysorbate 80.

12. The method of claim 9, wherein the pharmaceutical composition provides an oral bioavailability of at least about 150 percent as measured by an increase in AUC when compared to a reference product.

13. The method of claim 2, wherein the polysorbate is selected from the group consisting of polysorbate 20, polysorbate 40, polysorbate 60, polysorbate 65, and polysorbate 80.

14. The method of claim 2, wherein the pharmaceutical composition provides an oral bioavailability of at least about 150 percent as measured by an increase in AUC when compared to a reference product.

15. The method of claim 2, further comprising at least one of a polyoxyethylene hydrogenated castor oil, a d-α-tocopherol polyethylene glycol succinate derivative, or a terpene.

* * * * *